US008383597B2

(12) United States Patent　　　(10) Patent No.: US 8,383,597 B2
Huang　　　(45) Date of Patent: Feb. 26, 2013

(54) G PROTEINS IN TUMOR GROWTH AND ANGIOGENESIS

(75) Inventor: Xin-Yun Huang, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1208 days.

(21) Appl. No.: 11/805,715

(22) Filed: May 24, 2007

(65) Prior Publication Data

US 2008/0020994 A1　　Jan. 24, 2008

Related U.S. Application Data

(60) Provisional application No. 60/808,489, filed on May 25, 2006.

(51) Int. Cl.
*A61K 31/70*　　(2006.01)
*C07H 21/02*　　(2006.01)
*C07H 21/04*　　(2006.01)

(52) U.S. Cl. .................. 514/44 A; 536/24.5
(58) Field of Classification Search ............. 514/44
See application file for complete search history.

(56) References Cited

U.S. PATENT DOCUMENTS

| 5,328,470 A | 7/1994 | Nabel et al. |
| 5,641,673 A | 6/1997 | Haseloff et al. |
| 5,981,732 A | 11/1999 | Cowsert |

FOREIGN PATENT DOCUMENTS
EP　　0321201 A2　6/1989

OTHER PUBLICATIONS

Hammond et al. (Nature Reviews Genetics 2001, vol. 2:110-119).*
Vickers et al. (Journal of Biological Chemistry, 2003 vol. 278: 7108-7118, Epub date Dec. 23, 2002).*
Scanlon, KJ (Current Pharmaceutical Biotechnology, 2004 vol. 5:415-420).*
"RNA Interference (RNAI) and Post-transcriptional Gene Silencing (PTGS)", © Copyright 2002 Ambion®, Inc., (2002), 9 pgs.
"siRNA Design Guidelines", Technical Bulletin #506, *Ambion®—The RNA Company*, [online]. [archived Apr. 27, 2006]. Retrieved from the Internet: <URL: http://web.archive.org/web/20060427035926/http://www.ambion.com/techlib/tb/tb_506.html>, 8 pgs.
"Understanding Angiogenesis", [online]. [archived Mar. 24, 2006]. Retrieved from the Internet: <URL: http://web.archive.org/web/20060324023456/http://www.angio.org/understanding/content_understanding.html>, 7 pgs.
Bartel, D. P., et al., "Isolation of New Ribozymes from a Large Pool of Random Sequence", *Science*, 261(5127), (1993), 1411-1418.
Bourne, H. R., "How Receptors Talk to Trimeric G Proteins", *Current Opinion in Cell Biology*, 9, (1997), 134-142.
Buccione, R., et al., "Food and Mouth: Podosomes, Invadopodia and Circular Dorsal Ruffles", *Nature Reviews Molecular Cell Biology*, 5, (2004),647-657.
Carmeliet, P., "Angiogenesis in Life, Disease and Medicine", *Nature*, 438, (2005), 932-936.

(Continued)

*Primary Examiner* — Terra Cotta Gibbs
(74) *Attorney, Agent, or Firm* — Schwegman, Lundberg & Woessner, P.A.

(57) ABSTRACT

The invention provides an agent that reduces the expression of $G\alpha_{12}$ or $G\alpha_{13}$ polypeptide, as well as an agent that enhances G protein $G\alpha_{12}$ or $G\alpha_{13}$ expression and/or activity. An agent of the invention may be used to decrease or increase G protein $G\alpha_{12}$ or $G\alpha_{13}$ expression and/or activity thereby to treat or prevent the onset of a disease or condition associated with $G\alpha_{12}$ or $G\alpha_{13}$ expression and/or activity. The invention also provides a method for screening for an anti-cancer or anti-angiogenesis agent, as well as an agent that promotes angiogenesis.

12 Claims, 26 Drawing Sheets

OTHER PUBLICATIONS

Cech, T. R., "Ribozyme Engineering", *Current Opinion in Structural Biology*, 2(4), (1992), 605-609.

Cech, T. R., "Self-Splicing of Group I Introns", *Annual Review of Biochemistry*, 59, (1990),543-568.

Cech, T. R., "The Chemistry of Self-Splicing RNA and RNA Enzymes", *Science*, 236(4808), (1987), 1532-1539.

Chen, S. , et al., "Gene Therapy for Brain Tumors: Regression of Experimental Gliomas by Adenovirus-Mediated Gene Transfer in vivo", *Proc. Natl. Acad. Sci. USA*, 91(8), (1994),3054-3057.

Chen, Z. , et al., "Structure of the p115RhoGEF rgRGS Domain-$G\alpha 13/i1$ Chimera Complex Suggests Convergent Evolution of a GTPase Activator", *Nature Structural & Molecular Biology*, 12(2), (2005), 191-197.

Conklin, B. R., et al., "Substitution of Three Amino Acids Switches Receptor Specificity of $G_q\alpha$ to that of $G_i\alpha$", *Nature*, 363, (1993), 274-276.

Couture, L. A., "Anti-Gene Therapy: The Use of Ribozymes to Inhibit Gene Function", *Trends in Genetics*, 12(12), (1996),510-515.

Elbashir, S. M., "Duplexes of 21-Nucleotide RNAs Mediate RNA Interference in Cultured Mammalian Cells", *Nature*, 411 (2001),494-498.

Garcia, P. D., et al., "Transducin-$\alpha$ C-Terminal Mutations Prevent Activation by Rhodopsin: A New Assay Using Recombinant Proteins Expressed in Cultured Cells", *The EMBO Journal*, 14(18), (1995), 4460-4469.

Gilchrist, A. , et al., "G$\alpha$ Minigenes Expressing C-Terminal Peptides Serve as Specific Inhibitors of Thrombin-Mediated Endothelial Activation", *The Journal of Biological Chemistry*, 276(28), (2001), 25672-25679.

Gohla, A. , et al., "Differential Involvement of $G\alpha_{12}$ and $G\alpha_{13}$ in Receptor-Mediated Stress Fiber Formation", *The Journal of Biological Chemistry*, 274(25), (1999), 17901-17907.

Gu, J. L., et al., "Interaction of $G\alpha_{12}$ with $G\alpha_{13}$ and $G\alpha_q$ Signaling Pathways", *Proc. Natl. Acad. Sci.*, 99(14), (2002),9352-9357.

Hall, A , "Rho GTPases and the Actin Cytoskeleton", *Science*. 279(5350), (1998), 509-514.

Harborth, J., "Sequence, Chemical, and Structural Variation of Small Interfering RNAs and Short Hairpin RNAs and the Effect on Mammalian Gene Silencing", *Antisense and Nucleic Acid Drug Development*, 13(2), (2003),83-105.

Haseloff, J., et al., "Simple RNA Enzymes with New and Highly Specific Endoribonuclease Activities", *Nature*, 334, (1988),585-591.

Hirsch, J. P., et al., "The Carboxyl Terminus of Scg1, the G alpha Subunit Involved in Yeast Mating, is Implicated in Interactions With the Pheromone Receptors", *Genes & Development*, 5(3), (1991),467-474.

Jiang, Y. , et al., "The G Protein G$\alpha$ 12 Stimulates Bruton's Tyrosine Kinase and a rasGAP Through a Conserved PH/BM Domain", *Nature*, 395, (1998),808-813.

Kallal, L., et al., "Analysis of the Receptor Binding Domain of Gpa1p, the $G_\alpha$ Subunit Involved in the Yeast Pheromone Response Pathway", *Molecular and Cellular Biology*, 17(5), (1997), 2897-2907.

Lowry, W. , et al., "Csk, a Critical Link of G Protein Signals to Actin Cytoskeletal Reorganization", *Developmental Cell*, 2(6), (2002), 733-744.

Lyden, D. , et al., "Id1 and Id3 are Required for Neurogenesis, Angiogenesis and Vascularization of Tumour Xenografts", *Nature*, 401(6754), (1999), 670-677.

Masters, S. B., et al., "Carboxyl Terminal Domain of $G_{s\alpha}$ Specifies Coupling of Receptors to Stimulation of Adenylyl Cyclase", *Science*, 241(4864), (1988), 448-451.

Onrust, R., et al., "Receptor and $\beta\gamma$ Binding Sites in the $\alpha$ Subunit of the Retinal G Protein Transducin", *Science*, 275(5298), (1997), 381-384.

Osawa, S. , et al., "The Effect of Carboxyl-Terminal Mutagenesis of $G_t\alpha$ on Rhodopsin and Guanine Nucleotide Binding", *The Journal of Biological Chemistry*, 270(52), (1995), 31052-31058.

Ridley, A J., et al., "The Small GTP-Binding Protein rac Regulates Growth Factor-Induced Membrane Ruffling", *Cell.* 70(3), (1992),401-410.

Risau, W., "Mechanisms of Angiogenesis", *Nature*, 386(6626), (1997), 671-674.

Shan, D., et al., "Synthetic Analogues of Migrastatin that Inhibit Mammary Tumor Metastasis in Mice", *Proc. Natl. Acad. Sci. USA*, 102(10), (2005), 3772-3776.

Simon, M. I., et al., "Diversity of G Proteins in Signal Transduction", *Science*, 252, (1991), 802-808.

Sugihara, K., et al., "Rac 1 is Required for the Formation of Three Germ Layers During Gastrulation", *Oncogene*, 17(26), (1998), 3427-3433.

Sullivan, K. A., et al., "Identification of Receptor Contact Site Involved in Receptor-G Protein Coupling", *Nature*, 330, (1987),758-760.

Weed, S. A., et al., "Translocation of Cortactgin to the Cell Periphery is Mediated by the Small GTPase Rac1", *Journal of Cell Sciience*, 111(16), (1998), 2433-2443.

Wu, H., et al., "Evaluation of the Catalytic Mechanism of the p21-Activated Protein Kinase PAK2", *Biochemistry*, 42, (2003), 1129-1139.

Yancopoulos, G. D., et al., "Vascular-Specific Growth Factors and Blood Vessel Formation", *Nature*, 407(6801), (2000), 242-248.

Yang, S. , et al., "$Ca^{2+}$ Influx Through L-Type $Ca^{2+}$ Channels Controls the Trailing Tail Contraction in Growth Factor-Induced Fibroblast Cell Migration", *The Journal of Biological Chemistry*, 28(29), (2005), 27130-27137.

Kelly, P., et al., "A role for the G12 family of heterotrimeric G proteins in prostate cancer invasion", J Biol Chem., 281(36), (Sep. 8, 2006), 26483-90.

Kelly, P., et al., "Biologic Functions of the G12 Subfamily of Heterotrimeric G Proteins: Growth, Migration, and Metastasis", Biochemistry, 46, (2007), 6677-6687.

Kelly, P., et al., "The G12 family of heterotrimeric G proteins promotes breast cancer invasion and metastasis", Proc Natl Acad Sci U S A., 103(21), (May 23, 2006), 8173-8.

Low, Jonathan, et al., "High-Content Imaging Analysis of the Knockdown Effects of Validated siRNAs and Antisens Oligonucleotides", Journal of Biomolecular Screening 12(6); 2007, (Apr. 1, 2007), 15.

Radhika, V., et al., "Galpha(13) Stimulates Cell Migration through Cortacin-interacting Protein Hax-1", The Journal of Biological Chemistry, 279(47), (2004), 49406-49413.

\* cited by examiner

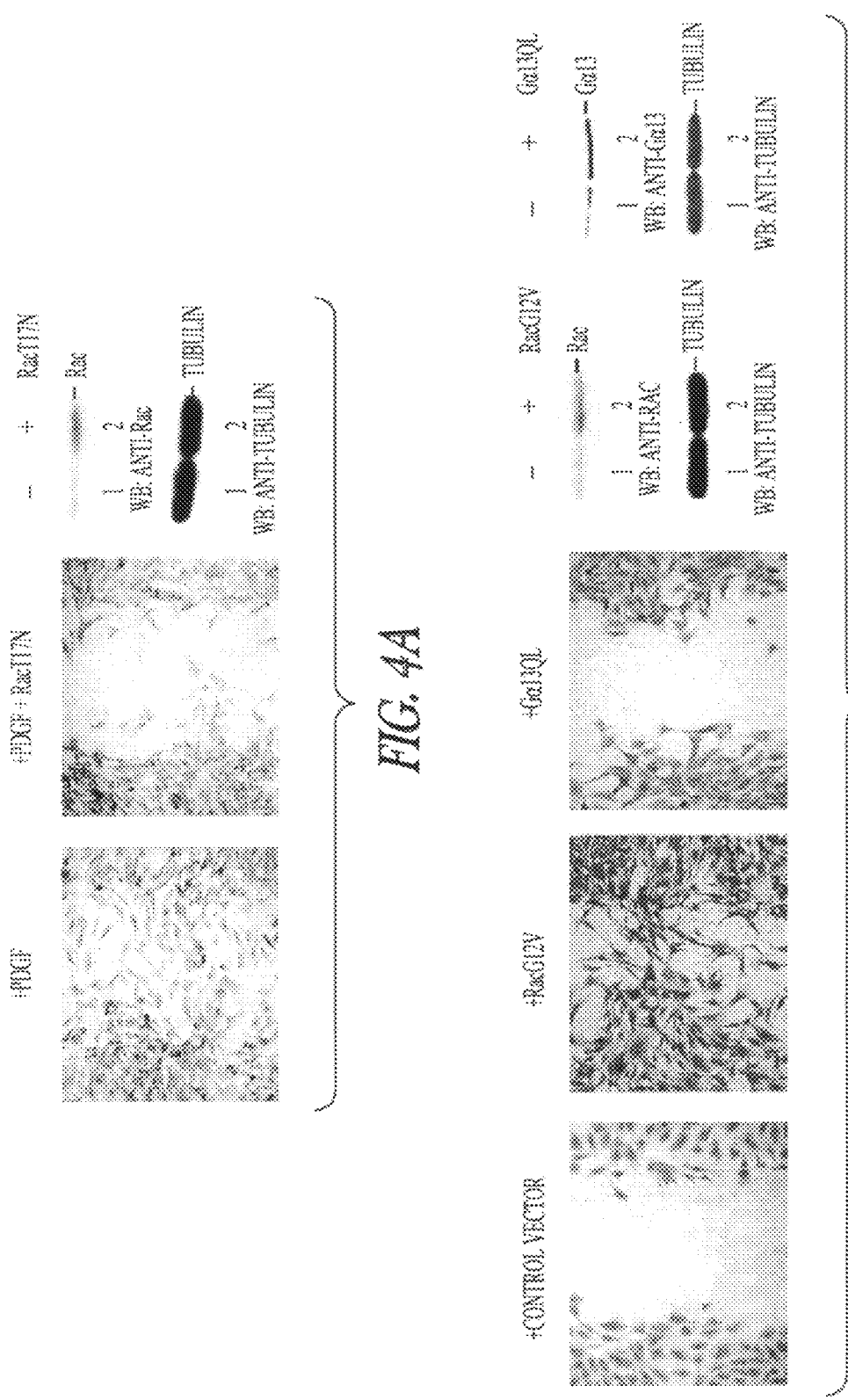

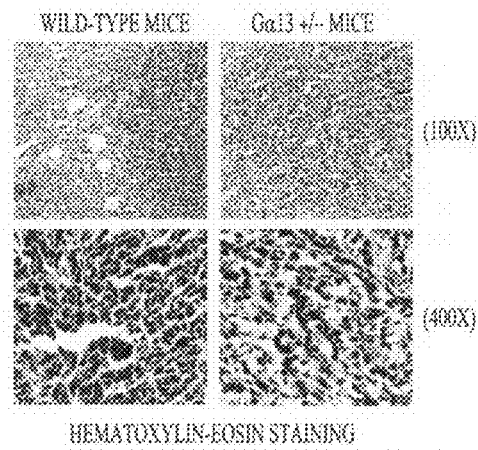
FIG. 9E
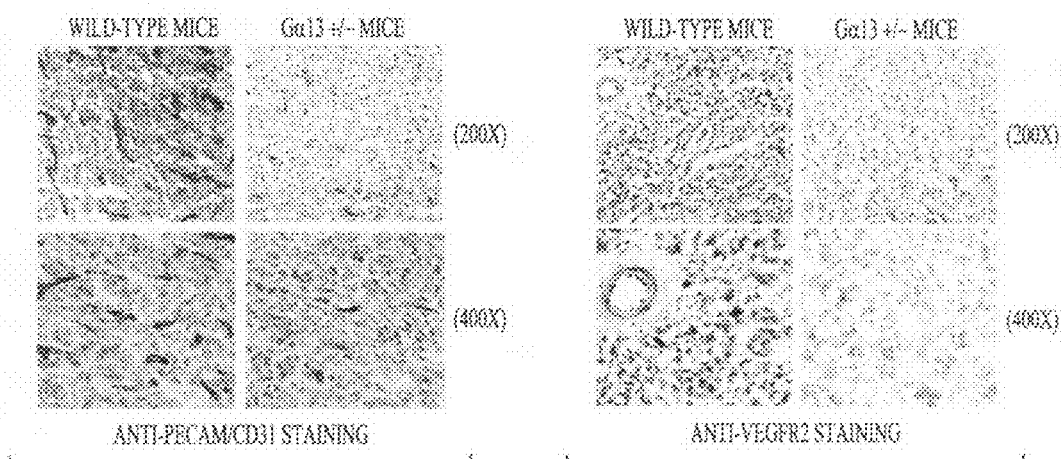
FIG. 9F
FIG. 9G

```
   1 gggcgacgag tgcgggcctc ggagcgactg cagcggcggc ggcggacgcg gcctgaggcg
  61 agcggcgggg cgtggggcgg tgcctcggcc cgggctcgcc ctcgccggcg ggagcgtcca
 121 tggccccgg gcgccggcgg ggcgcggccg cggcctgagg ggccatgtcc ggggtggtgc
 181 ggaccctcag ccgctgcctg ctgccggccg aggccggcgg ggcccgcgag cgcaggcgg
 241 gcagcggcgc gcgcgacgcg gagcgcgagg cccggaggcg tagccgcgac atcgacgcgc
 301 tgctggcccg cgagcggcgc gcggtccggc gcctggtgaa gatcctgctg ctgggcgcgg
 361 gcgagagcgg caagtccacg ttcctcaagc agatgcgcat catccacggc cgcgagttcg
 421 accagaaggc gctgctggag ttccgcgaca ccatcttcga caacatcctc aagggctcaa
 481 gggttcttgt tgatgcacga gataagcttg gcattccttg gcagtattct gaaaatgaga
 541 agcatgggat gttcctgatg gccttcgaga caaggcggg gctgcctgtg gagccggcca
 601 ccttccagct gtacgtcccg gccctgagcg cactctggag ggattctggc atcagggagg
 661 ctttcagccg gagaagcgag tttcagctgg gggagtcggt gaagtacttc ctggacaact
 721 tggaccggat cggccagctg aattactttc ctagtaagca agatatcctg ctggctagga
 781 aagccaccaa gggaattgtg gagcatgact tcgttattaa gaagatcccc tttaagatgg
 841 tggatgtggg cggccagcgg tcccagcgcc agaagtggtt ccagtgcttc gacgggatca
 901 cgtccatcct gttcatggtc tcctccagcg agtacgacca ggtcctcatg gaggacaggc
 961 gcaccaaccg gctggtggag tccatgaaca tcttcgagac catcgtcaac aacaagctct
1021 tcttcaacgt ctccatcatt ctcttcctca acaagatgga cctcctggtg gagaaggtga
1081 agaccgtgag catcaagaag cacttcccgg acttcagggg cgacccgcac aggctggagg
1141 acgtccagcg ctacctggtc cagtgcttcg acaggaagag acggaaccgc agcaagccac
1201 tcttccacca cttcaccacc gccatcgaca ccgagaacgt ccgcttcgtg ttccatgctg
1261 tgaaagacac catcctgcag gagaacctga aggacatcat gctgcagtga gcgaggaagc
1321 cccgggggttt gtcgtcgttg agcagcccc acggctgtcg gtcagactct tgggtgtgtg
1381 ttgtctgtgt ggtccttgag tgggtttctc ggatccgtgc cctggaatac ctggctcagg
1441 aatgctgtca gaccagccag ccagcgagct ctaggcaaaa ggacatggaa actgtcacgt
1501 tagctactga atcctggggg cgagtgaaac tactgaaaat ccgagtgatg atgttgtgaa
1561 tacggaacac ctaatcacac agcttgcttt gcttttacag aaacgttcct ctttttctga
1621 cgcagtttaa ttgaggaccg tgttgtgtgt gtatgtgtgt acacacgctc tgtctttaat
1681 gacagaaaca caaaaaccag ctggccttgc agacggcttt tctaactcac aagtcttccc
1741 tgagacagac taacctgaaa gctttgccta acagtagctt gtagagatcc agtgcacgcc
1801 gatgctgcta aactcagtgc ctgagcccgg cctgcagcc ccagccgcag tgtctgaagg
1861 ccacctccca aagggagcac gttgccttt caaactcccg tgccgatttc ctaagagccc
1921 ctagtccaag cctctcagat gaagctgagg agccgtgcct aggatccctt cccagctctg
1981 aggacgggct gcaagctct gcaggtgtgg attccacctta cgcccctaca gcaggctcag
2041 cccttcccac cctgcccat gcccagcaga acaacaggga gtgagacagg atgcccacgg
2101 tgactgccgc tccgtccgtg cacacacagc ggtgctcttc tcccttagc cacccactgc
2161 ccaacccaac ggcaaagaca cagaaaccag gtcccttgc agacggctct cccatcttcc
2221 tgcaagtcat ctgctcacac acagttggca gcacatagcg tttccttctt tcagaaacat
2281 tcctcttctg gggcttcaga aagctggcaa ggccactagc agagcttttg ttaatgcccc
2341 agctgcttgg cgagctaaca gctgaccttt cgggaagccc acagacgctg gaggaatctt
2401 gagtttctcc aaactgccgc tccaccagtg cctttggaca gccgtgcctg ttcgccgctc
2461 tccctaagtc tgattctcat cgaggcccct cgcttctatg actgtgcttg cagaagagta
2521 aacactctcg gatgccgctg tcctggggga gccgcggga gcctgtgaat gttgatacga
2581 gctggccagt cctcacttgt gcagctacct gccaggtggc tttcactgtg
2641 tttaaaatac attgcattcc aagctggtcc cctctgtgta tcactctact gagaaatcct
2701 gcctagtgtg ttttgggatg tgtcctagca tttacaagaa aatgaaaagc gtcctcttaa
2761 ttggcacccg aatgttgctg tggctcagtc acatatccca gggccctcgt cccgaggccg
2821 tgctgccccg agccccgagc cctctgcag ctcaccctttg gcttgttttc cgcaaacccg
2881 gtaaacgcaa gcccttgggg cagatgcaga agcagaagag ggaggggaaa cctgcctctg
2941 ggtcacctg ttagcacagc gttctcatcg ggagacagca tggaactctc tctcgcagtg
3001 ctcgaggctg tgtgtcagtg tttgctgggc ttgtggctcc ttttttggct ggataaagaa
3061 gtcgctgttt ttgtactgct tctgtggctc ttcacagacc tcacggatgt gaccggagat
3121 gagtgccgat gaccacgttt taaaggagaa agagagctgc tggtggggcc ctcggggtgg
3181 tctcaggtcc catttgcagt ctgcaacagt gacgcgcagc ccggtccgga gcgtggtgag
3241 ctttgtttgc cttctgggtc agctttcgct gtgtcctcc tgtgtgttag aatccagagc
3301 ccagaggaag tgcaagcggg tcctccgcca acggggagag cctcttcgcg gcgctgttgg
3361 cgacagcagc gctgtgattc gcgtagcagg ggagttgttt gaaacacctt cctgagtagt
```

*FIG. 11A*

```
3421 ccggccttgt caatgagtgc ttgttttcct ttaaacagtc tgacatattt actcgtcact
3481 ttcaaaccag aagcatgaga ggaaggagat attgtggggt ccgtttaact cgatagaaag
3541 cgcaggggga tggcccccgg cgcgggctct tgacccgctc agcgctgacc ccaccgccct
3601 ggccgaggca cttggccttg ctgagctgga cttcctcctc ctcctcctca tgaccgggt
3661 gaattagaac gttttaaag acaccccctt ccaaattctg taacacattg taattggaga
3721 agaaggaaac tctgcaaggc taaactgtca ttcacaactt ggctacacat agactctagt
3781 cagttttgtc tccagaacct taggcttttg tatttttaa ttttaatttc actgttaatc
3841 cttattgtct tttttattaa gatgttggaa aagcaggagg tagttgtgcc tcaattattg
3901 caaaaatgta acaataaagt tcctcaaaat aagatctgtt cctcatagct atactgtgta
3961 cacataagac gcatataggg ttttactgaa atctatttt aactcttatg ttcgtagaga
4021 aattgtttca aggatttga gtcataggtc tgtaatttat agagatctct agaattctta
4081 ttgtaatttt cctacttctt tgataaaaga aaaataagtc agattgttaa ctccaagatt
4141 gaaaaaaaaa actcttgaaa gaagattatt agttgtaact aatttagggg ttctgggcac
4201 agacatctaa cctggtattg taaggcagag gctcccattg gaatggtagt ggtccgggtc
4261 agttgttcat ggtgtaagct ttgcacagtg tattaacatt gggagggtct ggcttgaaaa
4321 tttggccacc ctcagcctct gaatgtttat taaataaat ttagtctttc tttgcttaat
4381 ataaaaaaaa aaaaaaaa (SEQ ID NO: 1)
```

*FIG. 11B*

```
MSGVVRTLSRCLLPAEAGGARERRAGSGARDAEREARRRSRDIDALLARERRAVRRLVKILLLGAGESGKSTFLKQM
RIIHGREFDQKALLEFRDTIFDNILKGSRVLVDARDKLGIPWQYSENEKHGMFLMAFENKAGLPVEPATFQLYVPAL
SALWRDSGIREAFSRRSEFQLGESVKYFLDNLDRIGQLNYFPSKQDILLARKATKGIVEHDFVIKKIPFKMVDVGGQ
RSQRQKWFQCFDGITSILFMVSSSEYDQVLMEDRRTNRLVESMNIFETIVNNKLFFNVSIILFLNKMDLLVEKVKTV
SIKKHFPDFRGDPHRLEDVQRYLVQCFDRKRRNRSKPLFHHFTTAIDTENVRFVFHAVKDTILQENLKDIMLQ
(SEQ ID NO: 2)
```

*FIG. 12*

```
   1 ccacgcgtcc ggggagccgg aggggcccgc cgaggcggcg gcggcggcgg caagatggcg
  61 gacttcctgc cgtcgcggtc cgtgctgtcc gtgtgcttcc ccggctgcct gctgacgagt
 121 ggcgaggccg agcagcaacg caagtccaag gagatcgaca aatgcctgtc tcgggaaaag
 181 acctatgtga agcggctggt gaagatcctg ctgctgggcg cgggcgagag cggcaagtcc
 241 accttcctga agcagatgcg gatcatccac gggcaggact tcgaccagcg cgcgcgcgag
 301 gagttccgcc ccaccatcta cagcaacgtg atcaaaggta tgagggtgct ggttgatgct
 361 cgagagaagc ttcatattcc ctggggagac aactcaaacc aacaacatgg agataagatg
 421 atgtcgtttg ataccoggc cccatggca gcccaaggaa tggtggaaac aagggttttc
 481 ttacaatatc ttcctgctat aagagcatta tgggcagaca gcggcataca gaatgcctat
 541 gaccggcgtc gagaatttca actgggtgaa tctgtaaaat atttcctgga taacttggat
 601 aaacttggag aaccagatta tattccatca caacaagata ttctgcttgc cagaagaccc
 661 accaaaggca tccatgaata cgactttgaa ataaaaaatg ttcctttcaa aatggttgat
 721 gtaggtggtc agagatcaga aggaaacgt tggtttgaat gtttcgacag tgtgacatca
 781 atacttttcc ttgtttcctc aagtgaattt gaccaggtgc ttatggaaga tcgactgacc
 841 aatcgcctta cagagtctct gaacattttt gaaacaatcg tcaataaccg ggttttcagc
 901 aatgtctcca taattctgtt cttaaacaag acagacttgc ttgaggagaa ggtgcaaatt
 961 gtgagcatca aagactattt cctagaattt gaagggatc cccactgctt aagagacgtc
1021 caaaaattcc tggtggaatg tttccggaac aaacgccggg accagcaaca gaagcccta
1081 taccaccact tcaccactgc tatcaacacg gagaacatcc gccttgtttt ccgtgacgtg
1141 aaggatacta ttctgcatga caacctcaag cagcttatgc tacagtgatg tacaaaagac
1201 ttgctgtttt aatatctttt tgtgtttttg atgttttctg tttgttttgt tttttaaaat
1261 agcagtttac aaccagaatt agaacaatct taattctacg tttaacttct tgaaaatctt
1321 agtacttttt ctgcggcctt tggtttgtgg ctgaaagctg ttgagtgact catcgccaag
1381 atttgctgta atgcaggctt tgatctgttt caccatggct tctattcaag tccagtaaaa
1441 acctccagc tgacctcaga ctaggcatat ttcaggcttt aaattattct actttccaaa
1501 ctgaattctc ctgcagtgcc aagtatcaaa ggtgtcctta aatacttgta gggatgaggt
1561 taggaatatt cagttccaaa acaagatatc ttctgtccgc cttacatata gcagtgacac
1621 ttgttgccta acttatggt gacctcctat tttgtaaggg ctgttagaag ttctatctaa
1681 gaaatggcat tctgtaggtt tatagaaggt ttagccttca tattttaatt gcttgtatac
1741 acaacagctg ttttgctttt agatttctgt gtttctgaag gtaatgttct tcctgttttc
1801 aagtttacat aaggatcttt ggtctgatgc tgatgaagag ttcacaggtg gtatgggaga
1861 gcaaaaggca agctaatgct gtttaccgtg ttttggtcaa acgtaacgag tgaaatagaa
1921 tttgcctttc tcatatttaa ttatcatgta gtttaatgta ccatatgtga aacattctgg
1981 ccatagcagc aactaaaaac tgcaagcaac ttggtaacag aactttctaa ataaacttaa
2041 cctgttccag aatgtcatgt atttgacttt taagccctat ctcagttggt cagtaaagac
2101 caatccttac tgtaggaaat cattgttgta tcatcacaaa catctatctt ttgctgtcct
2161 gtccagtccc atcaactcca cactgtgcca tttgtggcat cgtttgtttt atttggagtt
2221 tgctaagggc agtattttc tgtcaagact attcaagaag gcattatttg agattcctgt
2281 tcattcttgg tgtgtctcta acagatacag tatgtataca tttgtataat tgttgttgtt
2341 gaaagtccag ctttttgag gtatatttta aatgttttaa ggatgcttaa aggatcagt
2401 agtaattttt ttagttcgca cctaaagatg attacattga cctccccga ctgcttacca
2461 aattaaaatg tgtccacgaa gtagctttgt gatcgcagat acattccatag tgaactcatc
2521 agaatggctg gtttgcagta ctgaaatact atcttctagg ctgtatgtag tgctacaatt
2581 agagaaacag aagtccaagg ctggcgacag cttgaaaagt ctgacagctt ttctactttt
2641 cctgaaaatt ttaagactgt gatatctgtc attttactgt atagctgact gtgtactcag
2701 gtatttatt ggtccttgaa agattggtcg ttatggatca cccagccttt ccaagtcagt
2761 ggctgttgtt ctgtcttgct gtctgatacg agagtggggc ttttcagtga actaaccagg
2821 gattgttctt gacatacctg acttttctca catttgaact tccactatca ttgtatccat
2881 ataacttcta gcatttcat gccatggtaa tccatgagct acacatacgt agcccgcac
2941 cgtgatgcaa gttcatggta tcgtgcatgt tcgtggtatc atggtatcat tcatgcgtgt
3001 ttgaatagtt ctacatctag tgcttcttgc caaaagaat acattgttta aattcacaaa
3061 attagcataa ttgcagtgct aatgaatatc ggaatatgtg cacagtaaca tttggactat
3121 tcattggaga gtttaccccat acatttagca aattgaatgg ccaaaacatt tgactccagt
3181 gagggctcaa gttagatccc tatagaaaga ggacacttca tcttacttaa gtcatagtta
```

*FIG. 13A*

```
3241 agatctgtga tacgaaccat agatattgcc tgacaaagca gaaatcacca agtttccccc
3301 ttttgaatta ccaccaagaa gtgttgaaac accaaataga tatcatgtta ttttgggcat
3361 ttgcagtttt cttccctgct gcatgtaatg tctcagaatc aacattcttt taaaatctag
3421 actatatttt gaggcaatga attacttata ttcaacttag gcttgttttg acattcagta
3481 gaactttaag ttcaatctaa aggcttcagt ccacattttt ttatacgttg tattttaaaa
3541 acgtttgaaa ggagtcttac acctgtatca tgaaaactga atcctttga ataccacta
3601 tatgaagaga gagatgaaat ttagtgaaca gaattgaaaa ggtgctcata atttcactat
3661 gcaaacttac cccagtctct aaaaaagtaa tttagattta aagttctttg atgtatttga
3721 ttttctaaat ctttatggtt atgatttgga ataaaatgtg cctaatcctg tgttacattc
3781 tgttcttaaa tctgaatgcc ttctcattta attctgagga atatcacac aagtgtcttc
3841 attgaccttg aagaaatgta tatacagttg ccttataaaa caacataaat ttagaccata
3901 acttttatag agaaagggtt ttgtcaaatg ttttctgaaa atctgagtaa ttcaaagcat
3961 gcctctgccc ctttaatatt tttaataacc tgcattgttg ctgtctgcca aatattaaat
4021 tgaaatcttc atttcaattt tattatctgg aaagggcact ggattgctct gcaaccaaag
4081 aaagcaatat ggaatgaaaa aactcattca cttttgtctt attttctttt aaggtgtatt
4141 ggcatgtaat ttgcatagag aaggtcctct ggttagtctc tcaaattgag gctgtttagg
4201 gaaatcctta ttcagttggt ggcagtggtt ggtttaaagt agaaggaaat aagatcgcct
4261 taataccaga aatgattaga agtgctgatt tagattcaac aaataccata tgtccttatc
4321 attttttgta agaagaaatt ggttaagtcc taactttcaa tgtgtaccca aatacttgta
4381 tttatgcttt tgataaaatg tattttcagc attaatacac atccgattat gccttattta
4441 tatatgaaga ataaagttac catgttatac tgttatgtcc taaaattcaa atcactattt
4501 gagaaaccct caaattggtg ctttcattat ataatgatac atttagacaa aaccccaaac
4561 taagccattt gaaacaagat tctctccatt gcagtttgta gcaatgttat ttctgtgtat
4621 gtcatgagaa ggctaaatat cagtgttaat ttcttgtttg aatccgtgaa atcatgcctg
4681 taaagcccaa acatttgtaa caaactccct aataaattta gagaaagtca aaaaaaaaaa
4741 aaaa (SEQ ID NO: 3)
```

*FIG. 13B*

MADFLPSRSVLSVCFPGCLLTSGEAEQQRKSKEIDKCLSREKTYVKRLVKILLLGAGESGKSTFLKQMRIIHGQDFD
QRAREEFRPTIYSNVIKGMRVLVDAREKLHIPWGDNSNQQHGDKMMSFDTRAPMAAQGMVETRVFLQYLPAIRALWA
DSGIQNAYDRRREFQLGESVKYFLDNLDKLGEPDYIPSQQDILLARRPTKGIHEYDFEIKNVPFKMVDVGGQRSERK
RWFECFDSVTSILFLVSSSEFDQVLMEDRLTNRLTESLNIFETIVNNRVFSNVSIILFLNKTDLLEEKVQIVSIKDY
FLEFEGDPHCLRDVQKFLVECFRNKRRDQQQKPLYHHFTTAINTENIRLVFRDVKDTILHDNLKQLMLQ (SEQ ID
NO: 4)

*FIG. 14*

G PROTEINS IN TUMOR GROWTH AND ANGIOGENESIS

RELATED APPLICATION

This application claims priority of U.S. provisional application Ser. No. 60/808,489, filed May 25, 2006, which is herein incorporated by reference in its entirety.

STATEMENT REGARDING FEDERALLY SPONSORED RESEARCH

Work relating to this application was supported by a grant from the U.S. Government (RO1 GM56904). The government may have certain rights in the invention.

TECHNICAL FIELD

The invention relates to G protein and its involvement in angiogenesis.

BACKGROUND

Blood vessels are crucial for organ growth in the embryo and repair of wounded tissue in the adult. An imbalance in the growth of blood vessels contributes to the pathogenesis of numerous disorders including malignant, ocular and inflammatory disorders. Carmeliet, Nature 438: 932-936 (2005). Excessive or abnormal angiogenesis may contribute to conditions such as obesity, asthma, diabetes, cirrhosis, multiple sclerosis, endometriosis, AIDS, bacterial infections and autoimmune disease. Id. Insufficient angiogenesis may cause endothelial cell dysfunction and vessel malformation or regression; it may also prevent revascularization, healing and regeneration thereby contributing to ischaemic heart disease or preeclampsia. Id. To date, it has been reported that in Western nations, at least 184 million patients could benefit from some form of anti-angiogenesis therapy, while at least 314 million patients would benefit from some form of angiogenesis-stimulating therapy (http://www.angio.org/understanding/content_understanding.html (last retrieved May 16, 2006)).

Although a great deal of effort has been undertaken to develop therapies to promote revascularization of ischemic tissue or to inhibit angiogenesis in cancer and ocular, joint or skin disorders, toxicities and acquired resistance associated with currently available therapeutics indicate that continued efforts to develop novel strategies for treating angiogenesis-associated conditions are needed.

SUMMARY OF THE INVENTION

The present invention involves the discovery that a reduction of the expression and/or activity the α subunit of an heterotrimeric GDP/GTP-binding protein that functions as a cellular signal transducer, herein "G protein," results in a reduction of tumor growth as well as angiogenesis. Thus, the invention provides angiogenesis-modulating agents that can reduce the expression of a G protein, as well as cells and compositions that contain one or more agents that can reduce or enhance the expression and/or activity of a G protein. The invention also provides methods for reducing or increasing expression and/or activity of a G protein, methods for reducing angiogenesis, and methods for promoting angiogenesis in a mammal. In addition, the invention provides methods of screening for anti-angiogenesis and anti-cancer agents, as well as methods of screening for agents that promote angiogenesis.

The invention provides an oligonucleotide that is capable of hybridizing to a nucleic acid encoding a $G\alpha_{12}$ or $G\alpha_{13}$ polypeptide under intracellular conditions and reducing expression of the nucleic acid in a cell. In some embodiments, the oligonucleotide hybridizes under intracellular conditions to a nucleic acid comprising a sequence that encodes a polypeptide having the sequence of SEQ ID NO: 2 or 4 or a polypeptide having a sequence substantially homologous to SEQ ID NO: 2 or 4. In some embodiments, the oligonucleotide hybridizes under intracellular conditions to a nucleic acid comprising SEQ ID NO: 1, 3, and/or the complement of SEQ ID NO: 1 or 3. Thus, in some embodiments, the nucleic acid encoding the $G\alpha_{12}$ or $G\alpha_{13}$ polypeptide comprises SEQ ID NO: 1 or 3, or the $G\alpha_{12}$ or $G\alpha_{13}$ polypeptide comprises SEQ ID NO: 2 or 4.

In some embodiments, the oligonucleotide is an antisense molecule capable of hybridizing to a nucleic acid encoding the $G\alpha_{12}$ or $G\alpha_{13}$ polypeptide under intracellular conditions. In one embodiment, the antisense molecule has a sequence that is identical to 17 to 33 contiguous nucleotides of SEQ ID NO: 1, 3, or the complement of SEQ ID NO: 1 or 3. In one embodiment, the antisense molecule consists of 17 to 33 contiguous nucleotides of the complement of SEQ ID NO: 1 or 3. In another embodiment, the antisense molecule has the sequence of any of SEQ ID NO: 6-9 and 11-145, or their complement. The antisense molecule may consists of the sequence of any of SEQ ID NO: 6-9 and 11-145.

In some embodiments, the oligonucleotide includes one or more ribose nucleotides, deoxyribose nucleotides, modified nucleotides, or any combinations thereof.

The invention also provides an expression vector comprising an expression control sequence that is capable of directing production of an oligonucleotide, the nucleotides of which are ribose nucleotides. In some embodiments, the expression control sequence directs production of a ribose nucleic acid transcript that hybridizes under intracellular conditions to SEQ ID NO: 1, 3 and/or to the complement of SEQ ID NO: 1 or 3.

The invention also provides a cell comprising a guanine diphosphate analogue, a guanine triphosphate analogue, an oligonucleotide capable of reducing expression of a nucleic acid encoding a $G\alpha_{12}$ or $G\alpha_{13}$ polypeptide, or any combination thereof. In some embodiments, the analogue is GTP gamma S, GDP beta S, GppNHp, or GppCH2p; and/or the oligonucleotide has the sequence of SEQ ID NO: 6-9.

The invention also provides a method for producing a cell that has a guanine diphosphate analogue, a guanine triphosphate analogue, an oligonucleotide capable of reducing expression of a nucleic acid encoding a $G\alpha_{12}$ or $G\alpha_{13}$ polypeptide, or any combination thereof. The method involves contacting the cell with a guanine diphosphate analogue, a guanine triphosphate analogue, an oligonucleotide capable of reducing expression of a nucleic acid encoding a $G\alpha_{12}$ or $G\alpha_{13}$ polypeptide, or any combination thereof.

The invention also provides a composition comprising a pharmaceutically acceptable carrier and a therapeutically effective amount of an agent that reduces the expression and/or activity of $G\alpha_{12}$ or $G\alpha_{13}$. In some embodiments, the agent is a guanine diphosphate analogue, a guanine triphosphate analogue, an oligonucleotide capable of reducing expression of a nucleic acid encoding a $G\alpha_{12}$ or $G\alpha_{13}$ polypeptide, or any combination thereof.

The invention also provides a method for modulating angiogenesis in a mammal that involves modulating the expression and/or activity of $G\alpha_{12}$ or $G\alpha_{13}$ in a cell of the mammal. The method involves administering a guanine diphosphate analogue, a guanine triphosphate analogue, an inhibitory antibody or biologically active fragment thereof that binds specifically to the carboxy-terminal region of the $G\alpha_{12}$ or $G\alpha_{13}$ polypeptide, an oligonucleotide capable of reducing expression of a nucleic acid encoding a $G\alpha_{12}$ or $G\alpha_{13}$ polypeptide, or any combination thereof, in an amount effective to decrease expression and/or activity of the $G\alpha_{12}$ or $G\alpha_{13}$ polypeptide. In some embodiments, the analogue administered is GDP beta S, GppNHp, and GppCH2p; and/or the oligonucleotide administered has the sequence of SEQ ID NO: 6-9. In some embodiments, the analogue, oligonucleotide, inhibitory antibody or biologically-active fragment thereof, or any combination thereof, is administered by direct injection to a localized area.

In some embodiments, the expression and/or activity of $G\alpha_{12}$ or $G\alpha_{13}$ is decreased by about 20% to about 90%. In some embodiments, the expression and/or activity of $G\alpha_{12}$ or $G\alpha_{13}$ is decreased by about 30% to about 70%. In some embodiments, the mammal has cancer. Thus, the invention also provides a method for reducing tumor growth or growth of a cancer cell in a mammal that involves reducing the expression and/or activity of a $G\alpha_{12}$ or $G\alpha_{13}$ in the mammal. The mammal may have melanoma, lung cancer or lymphoma.

In some embodiments, methods for modulating angiogenesis in a mammal involve increasing the expression and/or activity of $G\alpha_{12}$ or $G\alpha_{13}$ in the mammal such that angiogenesis is promoted. In one embodiment, the method involves administering to the mammal a composition comprising GTP gamma S in an amount effective to increase activity of the $G\alpha_{12}$ or $G\alpha_{13}$ polypeptide. In one embodiment, the method involves administering an expression vector comprising an expression control sequence that directs production of a nucleic acid encoding a $G\alpha_{12}$ or $G\alpha_{13}$ polypeptide The invention also provides a method of screening for an angiogenesis-modulating agent that involves contacting a cell expressing $G\alpha_{12}$ or $G\alpha_{13}$ with a candidate compound, determining whether the expression and/or activity of $G\alpha_{12}$ or $G\alpha_{13}$ is reduced or increased in the cell, and identifying a candidate compound as an angiogenesis-modulating agent if the candidate compound reduces or increases the expression and/or activity of $G\alpha_{12}$ or $G\alpha_{13}$.

In some embodiments, the angiogenesis-modulating agent is an anti-angiogenesis agent or an anti-cancer agent that reduces the expression and/or activity of $G\alpha_{12}$ or $G\alpha_{13}$. In other embodiments, the angiogenesis-modulating agent is an agent that promotes angiogenesis by increasing the expression and/or activity of $G\alpha_{12}$ or $G\alpha_{13}$.

As used herein, the term "reduce" means a decrease by any amount such as, for example, by 2%, 5%, 10%, 20%, 40% or more than 40%.

As used herein, the term "increase" means an increase by any amount such as, for example, by 2%, 5%, 10%, 20%, 40% or more than 40%.

As used herein, the term "$G\alpha_{12}$" refers to a G protein having the polypeptide sequence set out in SEQ ID NO: 2 or a polypeptide having a substantially homologous sequence to SEQ ID NO: 2.

As used herein, the term "$G\alpha_{13}$" refers to a G protein having the polypeptide sequence set out in SEQ ID NO: 4 or a polypeptide having a substantially homologous sequence to SEQ ID NO: 4.

As used herein, the term "oligonucleotide" means a polymer of 3 or more ribose or deoxyribose nucleotides, which can be naturally-occurring or modified nucleotides as discussed below. Oligonucleotides include primers for nucleic acid amplification or sequencing, probes for nucleic acid detection, or inhibitory molecules for inhibition of nucleic acid expression such as an antisense molecule (antisense RNA) or a ribozyme as discussed herein.

As used herein, the term "intracellular condition" mean conditions (e.g. temperature, pH, salt concentrations) such as those existing in a cell.

As used herein, the term "nucleic acid" includes DNA molecules such as genomic DNA and cDNA, as well as RNA molecules such as mRNA. It also includes viral DNA and RNA, as well as plasmids, cosmids and other forms of expression systems such as expression cassettes. Nucleic acids may be single stranded or double stranded.

As used herein, the term "complementary" or "complement" refers to a nucleic acid or oligonucleotide that is able to bind, that is hybridize, to another nucleic acid molecule or oligonucleotide through the formation of H-bonds between nucleotides (e.g. A with T or U and G with C) to form a double stranded molecule.

As used herein, the phrase "substantially homologous," in reference to a polypeptide, means that the polypeptide sequence is largely, though not entirely homologous to another polypeptide, and retains the same functional activity as the second polypeptide. When an amino acid position in two polypeptides is occupied by identical amino acids, then they are homologous at that position. A polypeptide is substantially homologous to another polypeptide if it exhibits at least 70%, preferably 80%, more preferably 90% homology to the second polypeptide. With respect to G proteins, a polypeptide substantially homologous to a G protein will have the four highly conserve domains characteristic of all G proteins shown in FIG. 15. These four highly conserved domains include (a) a first region (open box A) that corresponds to the region in $G\alpha_{12}$ or $G\alpha_{13}$ having the sequence ILLLGAGESGKSTFLKQ (SEQ ID NO: 147); (b) a second region (open box C) having the sequence DVGGQR (SEQ ID NO: 162); (c) a third region (open box G) having the sequence LFLNKXD (SEQ ID NO: 163) where X is any amino acid; and (d) a fourth region (open box I) that corresponds to the region having the sequence TTAIDT (SEQ ID NO: 151) in $G\alpha_{12}$.

As used herein, the phrase "expression vector" means a nucleic acid molecule capable of transporting and/or allowing for the expression of another nucleic acid to which it has been linked. The product of that expression is referred to as a messenger ribose nucleic acid (mRNA) transcript. Thus, expression vectors contain appropriate expression control sequences that may direct expression of a nucleic acid that is operably linked to the expression control sequence to produce a transcript.

As used herein, the phrase "expression control sequence" means a nucleic acid sequence sufficient to direct transcription of another nucleic acid sequence that is operably linked to the expression control sequence to produce an RNA transcript when appropriate molecules such as transcriptional activator proteins are bound the expression control sequence.

As used herein, the term "operably linked" means that a nucleic acid and an expression control sequence is positioned in such a way that the expression control sequence directs expression of the nucleic acid when the appropriate molecules such as transcriptional activator proteins are bound to the expression control sequence.

As used herein, the term "antibody" means an immunoglobulin molecule and immunologically active portions thereof.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. Amino acid designations may include full name, three-letter, or single-letter designations as commonly understood by one of ordinary skill in the art to which this invention belongs. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF DRAWINGS

FIG. 11A-B depict the nucleic acid sequence of G protein Gα$_{12}$ (NM_007353).

FIG. 12 is the amino acid sequence of G protein Gα$_{12}$.

FIG. 13A-B depict the nucleic acid sequence of G protein Gα$_{13}$ (NM_006572).

FIG. 14 is the amino acid sequence of G protein Gα$_{13}$.

DETAILED DESCRIPTION

The present invention involves the discovery that a reduction of the expression and/or activity of the α subunit of an heterotrimeric GDP/GTP-binding protein that functions as a cellular signal transducer, herein "G protein," results in a reduction of angiogenesis and tumor growth. More specifically, the invention is based on the discovery that xenografted tumors failed to grow in Gα$_{13}$$^{+/-}$ and in Gα$_{12}$$^{-/-}$ mice, as well as the discovery that Gα$_{13}$$^{+/-}$ mice showed impaired tumor vascularization. Thus, the invention provides angiogenesis-modulating agents that reduce the expression and/or activity of a G protein, as well as agents that increase their expression and/or activity. The invention also provides methods for reducing or increasing expression and/or activity of a G protein, methods for reducing angiogenesis and/or tumor growth in a mammal, and methods for promoting angiogenesis in a mammal. In addition, the invention provides methods of screening for anti-angiogenesis and anti-cancer agents, as well as methods of screening for agents that promote angiogenesis.

Agents of the Invention

Figure 15:
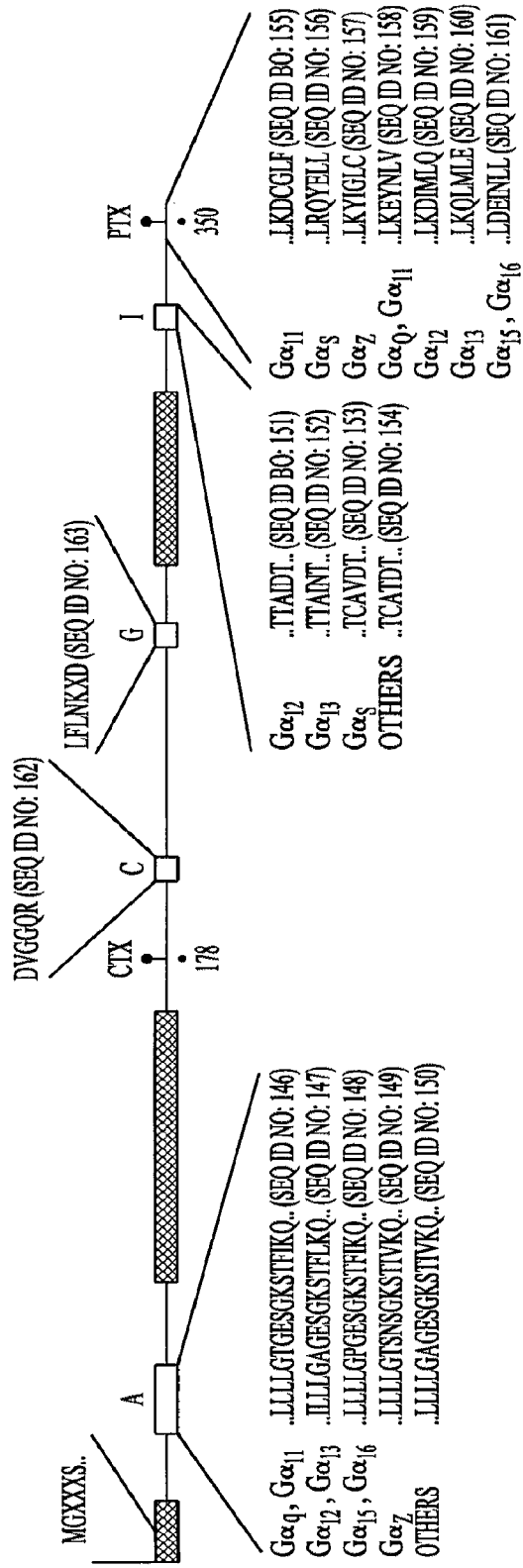
FIG. 15 is a schematic diagram illustrating the various domains in the α subunit of an heterotrimeric GDP/GTP-binding protein. Regions of highest amino acid sequence diversity are indicated by hatched boxes. Regions of highly conserved domains found in all G proteins and thought to be directly involved in interaction with the guanine nucleotide are indicated by clear boxes (A, C, G, and I). The single letter amino acid code is used to show the distinctive sequences for some of the Gα subunits. See Simon et al., Science 252:802 (1991).

The invention provides an angiogenesis-modulating agent that can reduce or increase expression and/or activity of a G protein. As used herein, the term "G protein" refers to the α subunit of an heterotrimeric GDP/GTP-binding protein having α, β and γ subunits that functions as a cellular signal transducer. Heterotrimeric GDP/GTP-binding proteins relay signals from transmembrane receptors such as G protein-coupled receptors (GPCRs) to downstream effectors. More specifically, interaction of a heterotrimeric GDP/GTP binding protein with its ligand-activated receptor promotes exchange of a guanosine diphosphate (GDP), bound to the α subunit, for guanosine triphosphate (GTP) and the subsequent dissociation of the α-GTP complex from the βγ heterodimer. A G protein may be from any source, for example, from a mouse, a rabbit, a pig, a dog, a cow, a monkey, or a human. A G protein may be identified based on sequence and function. Simon et al., Science 252:802 (1991). For example, a G protein has the four highly conserved domains as illustrated in FIG. 15 (SEQ ID NO: 146-163). G proteins may also be grouped into families, e.g. $G_s$, $G_i$, $G_q$ and $G_{12}$, based on their amino acid sequences. See, for example, Simon et al., Science 252:802 (1991). Examples of G proteins of the invention include Gα$_{12}$ and Gα$_{13}$, as well as any polypeptide that is substantially homologous to Gα$_{12}$ or Gα$_{13}$, that is, it has the four highly conserved domains characteristic of G proteins illustrated in FIG. 15 and at least 70% amino acid sequence homology with Gα$_{12}$ or Gα$_{13}$. The term "G protein" also includes any biologically active fragment of the full-length polypeptide.

An agent that can reduce or increase the expression and/or activity of a G protein may decrease or increase its expression and/or activity by any amount such as, for example, by 2%, 5%, 10%, 20%, 40% or more than 40%.

In one embodiment, an agent of the invention may be an oligonucleotide that will hybridize to a G protein nucleic acid under intracellular or stringent conditions. The oligonucleotide is capable of reducing expression of a nucleic acid encoding the G protein. A nucleic acid encoding a G protein may be genomic DNA as well as messenger RNA. It may be incorporated into a plasmid vector or viral DNA. It may be single strand or double strand, circular or linear. Examples of nucleic acids encoding G proteins are set forth in SEQ ID NO. 1 and 3. See FIGS. 11A-B and 13A-B. G protein nucleic acids may also be a fragment of the sequences set forth in SEQ ID NO: 1 and 3 provided that the nucleic acids encode a biologically active polypeptide.

An oligonucleotide is a polymer of ribose nucleotides or deoxyribose nucleotides having more than 3 nucleotides in length. An oligonucleotide may include naturally-occurring nucleotides; synthetic, modified, or pseudo-nucleotides such as phosphorothiolates; as well as nucleotides having a detectable label such as $P^{32}$, biotin or digoxigenin. An oligonucleotide that can reduce the expression and/or activity of a G protein nucleic acid, that is an oligonucleotide of the invention, may be completely complementary to the G protein nucleic acid. Alternatively, some variability between the sequences may be permitted. An oligonucleotide that can hybridize to a G protein nucleic acid under intracellular conditions or under stringent hybridization conditions, is sufficiently complementary to inhibit expression of a G protein nucleic acid. Intracellular conditions refer to conditions such as temperature, pH and salt concentrations typically found inside a cell, e.g. a mammalian cell. One example of such a mammalian cell is the MEF cell described below or an endothelial, smooth muscle or neuronal cell. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory oligonucleotides that comprise, for example, 2, 3, 4, or 5 or more stretches of contiguous nucleotides that are precisely complementary to a G protein coding sequence, each separated by a stretch of contiguous nucleotides that are not complementary to adjacent coding sequences, may inhibit the function of a G protein nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an oligonucleotide hybridized to a sense nucleic acid to estimate the degree of mismatching that will be tolerated for inhibiting expression of a particular target nucleic acid. Oligonucleotides of the invention include, for example, a ribozyme or an antisense nucleic acid molecules.

The antisense nucleic acid molecule may be single or double stranded (e.g. a small interfering RNA (siRNA)), and may function in an enzyme-dependent manner or by steric blocking. Antisense molecules that function in an enzyme-dependent manner include forms dependent on RNase H activity to degrade target mRNA. These include single-stranded DNA, RNA, and phosphorothioate molecules, as well as the double-stranded RNAi/siRNA system that involves target mRNA recognition through sense-antisense strand pairing followed by degradation of the target mRNA by the RNA-induced silencing complex. Steric blocking antisense, which are RNase-H independent, interferes with gene expression or other mRNA-dependent cellular processes by binding to a target mRNA and getting in the way of other processes. Steric blocking antisense includes 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce G protein translation such that the level of G protein polypeptide is reduced. SiRNAs mediate post-transcriptional gene silencing in a sequence-specific manner. See, for example, http://www.ambion.com/techlib/hottopics/rnai/rnai_may2002_print.html (last retrieved May 10, 2006). Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the G protein mRNA transcript. The region of homology may be 30 nucleotides or less in length, preferable less than 25 nucleotides, and more preferably about 21 to 23 nucleotides in length. SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003). Typically, a target site that begin with AA, have 3' UU overhangs for both the sense and antisense siRNA strands, and have an approximate 50% G/C content is selected. SiRNAs may be chemically synthesized, created by in vitro transcription, or expressed from an siRNA expression vector or a PCR expression cassette. See, e.g., http://www.ambion.com/techlib/tb/tb_506html (last retrieved May 10, 2006). When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, preferably, 3 to 23 nucleotides in length, and may be of various nucleotide sequences including, AUG, CCC, UUCG, CCACC, CTCGAG, AAGCUU, CCACACC and UUCAAGAGA (SEQ ID NO: 10). SiRNAs also may be produced in vivo by cleavage of double-stranded RNA introduced directly or via a transgene or virus. Amplification by an RNA-dependent RNA polymerase may occur in some organisms.

Examples of siRNA sequences that can hybridize to a G protein $G\alpha_{12}$ nucleic acid include the following sequences and their complementary sequences:

| SEQ ID NO. | Pos | siRNA Sequence |
|---|---|---|
| 11 | 3491 | AAGCAUGAGAGGAAGGAGAUAUU |
| 12 | 789 | AAGGGAAUUGUGGAGCAUGACUU |
| 13 | 1479 | AAGGACAUGGAAACUGUCACGUU |
| 14 | 1573 | AAUCACACAGCUUGCUUUGCUUU |
| 15 | 4242 | AAUGGUAGUGGUCCGGGUCAGUU |
| 16 | 2224 | AAGUCAUCUGCUCACACACAGUU |
| 17 | 1758 | AAAGCUUUGCCUAACAGUAGCUU |
| 18 | 2874 | AAACCCGGUAAACGCAAGCCCUU |
| 19 | 4333 | CAGCCUCUGAAUGUUUAUUAAAA |
| 20 | 665 | CAGCCGGAGAAGCGAGUUUCAGC |
| 21 | 3004 | GAGGCUGUGUGUCAGUGUUUGCU |
| 22 | 723 | GACCGGAUCGGCCAGCUGAAUUA |
| 23 | 3877 | GAGGUAGUUGUGCCUCAAUUAUU |
| 24 | 2340 | CAGCUGCUUGGCGAGCUAACAGC |
| 25 | 365 | GAGCGGCAAGUCCACGUUCCUCA |
| 26 | 1660 | UACACACGCUCUGUCUUUAAUGA |
| 27 | 470 | CAAGGGCUCAAGGGUUCUUGUUG |
| 28 | 626 | GAGCGCACUCUGGAGGGAUUCUG |
| 29 | 1217 | CACCGCCAUCGACACCGAGAACG |
| 30 | 3229 | GAGCGUGGUGAGCUUUGUUUGCC |
| 31 | 2559 | GAGCCUGUGAAUGUUGAUACGAG |
| 32 | 4226 | CAGAGGCUCCCAUUGGAAUGGUA |
| 33 | 4039 | GAGUCAUAGGUCUGUAAUUUAUA |

| SEQ ID NO. | Pos | siRNA Sequence |
|---|---|---|
| 34 | 801 | GAGCAUGACUUCGUUAUUAAGAA |
| 35 | 3874 | CAGGAGGUAGUUGUGCCUCAAUU |
| 36 | 1633 | GAGGACCGUGUUGUGUGUAUG |
| 37 | 2167 | CAACGGCAAAGACACAGAAACCA |
| 38 | 1454 | CAGCCAGCCAGCGAGCUCUAGGC |
| 39 | 966 | AACCGGCUGGUGGAGUCCAUGAA |
| 40 | 1636 | GACCGUGUUGUGUGUAUGUGU |
| 41 | 4276 | AAGCUUUGCACAGUGUAUUAACA |
| 42 | 275 | GAGGCGUAGCCGCGACAUCGACG |
| 43 | 2002 | CAGGUGUGGAUUCACCUUACGCC |
| 44 | 1662 | CACACGCUCUGUCUUUAAUGACA |
| 45 | 2249 | CAGCACAUAGCGUUUCCUUCUUU |
| 46 | 2382 | CAGACGCUGGAGGAAUCUUGAGU |
| 47 | 3297 | GAGCCCAGAGGAAGUGCAAGCGG |
| 48 | 3494 | CAUGAGAGGAAGGAGAUAUUGUG |
| 49 | 1080 | AAGACCGUGAGCAUCAAGAAGCA |
| 50 | 1194 | AAGCCACUCUUCCACCACUUCAC |
| 51 | 735 | CAGCUGAAUUACUUUCCUAGUAA |
| 52 | 3111 | GACCGGAGAUGAGUGCCGAUGAC |
| 53 | 4275 | UAAGCUUUGCACAGUGUAUUAAC |
| 54 | 2151 | CACCCACUGCCCAACCCAACGGC |
| 55 | 864 | CAGCGCCAGAAGUGGUUCCAGUG |
| 56 | 1795 | CACGCCGAUGCUGCUAAACUCAG |
| 57 | 2168 | AACGGCAAAGACACAGAAACCAG |
| 58 | 3417 | UAGUCCGGCCUUGUCAAUGAGUG |
| 59 | 996 | GAGACCAUCGUCAACAACAAGCU |
| 60 | 1994 | GAGCUCUGCAGGUGUGGAUUCAC |
| 61 | 2058 | CAUGCCCAGCAGCACAACACGGA |
| 62 | 896 | GAUCACGUCCAUCCUGUUCAUGG |
| 63 | 1079 | GAAGACCGUGAGCAUCAAGAAGC |
| 64 | 3295 | CAGAGCCCAGAGGAAGUGCAAGC |
| 65 | 780 | AAAGCCACCAAGGGAAUUGUGGA |
| 66 | 3605 | GAGGCACUUGGCCUUGCUGAGCU |
| 67 | 3933 | GAUCUGUUCCUCAUAGCUAUACU |
| 68 | 4221 | UAAGGCAGAGGCUCCCAUUGGAA |

| SEQ ID No. | Pos | siRNA Sequence |
|---|---|---|
| 69 | 4629 | AAGGCUAAAUAUCAGUGUUAAUU |
| 70 | 602 | AACUUGGAGAACCAGAUUAUAUU |
| 71 | 4302 | AAUACCAUAUGUCCUUAUCAUUU |
| 72 | 2004 | AAGCAACUUGGUAACAGAACUUU |
| 73 | 3206 | AAAGAGGACACUUCAUCUUACUU |
| 74 | 2102 | AAUCCUUACUGUAGGAAAUCAUU |
| 75 | 665 | AAGGCAUCCAUGAAUACGACUUU |
| 76 | 3387 | AAUGUCUCAGAAUCAACAUUCUU |
| 77 | 3327 | AAACACCAAAUAGAUAUCAUGUU |
| 78 | 741 | AAGGAAACGUUGGUUUGAAUGUU |
| 79 | 1258 | AAUAGCAGUUUACAACCAGAAUU |
| 80 | 2300 | AACAGAUACAGUAUGUAUACAUU |
| 81 | 664 | AAAGGCAUCCAUGAAUACGACUU |
| 82 | 901 | AAUGUCUCCAUAAUUCUGUUCUU |
| 83 | 4301 | AAAUACCAUAUGUCCUUAUCAUU |
| 84 | 1900 | AACGUAACGAGUGAAAUAGAAUU |
| 85 | 2591 | AAGUCCAAGGCUGGCGACAGCUU |
| 86 | 2949 | AAGUUCAUGGUAUCGUGCAUGUU |
| 87 | 3821 | AAUAUCACACAAGUGUCUUCAUU |
| 88 | 957 | AAUUGUGAGCAUCAAAGACUAUU |
| 89 | 455 | AAGGAAUGGUGGAAACAAGGGUU |
| 90 | 2466 | AAAUGUGUCCACGAAGUAGCUUU |
| 91 | 1870 | AAGCUAAUGCUGUUUACCGUGUU |
| 92 | 1630 | AACUUUAUGGUGACCUCCUAUUU |
| 93 | 1679 | AAGAAAUGGCAUUCUGUAGGUUU |
| 94 | 827 | AAGAUCGACUGACCAAUCGCCUU |
| 95 | 873 | AACAAUCGUCAAUAACCGGGUUU |
| 96 | 1378 | AAGAUUUGCUGUAAUGCAGGCUU |
| 97 | 872 | AAACAAUCGUCAAUAACCGGGUU |
| 98 | 1683 | AAUGGCAUUCUGUAGGUUUAUAG |
| 99 | 1549 | UAGGGAUGAGGUUAGGAAUAUUC |
| 100 | 4253 | GAUCGCCUUAAUACCAGAAAUGA |
| 101 | 4683 | AAGCCCAAACAUUUGUAACAAAC |
| 102 | 1462 | UAGGCAUAUUUCAGGCUUUAAAU |
| 103 | 1656 | AAGGGCUGUUAGAAGUUCUAUCU |
| 104 | 541 | GACCGGCGUCGAGAAUUUCAACU |
| 105 | 4420 | CAUCCGAUUAUGCCUUAUUUAUA |
| 106 | 722 | UAGGUGGUCAGAGAUCAGAAAGG |
| 107 | 2597 | AAGGCUGGCGACAGCUUGAAAAG |

Examples of siRNA that can hybridize to a G protein $G\alpha_{13}$ nucleic acid include the following sequences and their complementary sequences:

-continued

| SEQ ID No. | Pos | siRNA Sequence |
|---|---|---|
| 108 | 449 | CAGCCCAAGGAAUGGUGGAAACA |
| 109 | 4618 | UAUGUCAUGAGAAGGCUAAAUAU |
| 110 | 228 | GAGCGGCAAGUCCACCUUCCUGA |
| 111 | 3795 | AAUGCCUUCUCAUUUAAUUCUGA |
| 112 | 1865 | AAGGCAAGCUAAUGCUGUUUACC |
| 113 | 4682 | AAAGCCCAAACAUUUGUAACAAA |
| 114 | 1371 | CAUCGCCAAGAUUUGCUGUAAUG |
| 115 | 1655 | UAAGGGCUGUUAGAAGUUCUAUC |
| 116 | 509 | UAUGGGCAGACAGCGGCAUACAG |
| 117 | 2174 | AACUCCACACUGUGCCAUUUGUG |
| 118 | 811 | GACCAGGUGCUUAUGGAAGAUCG |
| 119 | 4673 | CAUGCCUGUAAAGCCCAAACAUU |
| 120 | 3069 | AAUUGCAGUGCUAAUGAAUAUCG |
| 121 | 3309 | UACCACCAAGAAGUGUUGAAACA |
| 122 | 3207 | AAGAGGACACUUCAUCUUACUUA |
| 123 | 124 | GAGGCCGAGCAGCAACGCAAGUC |
| 124 | 142 | AAGUCCAAGGAGAUCGACAAAUG |
| 125 | 1072 | AAGCCCUUAUACCACCACUUCAC |
| 126 | 1703 | UAGAAGGUUUAGCCUUCAUAUUU |
| 127 | 1845 | CAGGUGGUAUGGGAGAGCAAAAG |
| 128 | 4505 | AACCCUCAAAUUGGUGCUUUCAU |
| 129 | 4130 | UAAGGUGUAUUGGCAUGUAAUUU |
| 130 | 1682 | AAAUGGCAUUCUGUAGGUUUAUA |
| 131 | 2596 | CAAGGCUGGCGACAGCUUGAAAA |
| 132 | 355 | GAUGCUCGAGAGAAGCUUCAUAU |
| 133 | 2491 | GAUCGCAGAUACAUUCAUAGUGA |
| 134 | 3209 | GAGGACACUUCAUCUUACUUAAG |
| 135 | 3127 | GAGAGUUUACCCAUACAUUUAGC |
| 136 | 3318 | GAAGUGUUGAAACACCAAAUAGA |
| 137 | 3639 | AAGGUGCUCAUAAUUUCACUAUG |
| 138 | 4628 | GAAGGCUAAAUAUCAGUGUUAAU |
| 139 | 3063 | UAGCAUAAUUGCAGUGCUAAUGA |
| 140 | 2557 | UAGGCUGUAUGUAGUGCUACAAU |
| 141 | 3276 | AAGCAGAAAUCACCAAGUUUCCC |
| 142 | 2078 | UAUCUCAGUUGGUCAGUAAAGAC |
| 143 | 1529 | AAGGUGUCCUUAAAUACUUGUAG |
| 144 | 3794 | GAAUGCCUUCUCAUUUAAUUCUG |
| 145 | 971 | AAGACUAUUUCCUAGAAUUUGAA |

An antisense oligonucleotide may also be used to specifically reduce G protein expression, for example, by inhibiting transcription and/or translation. An antisense oligonucleotide is complementary to a sense nucleic acid encoding a G protein. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a G protein. The non-coding region includes the 5' and 3' regions that flank the coding region, for example, the 5' and 3' untranslated sequences. An antisense oligonucleotide is generally at least six nucleotides in length, but may be about 8, 12, 15, 20, 25, 30, 35, 40, 45, or 50 nucleotides long. Longer oligonucleotides may also be used. An antisense oligonucleotide may be prepared using methods known in the art, for example, by expression from an expression vector encoding the antisense oligonucleotide or from an expression cassette. Alternatively, it may be prepared by chemical synthesis using naturally-occurring nucleotides, modified nucleotides or any combinations thereof. In some embodiments, the oligonucleotides are made from modified nucleotides or non-phosphodiester bonds, for example, that are designed to increase biological stability of the oligonucleotide or to increase intracellular stability of the duplex formed between the antisense oligonucleotide and the sense nucleic acid. Naturally-occurring nucleotides include the ribose or deoxyribose nucleotides adenosine, guanine, cytosine, thymine and uracil. Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl)uracil, (acp3) w, and 2,6-diaminopurine. Thus, oligonucleotides of the invention may include modified nucleotides, as well as natural nucleotides such as combinations of ribose and deoxyribose nucleotides, and an antisense oligonucleotide of the invention may be of any length discussed above and that is complementary SEQ ID NO: 1, 3 and 5.

An angiogenesis-modulating agent of the invention may also be a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave a G protein mRNA transcript and thereby inhibit translation of the mRNA. See, for example, Haseloff et al., U.S. Pat. No. 5,641,673. A ribozyme having specificity for a G protein nucleic acid may be designed based on the nucleotide sequence of SEQ ID NO: 1 and 2. Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a nucleotide sequence having SEQ ID NO:1 or 2. Longer complementary sequences may be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a G protein of the invention by modifying the hybridization region of the ribozyme to include a sequence that is complementary to the target G protein. Alternatively, an mRNA encoding a G protein may be used to select a catalytic RNA having a specific ribonuclease activity from a pool of RNA molecules. See, for example, Bartel & Szostak, Science 261:1411-1418 (1993).

An agent of the invention may also be an analogue of GDP and/or GTP. The analogue may be an activator or an inhibitor of G protein function. Non-limiting examples of a GDP and/or GTP analogue include 8-bromoguanosine 5'-triphosphate; 3,4-diaminobenzophenone(DABP)-phosphoramidate-GTP; guanosine-5'-O-(3-thiotriphosphate (GTP gamma S); Gpp-NHp; GppCH2p; GDP-beta S; 8-aza-7-deazaguanine; 6-thioguanine; GMP-PNP; and 8-oxo-guanine.

Thus, agents of the invention include those that will reduce as well as enhance angiogenesis and may be an oligonucleotide, a G protein nucleic acid, and an activating or inhibitory GTP and/or GDP analogue. An oligonucleotide may reduce G protein expression and activity, while an inhibitory GDP and/or GTP analogue may reduce G protein function. Similarly, a G protein nucleic acid, e.g. one incorporated into an expression vector and operably-linked to an expression control sequence, may increase G protein expression and activity, while an activating GDP and/or GTP analogue such as GTP gamma S may increase G protein function.

Pharmaceutical Compositions

Agents of the invention may be incorporated into a pharmaceutical composition suitable for administration to a mammal. A pharmaceutical composition of the invention typically comprises the active agent and a pharmaceutically acceptable carrier. As used herein, the phrase "pharmaceutically acceptable carrier" means any and all solvents, dispersion media, coatings, antibacterial and antifungal agents, isotonic and absorption delaying agents, and the like known in the art to be compatible with pharmaceutical administration to a mammal. Except insofar as any conventional media or agent is incompatible with the active compound, use thereof in the pharmaceutical composition of the invention is contemplated. In addition, supplementary active compounds may also be included into the pharmaceutical compositions.

A pharmaceutical composition of the invention is formulated to be compatible with the intended route of administration. Examples of routes of administration include parenteral, intravenous, intradermal, subcutaneous, oral, by inhalation, transdermal (topical), transmucosal, and rectal administration. Solutions or suspensions used for parenteral, intradermal or subcutaneous application may include (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates and agents for the adjustment of tonicity such as sodium chloride or dextrose. pH may be adjusted with acids or bases, such as hydrochloric acid or sodium hydroxide. The parenteral preparation may be enclosed in ampoules, disposable syringes or multiple dose vials.

Pharmaceutical compositions suitable for injection include sterile aqueous solutions or dispersions and sterile powders for extemporaneous preparation of sterile injectable solutions or dispersions. For intravenous administration, suitable carriers include physiological saline, bacteriostatic water, or phosphate buffered saline. Compositions must be sterile and be stable under the conditions of manufacture and storage and must be preserved against contamination by microorganisms such as bacteria and fungi. The carrier may be a solvent or dispersion medium containing, for example, water, ethanol, polyol (e.g. glycerol, propylene glycol and liquid polyethylene glycol), and suitable mixtures thereof. The proper fluidity may be achieved, for example, by using a coating such as lecithin, by maintaining the required particle size in the case of dispersion and by using surfactants. Prevention of the action of microorganisms may be achieved using various antibacterial and antifungal agents such as, for example, parabens, chlorobutanol, phenol, ascorbic acid, and thimerosal. Other ingredients such as an isotonic agent or an agent that delays absorption (e.g. aluminum monostearate and gelatin) may be included.

Sterile injectable solutions may be prepared by incorporating the active agent in the required amount in an appropriate solvent with one or a combination of ingredients discussed above, as required, followed by filtered sterilization. Dispersions may be prepared by incorporating the active compound into a sterile vehicle that contains a basic dispersion medium and other required ingredients discussed above. In the case of sterile powders for the preparation of injectable solutions, the preferred methods of preparation include vacuum drying and freeze-drying which yield a powder of the active ingredient and any additional desired ingredient from a previously sterile-filtered solution.

Oral compositions may include an inert diluent or an edible carrier. They may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier. Pharmaceutically compatible binding agents and/or adjuvant materials may be included as part of the composition. The tablets, pills, capsules, troches and the like may contain any of the following ingredients or compound of a similar nature: a binder such as microcrystalline cellulose, gum tragacanth or gelatin; an excipient such as starch or lactose; a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate or orange flavoring.

For administration by inhalation, the composition may be delivered in the form of an aerosol spray from a pressurized container or dispenser which contains a suitable propellant, for example, a gas such as carbon dioxide or a nebulizer.

Systemic administration may also be by transmucosal or transdermal means. For transmucosal or transdermal administration, penetrants known in the art to be appropriate to the barrier to be permeated may be used. These include detergents, bile salts and fusidic acid derivatives for transmucosal administrations, which may be accomplished using nasal sprays, for example. For transdermal administration, the active compounds are formulated into ointments, salves, gels or creams as generally known in the art.

In one embodiment, the agents of the invention may be prepared with carriers that will protect the agent against rapid elimination from the body, such as a controlled release formulation such as implants and microencapsulated delivery systems. Biodegradable biocompatible polymers may be used. These include ethylene vinyl acetate, polyanhydrides, polyglycolic acid, collagen, polyorthoesters, and polylactic acid. Methods for preparation of such formulations will be apparent to those skilled in the art. Liposomal suspensions, including those targeted to infected cells with monoclonal antibodies to viral antigens may also be used as pharmaceutically acceptable carriers. These may be prepared using methods known in the art.

Oral or parenteral compositions may be formulated in dosage unit form for ease of administration and uniformity of dosage. The phrase "dosage unit form" refers to physically discrete units suited as unitary dosages for the subject to be treated, each unit containing a predetermined quantity of active compound calculated to produce the desired therapeutic effect in association with the required pharmaceutical carrier. The specification for the dosage unit forms is dependent on the unique characteristics of the active compound and the particular therapeutic effect to be achieved.

The oligonucleotides of the invention may be inserted into vectors and used as gene therapy vectors, which may be delivered to a subject by intravenous injection, local administration or by stereotactic injection. See, for example, U.S. Pat. No. 5,328,470 and Chen et al., PNAS 91:3054 (1994). The pharmaceutical preparation of the gene therapy vector may include the gene therapy vector in an acceptable diluent or may comprise a slow release matrix in which the gene delivery vehicle is imbedded. Thus, the oligonucleotide of the invention may be administered to a subject by direct injection at a tissue site or generated in situ. Alternatively, it may be modified to target selected cells and then administered systemically. For example, antisense molecules may be modified such that they bind to receptors or antigens expressed on a selected cell surface.

The pharmaceutical compositions may be included in a container, pack or dispenser together with instructions for administration. Therefore, the invention also provides an article of manufacture comprising a pharmaceutical composition of the invention and instructions for use of the composition for the treatment of conditions associated with excessive, insufficient or aberrant angiogenesis or for the treatment of conditions in which an increase or decrease of angiogenesis would have therapeutic effects. Conditions for which an agent of the invention would be useful are discussed in the following section.

The dosage to be administered to the mammal may be any amount appropriate to reduce or promote G protein expression. The dosage may be an effective dose or an appropriate fraction thereof. This will depend on individual patient parameters including age, physical condition, size, weight, the condition being treated, the severity of the condition, and any concurrent treatment. Factors that determine appropriate dosages are well known to those of ordinary skill in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and/or pharmacodynamic models. The precise amount to be administered to a patient will be the responsibility of the attendant physician. However, that a patient may insist upon a lower dose or tolerable dose for medical reasons, psychological reasons or for virtually any other reasons.

Agents of the invention such as a GDP or GTP analogue may be administered orally or by injection at a dose of from 0.1 to 2000 mg/kg weight of the mammal, preferable from 1 to 200 mg/kg weight of the mammal. An oligonucleotide of the invention may be administered orally or by injection at a dose of from 0.05 to 500 mg per kg weight of the mammal, preferably 0.5 to 50 mg/kg weight of the mammal. The dose range for adult humans is generally from 4 to 40,000 mg/day and preferably 40 to 4,000 mg/day. As certain agents of the invention are long acting, it may be advantageous to administer an initial dose of 80 to 4,000 mg the first day then a lower dose of 20 to 1,000 mg on subsequent days.

Methods of Use

An agent or a pharmaceutical composition of the invention may be used to reduce or promote G protein expression and/or activity in a mammal. For example, an oligonucleotide may be used to reduce G protein expression and activity, while an inhibitory GDP or GTP analogue may be used to reduce G protein function. Similarly, a G protein nucleic acid, e.g. one incorporated into an expression vector and operably-linked to an expression control sequence, may be used to increase G protein expression and activity, while an activating GDP or GTP analogue such as GTP gamma S may be used to increase G protein function.

A mammal may be a mouse, a rabbit, a monkey, a cow, a pig, or a human. An agent or composition of the invention may be administered to a mammal exhibiting a disease or condition associated with G protein expression or a mammal at risk for developing such a condition.

The disease or condition may be one associated with excessive, insufficient or otherwise abnormal angiogenesis or a condition associated with angiogenesis such that the modulation of angiogenesis provides a therapeutic benefit. Non-limiting examples of such conditions include cancers such as melanoma, lymphoma, cancer of the lung, breast, colon, kidney, pancreas, bone, and brain, as well as cancer metastasis; infectious diseases such as Orf, HPV, HIV infections; autoimmune disorders such as systemic sclerosis, multiple sclerosis, Sjogren's disease; vascular malformations; transplant arteriopathy and atherosclerosis; obesity; skin disorders such as psoriasis, allergic dermatitis, Kaposi's sarcoma in AIDS patients and systemic sclerosis; eye diseases such as diabetic retinopathy; retinopathy of prematurity and persistent hyperplastic vitreous syndrome; gastrointestinal tract diseases such as inflammatory bowel disease, periodontal disease and liver cirrhosis; reproductive system diseases such as endometriosis and ovarian cysts or hyperstimulation; bone or joint diseases such as arthritis and synovitis and HIV-induced bone marrow angiogenesis; and kidney disease such as diabetic nephropathy. See, for example, Carmeliet, Nature 438: 932-936, Supplementary Table 1 (2005). Non-limiting examples of conditions related to insufficient angiogenesis include Alzheimer's disease; stroke; diabetes; hypertension; hair loss; preeclampsia; lupus; neonatal respiratory distress syndrome; ischemic heart disease, osteoporosis and nephropathy. See, for example, Carmeliet, Nature 438: 932-936; Supplementary Table 2 (2005). An agent of the invention may be used prophylactically, for example, administration may occur prior to the onset of symptoms related to the disease or condition. Alternatively, an agent or composition of the invention may be used to treat an existing condition, for example, to reduce or prevent growth of a tumor or cancer cell and/or prevent tumor metastasis. An agent or composition of the invention may be administered in an appropriate route as discussed earlier.

An oligonucleotide of the invention may also be used as an hybridization probe to determine the level of expression of a G protein in a sample. Methods of hybridization using oligonucleotides, for example, Northern hybridization or in situ hybridization, are known in the art.

Screening Methods

In one embodiment, the invention provides a method for screening for an anti-cancer, an anti-angiogenesis agent, or an agent that promotes angiogenesis. The anti-cancer or anti-angiogenesis agent or the agent that promotes angiogenesis may be a peptide, a peptidomimetic, a small molecule or the like that reduces or promotes the expression and/or activity of a G protein.

The screening method may be a cell-based assay in which a cell that expresses a G protein is contacted with a test compound, and the level of G protein expression is determined. G protein expression may be determined by examining the level of transcription or translation using methods known in the art. For example, the level of G protein transcript may be determined by Northern or in situ hybridization using an oligonucleotide that would hybridize to the G protein transcript under stringent condition. Stringent conditions refer to conditions for hybridization and washing under which nucleotide sequences at least 60%, for example 65%, 70%, 75% or more than 75% identical to each other typically remain hybridized to each other. Such stringent conditions are known to those skilled in the art and can be found in *Current Protocols in Molecular Biology*, John Wiley & Sons, N.Y. (1989). A preferred non-limiting example of stringent hybridization conditions are hybridization in 6× sodium chloride/sodium citrate (SSC) at about 45° C., followed by one or more washes in 0.2×SSC, 0.1% SDS at 50-65° C. Alternatively, the level of G protein translation may be determined using a G protein-specific antibody in methods known in the art such as Western hybridization or immuno-precipitation. The level of G protein expression in a cell that has been contacted with the test compound is compared to the level of G protein expression in a control cell that has not been contacted with the test compound. An anti-cancer or anti-angiogenesis agent is one that reduces expression of a G protein in the cell, while an angiogenesis promoting agent is one that increases expression of a G protein in a cell.

The screening method may also be a cell-free assay in which a purified or partially-purified preparation containing a G protein is contacted with a test compound, and then the activity of the G protein is determined. G protein activity assay is known in the art. See, for example, Jiang, et al., Nature 395: 808-813 (1998).

The screening method may also be an in vivo assay in which an animal injected with tumor cells is administered a test compound and then angiogenesis, tumor growth or the level of G protein expression or activity, is assessed using methods known in the art. See, e.g., Examples 1, 7, and 8 described herein. In each case, a test compound is an anti-angiogenesis or anti-cancer agent if it reduces G protein expression and/or activity or if it reduces tumor growth and/or angiogenesis.

In another aspect, the invention provides a method for screening for a compound that promotes angiogenesis. In methods for screening for a compound that promotes angiogenesis, similar cell-based, cell-free or in vivo assays such as those described above may be employed. A test compound that increase G protein expression and/or activity is one that promotes angiogenesis.

The invention will be further described in the following examples, which do not limit the scope of the invention described in the claims.

EXAMPLES

Example 1

Materials and Methods

Plasmid Constructs: Wild-type and mutant genes encoding human $G\alpha_{12}$, $G\alpha_{13}$, and Rac cloned in pcDNA3.1 were obtained from Guthrie Research Center. Several $G\alpha_{13}$ C-terminal mutants were made. One C-terminal mutant was a truncated protein lacking the last five amino acid residues QLMLQ. A second C-terminal mutant was a similarly truncated protein fused to a Myc tag and a $His_6$ tag at its C-terminus (EQKLISGGDLNMHTEHHHHHH (SEQ ID NO: 5). This Myc/$His_6$ fusion protein was generated by subcloning and expression from a pcDNA3.1-myc-His vector. The third $G\alpha_{13}$ mutant had a TAP tag at the C-terminus. Rigaut et al., Nat Biotechnol 17: 1030-1032 (1999). The TAP tag has 184 amino acid residues including a calmodulin-binding peptide, a TEV cleavage site and two IgG binding domains of protein A. The $G\alpha_{13/i}$-DD1 chimera (in pET28a) was made based on the $G\alpha_{13/i}$-5 chimera (Chen et al., Nat Struct Mol Biol 12: 191-197 (2005)) with the following sequences: amino acid residues 1-47 of $G\alpha_{i1}$+64-235 of $G\alpha_{13}$+213-230 of $G\alpha_{i1}$+254-262 of $G\alpha_{13}$+240-353 of $G\alpha_{i1}$. The GST-PBD plasmid was provided by Y. Zheng (Wu et al., Biochemistry 42: 1129-1139 (2003)). Sequences of the final constructs were verified by DNA sequencing.

Wound Healing Assay: Wild type and $G\alpha_{12}^{-/-}G\alpha_{13}^{-/-}$ MEF cells isolated from E8.0 $G\alpha_{12}^{-/-}G\alpha_{13}^{-/-}$ embryos (Gu et al., Proc Natl Acad Sci USA 99: 9352-9357 (2002)) in Dulbecco's Modified Eagle Medium (DMEM) (Invitrogen) containing 10% FBS were seeded into wells of 24-multiwell plates (Becton-Dickinson) (Shan et al., Proc Natl Acad Sci USA 102: 3772-3776 (2005); Yang and Huang, J Biol Chem 280: 27130-27137 (2005)). After they grew to confluency, wounds were made with sterile pipet tips. Cells were washed with Phosphate Buffered Saline (PBS) and refreshed with medium containing 10% fetal bovine serum (FBS) or 20 ng/mL platelet-derived growth factor (PDGF-BB). After overnight incubation at 37° C., cells were fixed and photographed. MEF cells were transfected with Lipofectamine-2000 (transfection efficiency was 10 to 30%) (Invitrogen).

Chamber Cell Migration Assay: Cell migration was assayed in Boyden chambers [8.0 μm pore size polyethylene terephthalate membrane, FALCON cell culture insert (Becton-Dickinson)] (Shan et al., Proc Natl Acad Sci USA 102: 3772-3776 (2005); Yang and Huang, J Biol Chem 280: 27130-27137 (2005)). Cells were first trypsinized and counted. Then $5-10 \times 10^4$ cells in serum free medium (300 μL) were added to the upper chamber, and 500 μL of appropriate medium with 10% FBS or 20 ng/mL PDGF were added to the lower chamber. Transwells were incubated for 4-6 hours at 37° C. Cells on the inside of the transwell inserts were removed with a cotton swab, and cells on the underside of the insert were fixed and stained. Photographs of three random fields were taken, and the number of cells counted to determine the average number of cells that had transmigrated.

MAPK Assay: Whole cell lysates were prepared from MEF cells, $G\alpha_{12}^{-/-}G\alpha_{13}^{-/-}$ cells, and $G\alpha_{12}^{-/-}G\alpha_{13}^{-/-}+G\alpha_{13}$ cells, with or without stimulation by PDGF. Activated ERK MAPK proteins were immunoprecipitated from cell lysates using a monoclonal antibody against phospho-p44/42 ERK MAPK (cross-linked to agarose beads) (Cell Signaling Technology). The ERK MAPK activity was measured by the phosphorylation of substrate GST-Elk-1 that was detected by western blotting with an anti-phospho-Elk-1 antibody.

RNA Interference: RNA interference was performed with Qiagen's 2-For-Silencing siRNA Duplexes. Cells were plated in 6-well plates the day before transfection. 2.5 μg siRNA were diluted in 100 μL buffer EC-R (Qiagen). 7.5 μL RNAiFect transfection reagent (Qiagen) were added to form complexes. After incubation for 15 minutes at room temperature, the complexes were added to the cells. Two days later, the cells were again transfected with the same amount of siRNA. Cells were assayed after three more days' incubation. The sequences for $G\alpha_{13}$ siRNA oligonucleotides were r(GUA CGA CUU UGA AAU UAA A)dTdT (SEQ ID NO: 6) for the sense strand and r(UUU AAU UUC AAA GUC GUA C)dTdC (SEQ ID NO: 7) for the antisense strand. The sequences for the second pair of oligonucleotides used in the interference assay (data not shown) were r(GGG UGA GUC UGU AAA GUA U)dTdT (SEQ ID NO: 8) for the sense strand and r(AUA CUU UAC AGA CUC ACC C)dAdG (SEQ ID NO: 9) for the antisense strand. The control siRNA oligonucleotides were supplied by Qiagen.

Rac Activation Assay: After stimulation with 20 ng/mL PDGF for 10 minutes, cells were washed with PBS and lysed with lysis buffer (20 mM Tris-HCl (pH 8.0), 150 mM NaCl, 1 mM EDTA, 1 mM EGTA, 1% Triton X-100, 1 μg/mL Leupeptin, 1 mM PMSF). 30 μg of GST-PBD attached to beads were added to cell lysates. After incubation at 4° C. for 60 minutes, the beads were washed three times with lysis buffer. SDS sample buffer was added to the beads, and the samples were boiled at 90° C. for 10 minutes and run on 12% SDS-PAGE gels. Immunodetection of Rac was done with anti-Rac antibody (clone 23A8, Upstate Biotechnology).

Fluorescence Microscopy: Staining and observation of actin stress fibers were performed as previously described (Lowry et al., Dev Cell 2: 733-744 (2002)). Cells were plated onto coverslips coated with gelatin. Cells were then fixed with 3.7% formaldehyde, and the fixed cells were then permeabilized in 0.1% Triton X-100 for 5 minutes. After washing in PBS, phalloidin conjugated to rhodamine (Molecular Probes) in a solution containing PBS and 1% BSA was added to stain actin. After incubation for 30 minutes at room temperature, the cells were washed extensively to reduce nonspecific interactions. The coverslips were fixed onto slides and imaged using a Zeiss fluorescence microscope. For Rac and cortactin staining, anti-Rac and anti-cortactin antibodies were from Upstate Cell Signaling Solutions. The immuno-staining was done as previously described (Lowry et al., Dev Cell 2: 733-744 (2002)).

Co-immunoprecipitation Assay: In vivo co-immunoprecipitation was done as described (Lowry et al., Dev Cell 2: 733-744 (2002)). Plasmid cDNAs were transfected into HEK293T cells using the calcium phosphate method, and whole cell extracts were made 48 hours later. 500 μL of whole cell extract in cell lysis buffer were pre-cleared with 20 μL of protein A/G agarose beads for 30 minutes at 4° C. Lysates were then incubated with monoclonal anti-Rac antibody (clone 23A8, Upstate) for 2 hours at 4° C. 40 μL of protein A/G agarose beads were then added. After overnight incubation, the beads were washed three times with 500 μL of lysis buffer. Samples were run on 10% SDS-PAGE gels and western blotted with polyclonal anti-$G\alpha_{13}$ antibody (A-20, Santa Cruz Biotechnology). For in vitro co-immunoprecipitation, cell extracts were replaced with purified proteins in PBS.

Protein Purification: GST or $His_6$-tagged Rac proteins were purified from E. coli, and recombinant $G\alpha_{13}$ was purified as a $His_6$-tagged protein from Sf9 cells as described (Lowry et al., Dev Cell 2: 733-744 (2002)). $G\alpha_{i1}$ and $G\alpha_{13}/_i$-DD1 (in pET28a) proteins were purified from E. coli as $His_6$-tagged proteins.

Tumour Xenograft in a Murine Model: Studies using mice were performed in compliance with the Institutional Animal Care and Use Committee of Weill Medical College of Cornell University.

$G\alpha_{13}^{+/-}$ mice and wild-type littermates were injected intradermally in the right lower back with ~$2\times10^6$ mouse B16 melanoma cells or LLC lung tumor cells (ATCC). Tumour size was measured at the indicated dates with a Vernier caliper and calculated by the formula $V=L\times W^2/2$.

Immunohistochemistry: LLC tumors were excised 8 days after inoculation in wild type and $G\alpha_{13}^{+/-}$ mice. Tissue samples were fixed in 4% paraformaldehyde and imbedded in O.C.T. Sections of 8 μm were prepared and stained with hematoxylin and eosin (H&E) for histopathological analyses, with anti-PECAM/CD31 antibody for blood vessels analyses, and anti-VEGFR2 antibody for the analyses of recruitment of endothelial precursors and endothelial cells.

Example 2

Role of $G\alpha_{13}$ in RTK-Induced Fibroblast Cell Migration

Figure 1A:
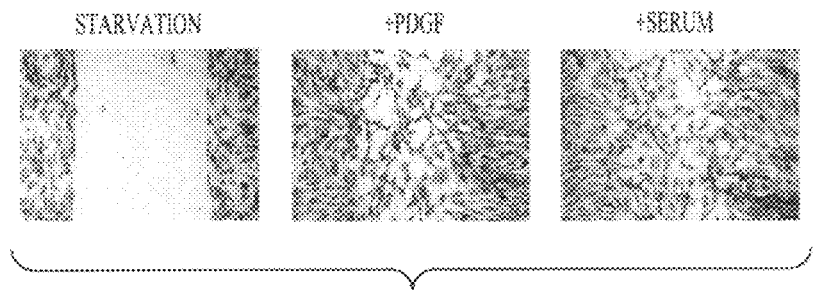
FIG. 1. $G\alpha_{13}$ is required for PDGF-induced cell migration. A. Wound-healing assay showed that PDGF-BB (20 ng/mL) or serum (10% FBS) induced the migration of serum-starved wild-type MEF cells. B. Wound-healing assay showed that serum, but not PDGF, induced the migration of $G\alpha_{12}^{-/-}G\alpha_{13}^{-/-}$ cells. Data are representative of five experiments. C. Chamber assay of PDGF and serum-induced wild-type MEF cell migration. D. Chamber assay of PDGF and serum-induced $G\alpha_{12}^{-/-}G\alpha_{13}^{-/-}$ cell migration. Results are the mean±s.d. of three independent chambers. E. Deficiency of $G\alpha_{12}$ and $G\alpha_{13}$ had no effect on PDGF-induced activation of MAPK. Bottom panel: Western blot with anti-ERK MAPK antibody showing that similar amounts of cell lysates were used in each lane. Data are representative of three experiments. F. Wound-healing assay showed that PDGF did not induce the migration of serum-starved $G\alpha_{12}$-re-expressing $G\alpha_{12}^{-/-}G\alpha_{13}^{-/-}$ cells ($G\alpha_{12}^{-/-}G\alpha_{13}^{-/-}+G\alpha_{12}$ cells). G. Wound-healing assay showed that $G\alpha_{13}$ rescued PDGF-induced migration of $G\alpha_{12}^{-/-}G\alpha_{13}^{-/-}$ cells ($G\alpha_{12}^{-/-}G\alpha_{13}^{-/-}+G\alpha_{13}$ cells). Data are representative of three experiments. H. Chamber assay of PDGF and serum-induced $G\alpha_{12}^{-/-}G\alpha_{13}^{-/-}+G\alpha_{12}$ cell migration. I. Chamber assay of PDGF and serum-induced $G\alpha_{12}^{-/-}G\alpha_{13}^{-/-}+G\alpha_{13}$ cell migration. Results are the mean±s.d. (n=3).
Figure 1B:
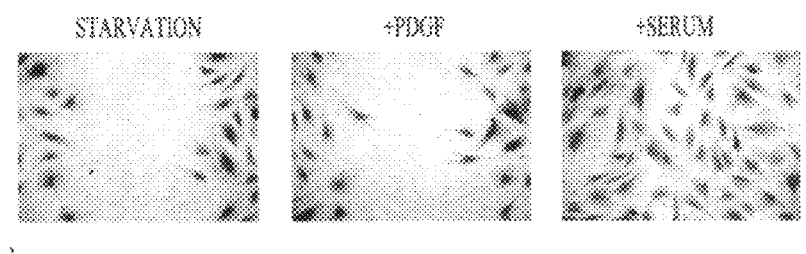
Figure 1C:
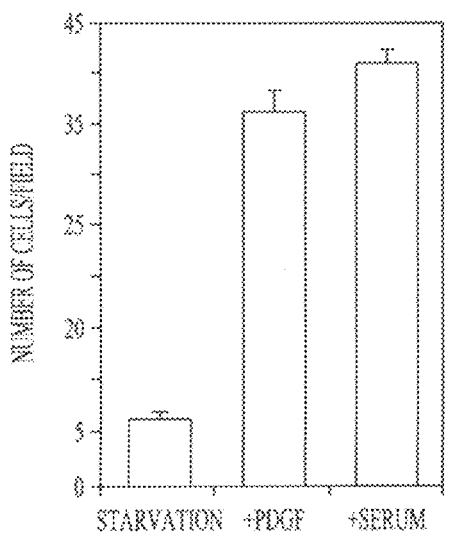
Figure 1D:
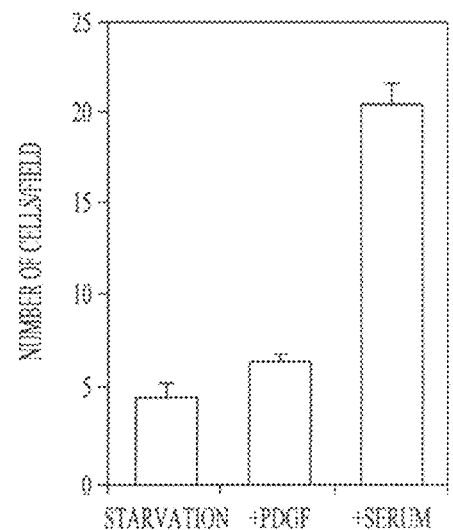
Figure 1E:
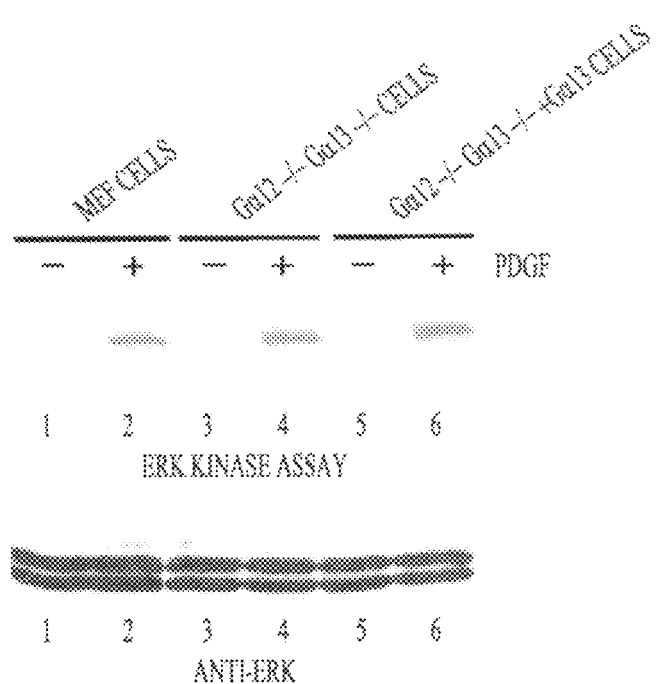
Figure 1F:
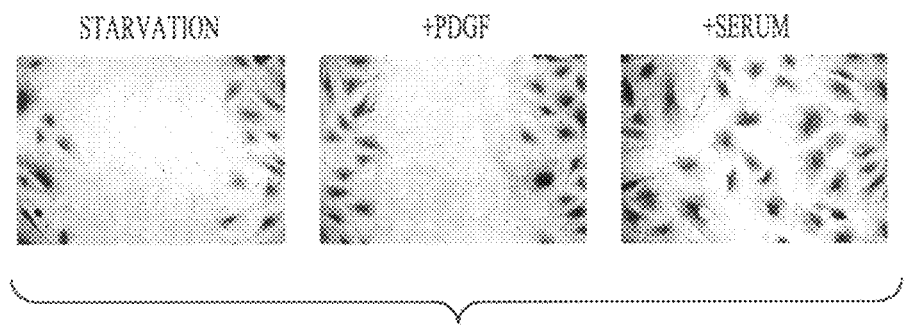
Figure 1G:
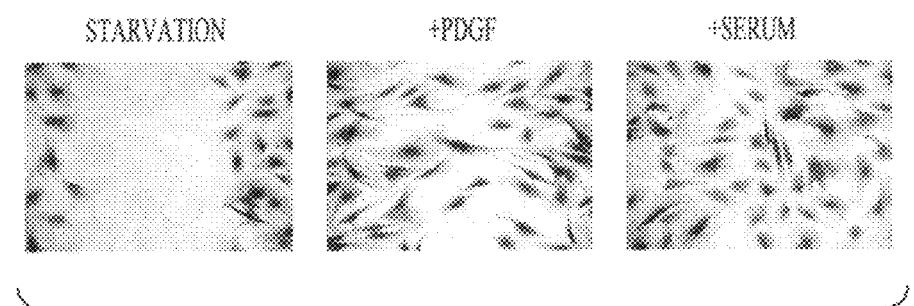
Figure 1H:
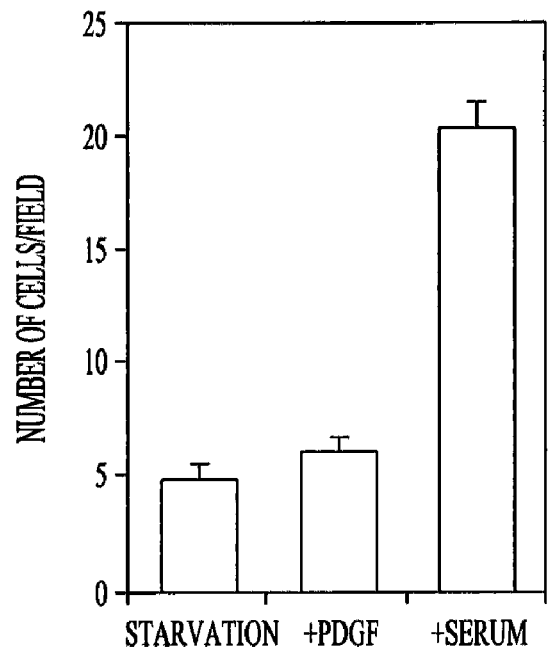
Figure 1I:
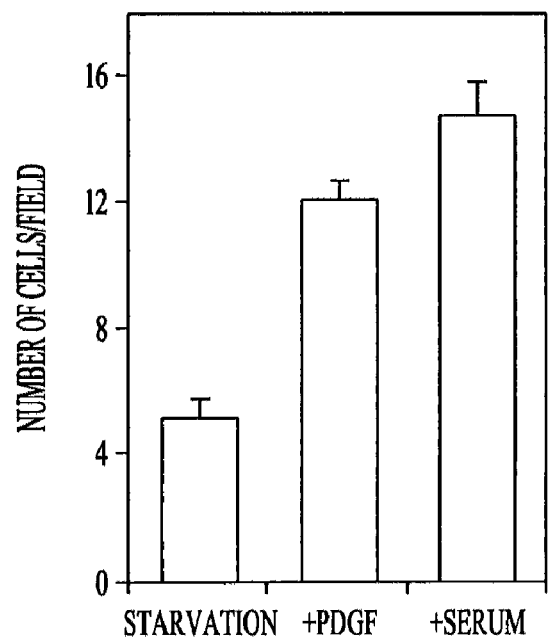
Figure 2:
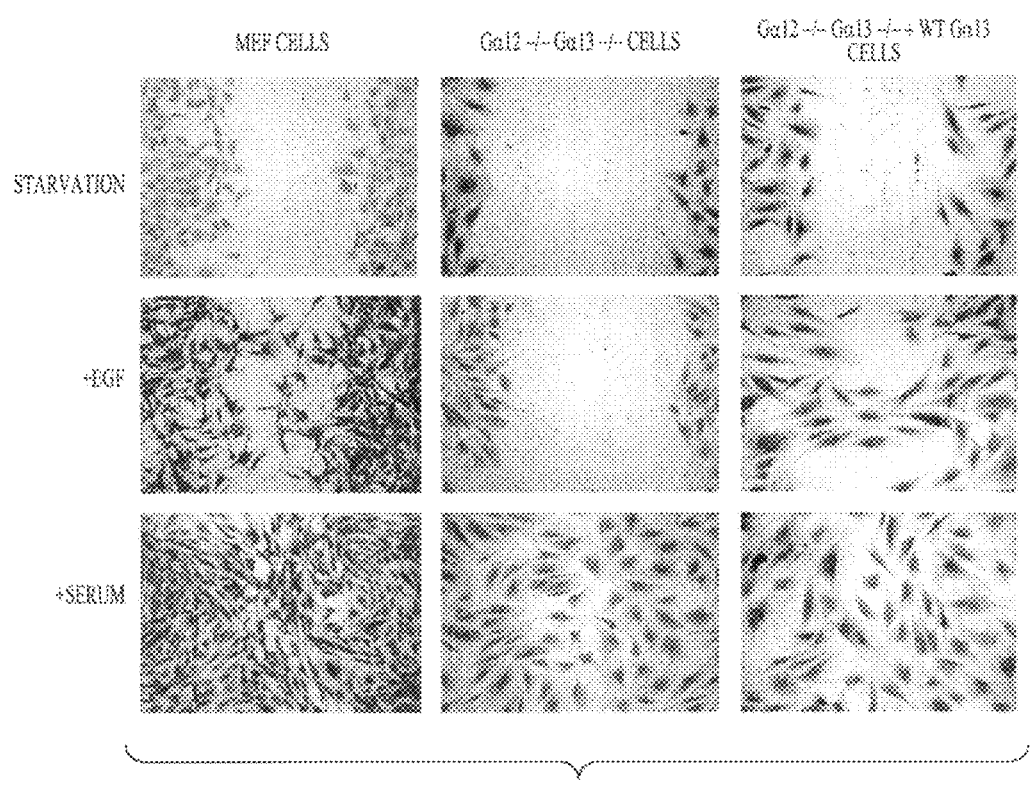
FIG. 2. EGF failed to induce the migration of $G\alpha_{12}^{-/-}G\alpha_{13}^{-/-}$ cells. Left panels: wound-healing assay showed that EGF and serum induced the migration of serum-starved wild-type MEF cells. Middle panels: serum, but not EGF, induced the migration of $G\alpha_{12}^{-/-}G\alpha_{13}^{-/-}$ cells. Right panels: EGF and serum induced cell migration of the $G\alpha_{12}^{-/-}G\alpha_{13}^{-/-}$ cells expressing wild-type $G\alpha_{13}$. Data are representative of three experiments.

In wild-type MEF (mouse embryonic fibroblast) cells, addition of platelet-derived growth factor (PDGF-BB at 20 ng/mL) or serum (10% FBS) induced cell migration (FIG. 1A). Two approaches were used to study the migration of MEF cells, the qualitative wound-healing assay (FIGS. 1, A and B), the quantitative Boyden chamber assay (Shan et al., Proc Natl Acad Sci USA 102: 3772-3776 (2005); Yang and Huang, J Biol Chem 280: 27130-27137 (2005)) (FIGS. 1, C and D). For $G\alpha_{12}^{-/-}G\alpha_{13}^{-/-}$ MEF cells (MEF cells derived from the $G\alpha_{12}^{-/-}G\alpha_{13}^{-/-}$ mouse embryos), addition of PDGF did not induce cell migration (FIGS. 1, B and D). These $G\alpha_{12}^{-/-}G\alpha_{13}^{-/-}$ cells were capable of migrating since addition of serum induced their migration (FIGS. 1, B and D). Furthermore, activation of mitogen-activated protein kinase ERK by PDGF was not affected in $G\alpha_{12}^{-/-}G\alpha_{13}^{-/-}$ cells (FIG. 1E). These results suggest that PDGF signaling to cell migration in fibroblast cells requires $G\alpha_{12}$ or $G\alpha_{13}$ or both. Similarly, epidermal growth factor (EGF) induced the migration of wild-type, but not $G\alpha_{12}^{-/-}G\alpha_{13}^{-/-}$, MEF cells (FIG. 2).

To determine whether $G\alpha_{12}$ or $G\alpha_{13}$ or both are essential for PDGF-induced cell migration, wild-type $G\alpha_{12}$ or $G\alpha_{13}$ were re-expressed in $G\alpha_{12}^{-/-}G\alpha_{13}^{-/-}$ cells. Cells stably re-expressing $G\alpha_{12}$ ($G\alpha_{12}^{-/-}G\alpha_{13}^{-/-}+G\alpha_{12}$ cells) did not respond to PDGF in terms of cell migration (FIGS. 1, F and H). On the other hand, cells stably re-expressing $G\alpha_{13}$ ($G\alpha_{12}^{-/-}G\alpha_{13}^{-/-}+G\alpha_{13}$ cells) showed PDGF-induced cell migration (FIGS. 1, G and I). Although $G\alpha_{12}^{-/-}G\alpha_{13}^{-/-}$ cells spread over a larger surface area and are thinner than wild-type MEF cells, this difference could not explain the defect in cell migration since $G\alpha_{12}^{-/-}G\alpha_{13}^{-/-}+G\alpha_{13}$ cells have the same morphology as $G\alpha_{12}^{-/-}G\alpha_{13}^{-/-}$ cells. Furthermore, $G\alpha_{13}^{-/-}$ cells look similar to wild-type MEF cells (FIG. 3), and yet $G\alpha_{13}^{-/-}$ cells did not migrate in response to PDGF or EGF. These data demonstrated that $G\alpha_{13}$ is essential for RTK-induced cell migration.

Figure 3A:
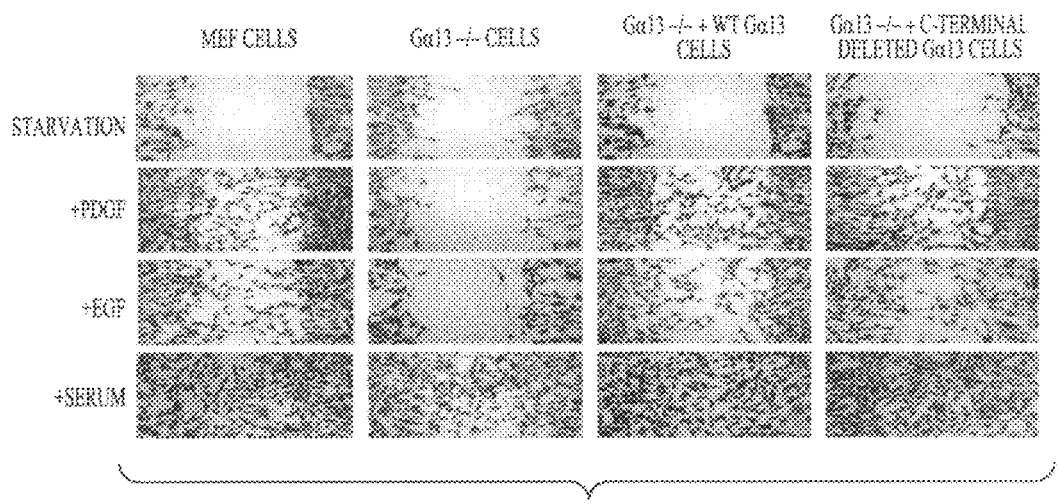
FIG. 3. Deficiency of $G\alpha_{13}$ and $G\alpha_{13}$ RNAi inhibited PDGF-induced cell migration. A. Wound-healing assays showed that serum, but not PDGF and EGF, induced the migration of $G\alpha_{13}^{-/-}$ cells. Re-expression of either a wild-type $G\alpha_{13}$ or a C-terminal truncated $G\alpha_{13}$ mutant rescued the migratory response to PDGF or EGF. Data are representative of five experiments. B. Western blots were performed with whole cell extracts prepared from MEF cells, $G\alpha_{13}^{-/-}$ cells, $G\alpha_{13}^{-/-}$+WT $G\alpha_{13}$ cells, and $G\alpha_{13}^{-/-}$+C-terminal truncated $G\alpha_{13}$ cells. The expression levels of WT $G\alpha_{13}$ and the C-terminal truncated $G\alpha_{13}$ mutant proteins were similar, 80% of endogenous $G\alpha_{13}$ protein. C. Western blots were performed with whole cell extracts prepared from MEF cells treated with control siRNA, $G\alpha_{13}$ siRNA, or cells transfected with both $G\alpha_{13}$ siRNA and wild-type human $G\alpha_{13}$. D. Chamber assay of PDGF-induced migration of MEF cells treated with control siRNA, $G\alpha_{13}$ siRNA, or cells transfected with both $G\alpha_{13}$ siRNA and wild-type human $G\alpha_{13}$. Results are the mean±s.d. of three independent chambers. E. Wound-healing assay showed that $G\alpha_{13}$ siRNA treatment reduced PDGF-induced MEF cell migration. Data are representative of three experiments.
Figure 3B:
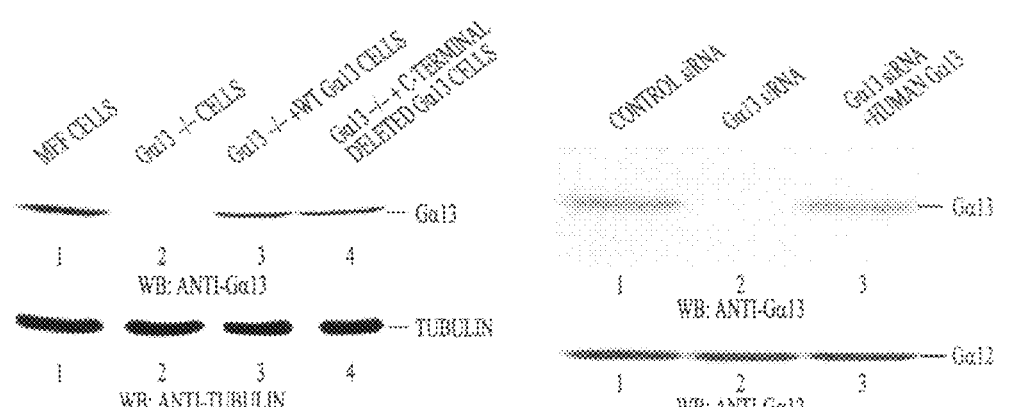
Figure 3C:
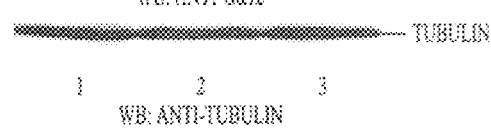
Figure 3D:
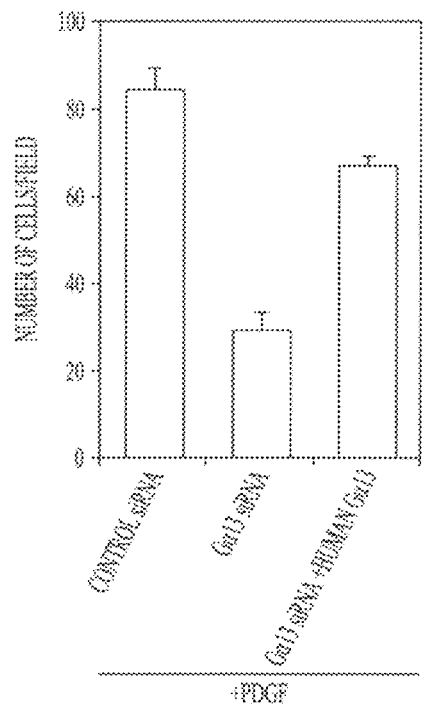
Figure 3E:
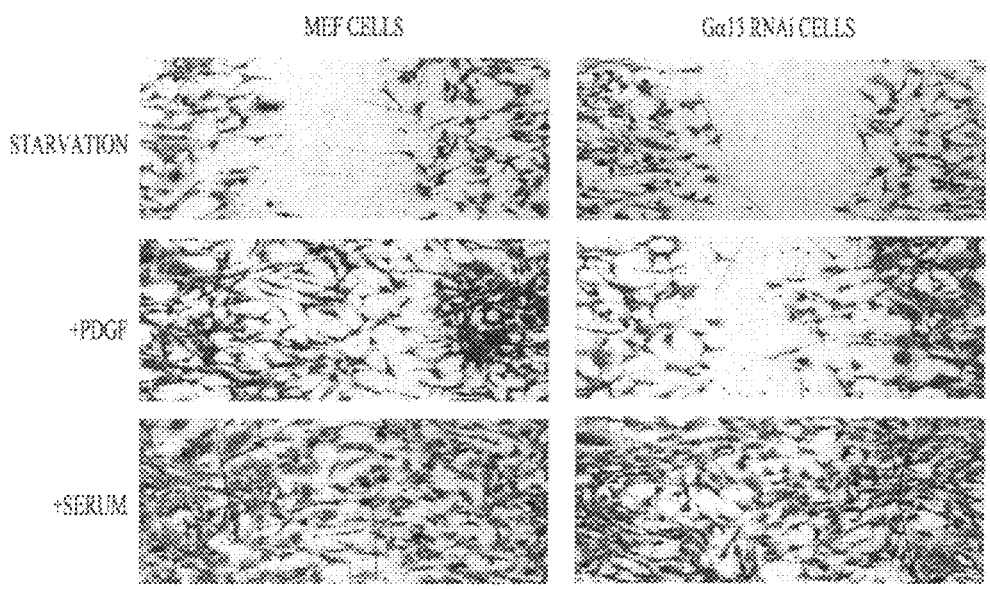

To further confirm the role of $G\alpha_{13}$ in growth factor-induced cell migration, two additional experimental systems were used. First, fibroblast cells isolated from $G\alpha_{13}$ single knockout mouse embryos were employed (FIG. 3A). While serum induced the migration of $G\alpha_{13}^{-/-}$ cells, neither PDGF nor EGF could induce $G\alpha_{13}^{-/-}$ cell migration. Re-expression of a wild-type $G\alpha_{13}$ in $G\alpha_{13}^{-/-}$ cells rescued the migratory response to PDGF and EGF (FIG. 3A). The protein level of re-expressed $G\alpha_{13}$ was ~80% that of endogenous $G\alpha_{13}$ protein (FIG. 3B). Second, RNA interference was used to downregulate the endogenous $G\alpha_{13}$ protein levels in wild-type MEF cells. Transfection of an siRNA against mouse $G\alpha_{13}$ significantly reduced the level of endogenous mouse $G\alpha_{13}$ protein, while transfection with a control siRNA did not (FIG. 3C). The protein levels of $G\alpha_{12}$ and tubulin were not changed in these siRNA transfected cells (FIG. 3C). Notably, $G\alpha_{13}$ siRNA-treated cells showed a defective cell migratory response to PDGF stimulation as measured by both the chamber and wound-healing assays (FIGS. 3, D and E). Furthermore, a second siRNA against a different region of mouse $G\alpha_{13}$ gave similar results (data not shown). Moreover, human $G\alpha_{13}$ was expressed in siRNA-treated MEF cells. Introduction of human $G\alpha_{13}$ rescued PDGF-induced cell migration (FIG. 3D). Without PDGF (or other stimuli), migration of cells treated with $G\alpha_{13}$ RNAi or $G\alpha_{13}$ RNAi+human $G\alpha_{13}$ was not significantly different from that of cells treated with control RNAi (data not shown). Hence, these data confirmed that $G\alpha_{13}$ is essential for PDGF-induced MEF cell migration.

Example 3

Rac Acts Upstream of or in Parallel to $G\alpha_{13}$

Figure 4C:
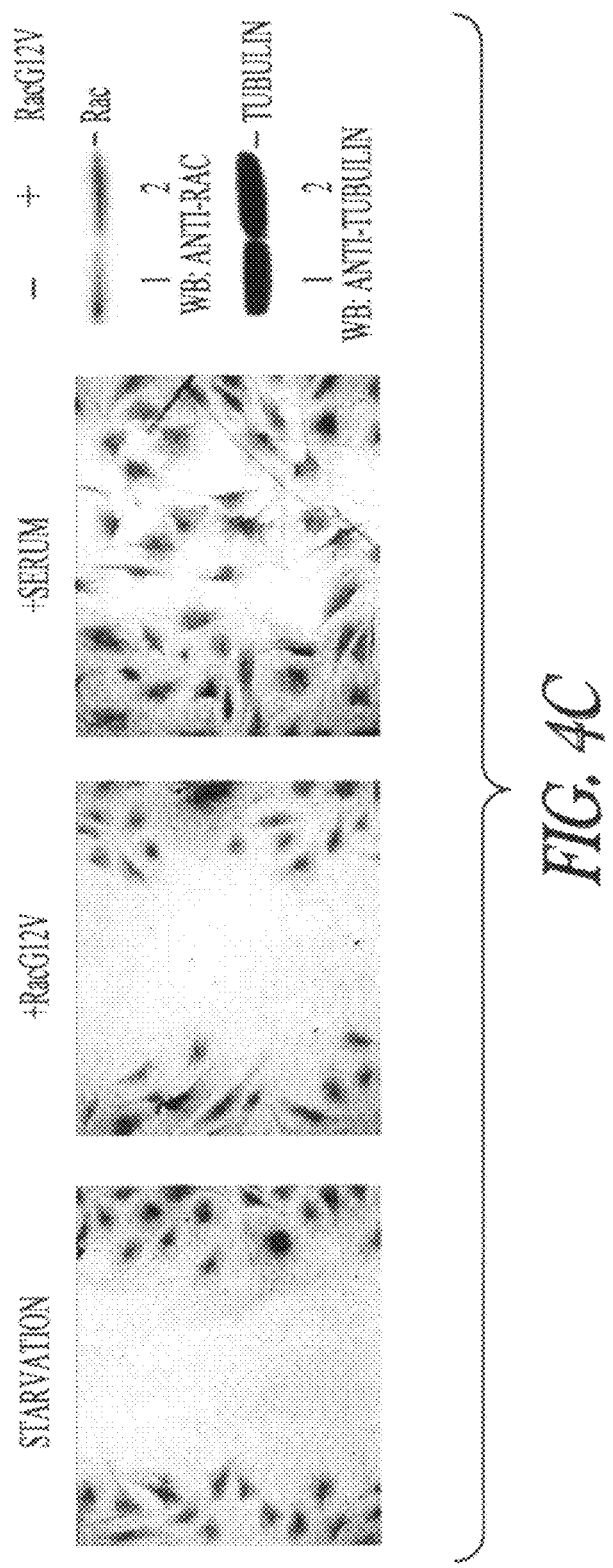
FIG. 4. RacG12V failed to induce $G\alpha_{12}^{-/-}G\alpha_{13}^{-/-}$ cell migration. A. PDGF-induced MEF cell migration was blocked by a dominant-negative mutant Rac (RacT17N). Western blot in the right panel shows the expression levels of Rac proteins in untransfected and transfected cells. B. A constitutive active mutant Rac (Rac1G12V) induced MEF cell migration, while transfection of a control empty vector plasmid or of $G\alpha_{13}$QL plasmid did not. The expression levels of Rac and $G\alpha_{13}$ proteins in untransfected and transfected cells are shown by western blots (right panels). C. Rac1G12V did not induce $G\alpha_{12}^{-/-}G\alpha_{13}^{-/-}$ cell migration. All above data were from wound-healing assays and are representative of three experiments. Western blot (right panel) shows the expression levels of Rac proteins in untransfected and transfected cells. D. Chamber assay of Rac1G12V effect on the migration of MEF and $G\alpha_{12}^{-/-}G\alpha_{13}^{-/-}$ cells. Results are mean±s.d. (n=3). The expression levels of Rac proteins in untransfected and transfected cells are shown by western blot (right panel). E. Rac activation assay. Cell lysates from MEF or $G\alpha_{12}^{-/-}G\alpha_{13}^{-/-}$ cells with or without PDGF treatment were incubated with GST-PBD. The pulled-down active Rac was immunoblotted with anti-Rac antibody. The bottom panel shows the western blot with anti-Rac of the cell lysate used (10% of that used in the top panel). Data are representative of three experiments.
Figure 4D:
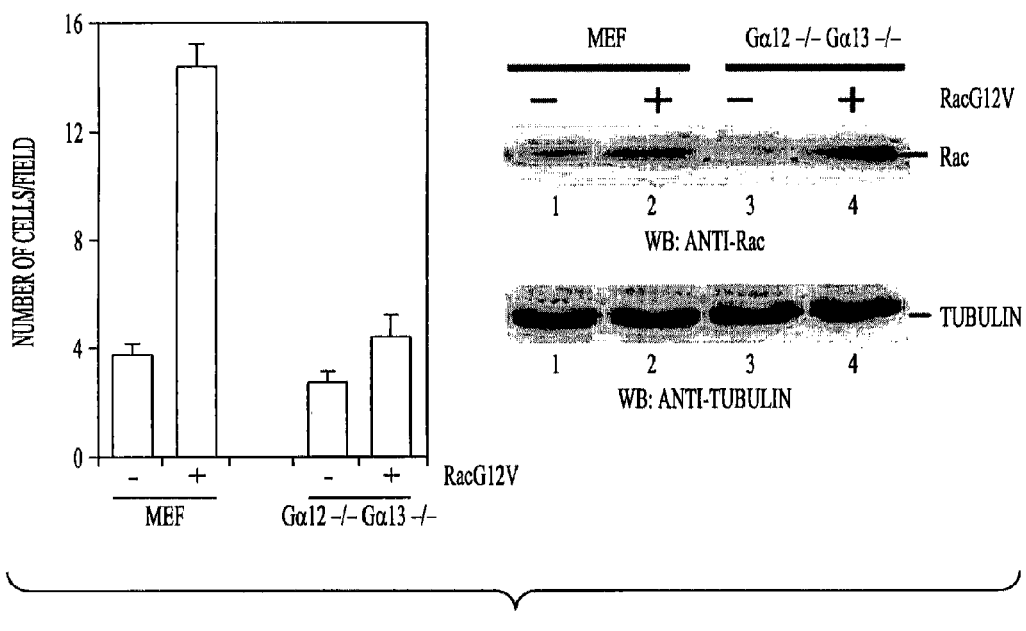
Figure 4E:
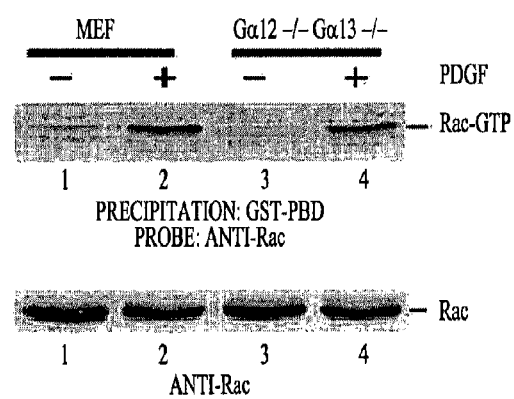

To investigate the mechanism by which a heterotrimeric G protein, $G\alpha_{13}$, is involved in growth factor-induced cell migration, the relationship of $G\alpha_{13}$ was examined with other known signaling molecules downstream of PDGFRs. The Rho-family small GTPase Rac is involved in lamellipodia formation, cell adhesion, and cell migration (Hall, Science 279: 509-514 (1998); Ridley et al., Cell 70: 401-410 (1992); Sugihara et al., Oncogene 17: 3427-3433 (1998)). Genetic evidence has demonstrated that Rac is essential for PDGF-induced cell migration (Sugihara et al., Oncogene 17: 3427-3433 (1998)). As shown in FIG. 4A, dominant negative Rac mutants (Rac1 T17N) reduced PDGF-induced migration of MEF cells. Constitutively-active Rac mutants (Rac1 G12V) induced MEF cell migration in the absence of PDGF (FIG. 4B). These data confirm a role for Rac in PDGF-induced migration of MEF cells. Since both $G\alpha_{13}$ and Rac are involved in PDGF signaling to cell migration, studies were conducted to determine whether Rac acts upstream or downstream of $G_{13}$. Expression of the constitutively active Rac mutants (Rac1 G12V) failed to induce the migration of $G\alpha_{12}^{-/-} G\alpha_{13}^{-/-}$ cells (FIGS. 4, C and D). Furthermore, in $G\alpha_{12}^{-/-} G\alpha_{13}^{-/-}$ cells, PDGF still activated Rac (FIG. 4E). Moreover, constitutively active mutant $G\alpha_{13}$Q226L could not induce MEF cell migration by itself, indicating that $G\alpha_{13}$ is required, but not sufficient, for cell migration (FIG. 4B). Therefore, Rac acts upstream of or in parallel to $G\alpha_{13}$ in PDGF-induced cell migration. If Rac works upstream of $G\alpha_{13}$, it is likely that Rac employs several signaling pathways to promote cell migration and that $G_{13}$ is part of one of these pathways.

Example 4

No Requirement for Coupling to a GPCR

Figure 5A:
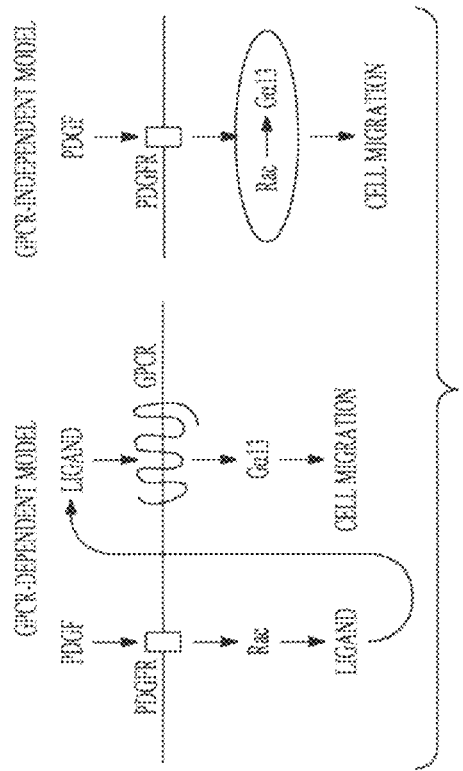
FIG. 5. PDGF-induced $G\alpha_{13}$-dependent cell migration does not require GPCR coupling. A. Two models that could explain the role of $G\alpha_{13}$ in PDGF-induced cell migration (see text for description). B. LPA-induced actin stress fiber formation in wild-type MEF cells, $G\alpha_{12}^{-/-}G\alpha_{13}^{-/-}$ cells, $G\alpha_{12}^{-/-}G\alpha_{13}^{-/-}$+wild-type (WT) $G\alpha_{13}$ cells, and $G\alpha_{12}^{-/-}G\alpha_{13}^{-/-}$+C-terminal truncated $G\alpha_{13}$ cells. C. Western blots were performed with whole cell extracts prepared from wild-type MEF cells, $G\alpha_{12}^{-/-}G\alpha_{13}^{-/-}$ cells, $G\alpha_{12}^{-/-}G\alpha_{13}^{-/-}$+wild-type (WT) $G\alpha_{13}$ cells, and $G\alpha_{12}^{-/-}G\alpha_{13}^{-/-}$+C-terminal truncated $G\alpha_{13}$ cells. The expression levels of WT $G\alpha_{13}$ and the C-terminal truncated $G\alpha_{13}$ mutant proteins were similar, ~25% of endogenous $G\alpha_{13}$ protein. D. Wound-healing assay of PDGF-induced migration of the $G\alpha_{12}^{-/-}G\alpha_{13}^{-/-}$ cells expressing a C-terminal truncated $G\alpha_{13}$. E. Chamber assay of PDGF-induced migration of $G\alpha_{12}^{-/-}G\alpha_{13}^{-/-}$ cells expressing a C-terminal truncated $G\alpha_{13}$. F. LPA induced the migration of MEF cells and $G\alpha_{13}^{-/-}$+WT $G\alpha_{13}$ cells, but not $G\alpha_{13}^{-/-}$ cells and $G\alpha_{13}^{-/-}$+C-terminal truncated $G\alpha_{13}$ cells. Data are representative of three experiments.
Figure 5B:
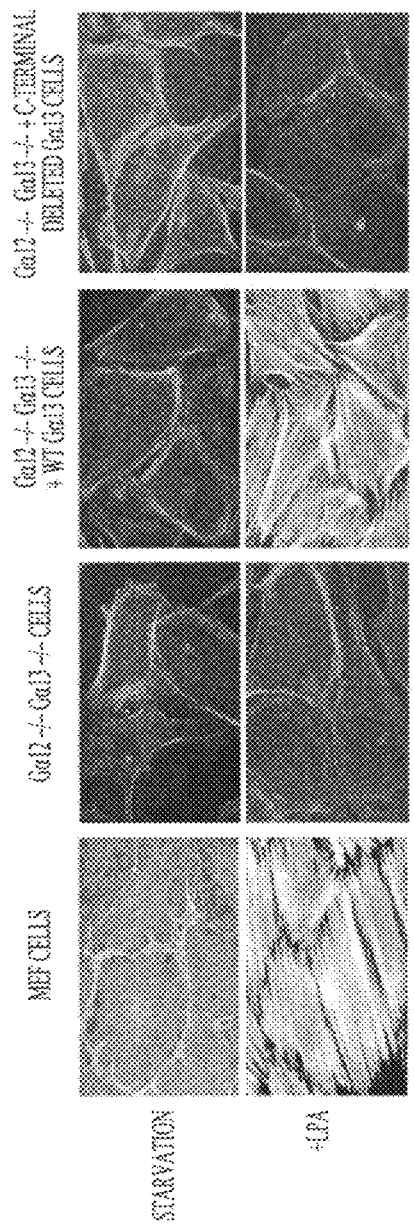
Figure 5C:
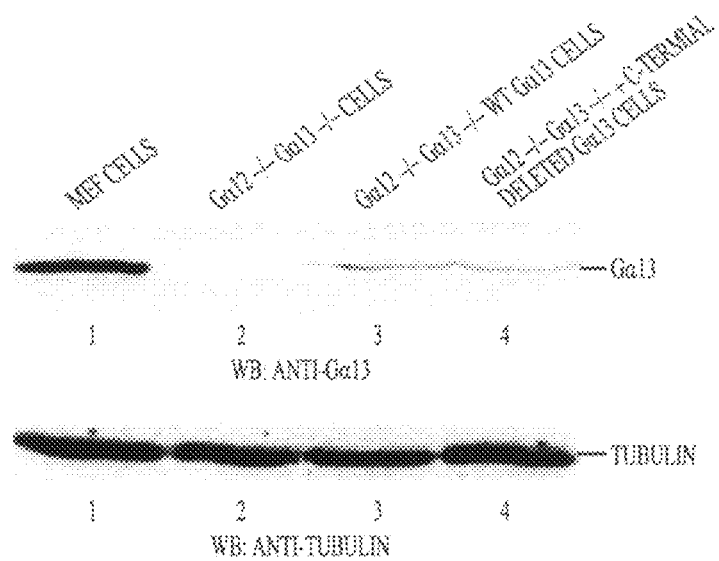
Figure 5D:
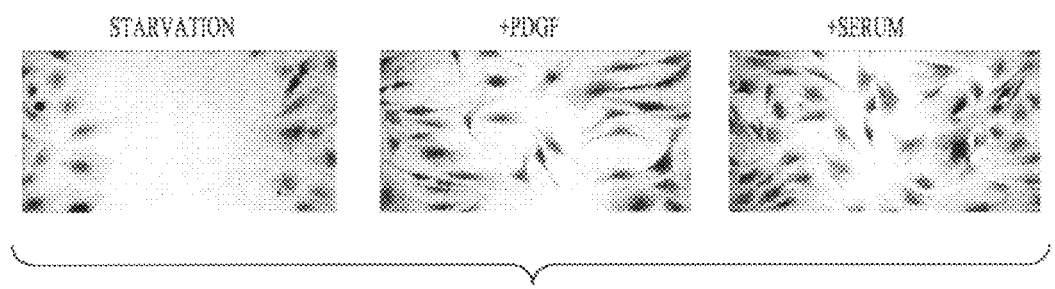
Figure 5E:
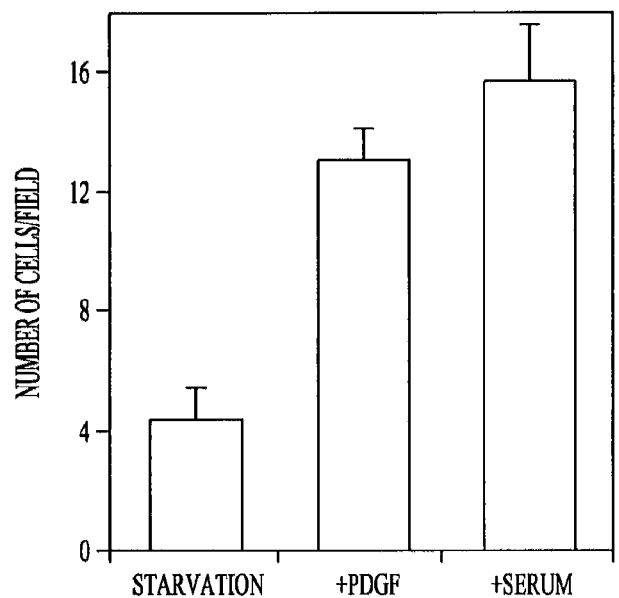
Figure 5F:
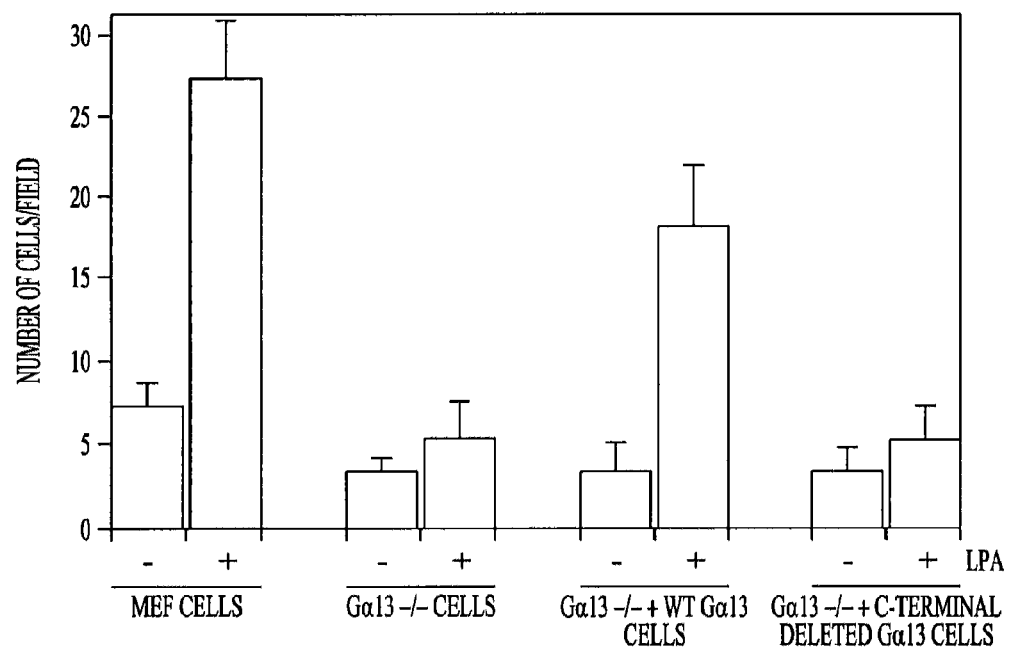

If Rac works upstream of $G\alpha_{13}$, it is possible that PDGF, through Rac, induces the production and secretion of a ligand(s) that signals through a $G_{13}$-coupled GPCR (FIG. 5A). Alternatively, Rac could signal through $G\alpha_{13}$ without a GPCR (FIG. 5A). The possibility of a GPCR working between PDGFR and $G_{13}$ was tested. If there is a $G\alpha_{13}$-coupled receptor involved, a $G\alpha_{13}$ mutant that is defective in coupling to the receptor should not be able to rescue the $G\alpha_{13}$ deficiency. The C-termini of $G\alpha$ subunits of heterotrimeric G proteins are essential for coupling to GPCRs (Bourne, Curr Opin Cell Biol 9: 134-142 (1997); Conklin et al., Nature 363: 274-276 (1993); Garcia et al., Embo J 14: 4460-4469 (1995); Gilchrist et al., J Biol Chem 276: 25672-25679 (2001); Hirsch et al., Genes Dev 5: 467-474 (1991); Kallal and Kurjan, Mol Cell Biol 17: 2897-2907 (1997); Masters et al., Science 241: 448-451 (1988); Onrust et al., Science 275: 381-384 (1997); Osawa and Weiss, J Biol Chem 270: 31052-31058 (1995); Sullivan et al., Nature 330: 758-760 (1987)). Addition of epitope tags at, or deletion of amino acid residues from, the C-terminal end of Go: blocks the GPCR-G protein interactions in vitro and in cells (Bourne, Curr Opin Cell Biol 9: 134-142 (1997) (and our unpublished observations). Several C-terminal tagged or truncated $G\alpha_{13}$ mutants were made that are defective in coupling to GPCRs, as described in Example 1. Since the results from these $G\alpha_{13}$ mutants were the same, only results from the $G\alpha_{13}$ mutant with deletion of the last five amino acid residues and with a C-terminal Myc and $His_6$ tags (referred to as the $G\alpha_{13}$ truncated mutant) are described in detail here. To confirm that this $G\alpha_{13}$ truncated mutant could not couple to a GPCR in cells, the formation of actin stress fibers induced by $G\alpha_{13}$-coupled receptors for lysophosphatidic acid (LPA) was examined. It was previously demonstrated that LPA uses $G\alpha_{13}$ to induce the formation of actin stress fibers in MEF cells (Gohla et al., J Biol Chem 274: 17901-17907 (1999)). As shown in FIG. 5B, while LPA induced formation of actin stress fibers in MEF cells, LPA failed to induce actin stress fiber formation in $G\alpha_{12}^{-/-} G\alpha_{13}^{-/-}$ cells. Stable expression of wild-type $G\alpha_{13}$ in $G\alpha_{12}^{-/-} G\alpha_{13}^{-/-}$ cells rescued the LPA-induced stress fiber formation. On the other hand, $G\alpha_{12}^{-/-} G\alpha_{13}^{-/-}$ cells stably expressing the $G\alpha_{13}$ truncated mutant did not show stress fiber formation after LPA stimulation (FIG. 5B). The protein expression levels of wild-type $G\alpha_{13}$ and the C-terminal truncated $G\alpha_{13}$ mutant proteins in these cells were similar, and ~25% that of endogenous $G\alpha_{13}$ protein (FIG. 5C). These results confirm that a C-terminal truncated $G\alpha_{13}$ could not couple to GPCRs in cells. The rescue of PDGF-induced cell migration of $G\alpha_{12}^{-/-} G\alpha_{13}^{-/-}$ cells by wild-type and C-terminal truncated $G\alpha_{13}$ was studied. Both wild type $G\alpha_{13}$ and the C-terminal truncated $G\alpha_{13}$ rescued the cell migration defect of $G\alpha_{12}^{-/-} G\alpha_{13}^{-/-}$ cells (compare FIGS. 1 G & I with FIGS. 5 D & E). These results were verified by chamber assay showing a similar extent of rescue (FIGS. 1I and 5E). Furthermore, this bypass of a GPCR was not due to overexpression of $G\alpha_{13}$ mutant proteins in $G\alpha_{12}^{-/-} G\alpha_{13}^{-/-}$ cells since the expression level of $G\alpha_{13}$ in $G\alpha_{13}$-deficient cells was less than that in wild-type MEF cells (FIG. 5C). Therefore, these data suggest that a $G_{13}$-coupled GPCR is unlikely to be essential in this pathway.

Figure 6:
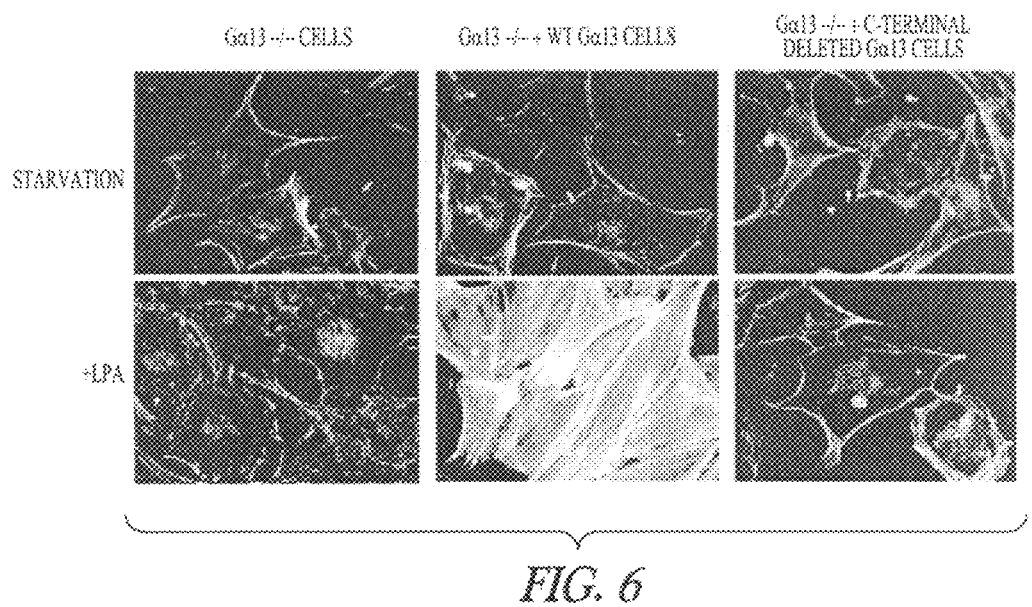
FIG. 6. LPA (10 µM) induced actin stress fiber formation in $G\alpha_{13}^{-/-}$+wild-type (WT) $G\alpha_{13}$ cells, but not in $G\alpha_{13}^{-/-}$ and $G\alpha_{13}^{-/-}$+C-terminal truncated $G\alpha_{13}$ cells. Data are representative of three experiments.

To further confirm this GPCR-independence, these experiments were repeated in $G\alpha_{13}^{-/-}$ single knockout MEF cells and similar results were observed (FIG. 3A and FIG. 6). While expression of wild-type $G\alpha_{13}$ in $G\alpha_{13}^{-/-}$ cells rescued LPA-induced stress fiber formation, the C-terminal truncated $G\alpha_{13}$ did not (FIG. 6). On the other hand, expression of either wild-type or the C-terminal truncated $G\alpha_{13}$ in $G\alpha_{13}^{-/-}$ cells rescued PDGF- (and EGF) induced migration of these cells (FIG. 3A). Moreover, while wild-type $G\alpha_{13}$ rescued the migration defect of $G\alpha_{13}^{-/-}$ cells in response to LPA, the C-terminal truncated $G\alpha_{13}$ mutant did not (FIG. 5F), reaffirming the functional uncoupling of this C-terminal truncated $G\alpha_{13}$ mutant from GPCRs. Together, these results demonstrate that coupling to GPCRs is not essential for the participation of $G\alpha_{13}$ in RTK-induced cell migration.

Example 5

Complex Formation Between Rac and $G\alpha_{13}$

Figure 7A:
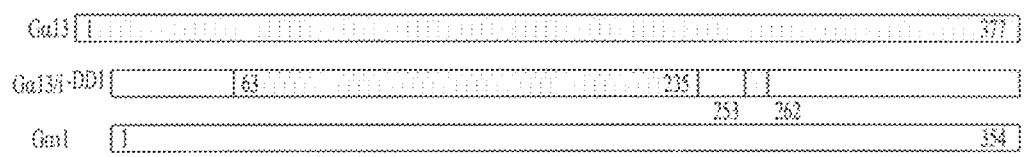
FIG. 7. Rac and $G_{13}$ form a complex in vitro and in cells. A. Diagram of the $G\alpha_{13}$, Gαi1, and the chimera $G\alpha_{13/i}$-DD1 constructs. B. Purified GST-Rac or GST-Rho pre-loaded with GDP or GTPγS was mixed with purified $G\alpha_{13}$, $G\alpha_{i1}$, and $G\alpha_{13/1}$-DD1 pre-loaded with GDP or GTPγS. Glutathione-beads were used to pull-down. Western blots were with anti-His6 antibodies. C. Purified Rac pre-loaded with GTPγS and/or purified wild-type $G\alpha_{13}$ pre-loaded with GDP were pulled down with anti-Rac or anti-Rho antibodies. Western blots were with an anti-$G\alpha_{13}$ antibody. D. Purified Rac pre-loaded with GTPγS, purified wild-type $G\alpha_{13}$ pre-loaded with GDP, and/or purified Gβγ were pulled down with anti-Rac or anti-$G\alpha_{13}$ antibodies. Western blots were with an anti-GP antibody. E. HEK293T cells were transfected with indicated plasmids. Whole cell lysates were prepared and immunoprecipitated with anti-Rac antibodies. Western blot was with anti-Gα$_{13}$ or anti-Gα$_{12}$ antibody. F. MEF cell lysates were immunoprecipitated with anti-Rac antibody and western blotted with anti-Gα$_{13}$ antibody. Data are representative of three to five experiments.
Figure 7B:
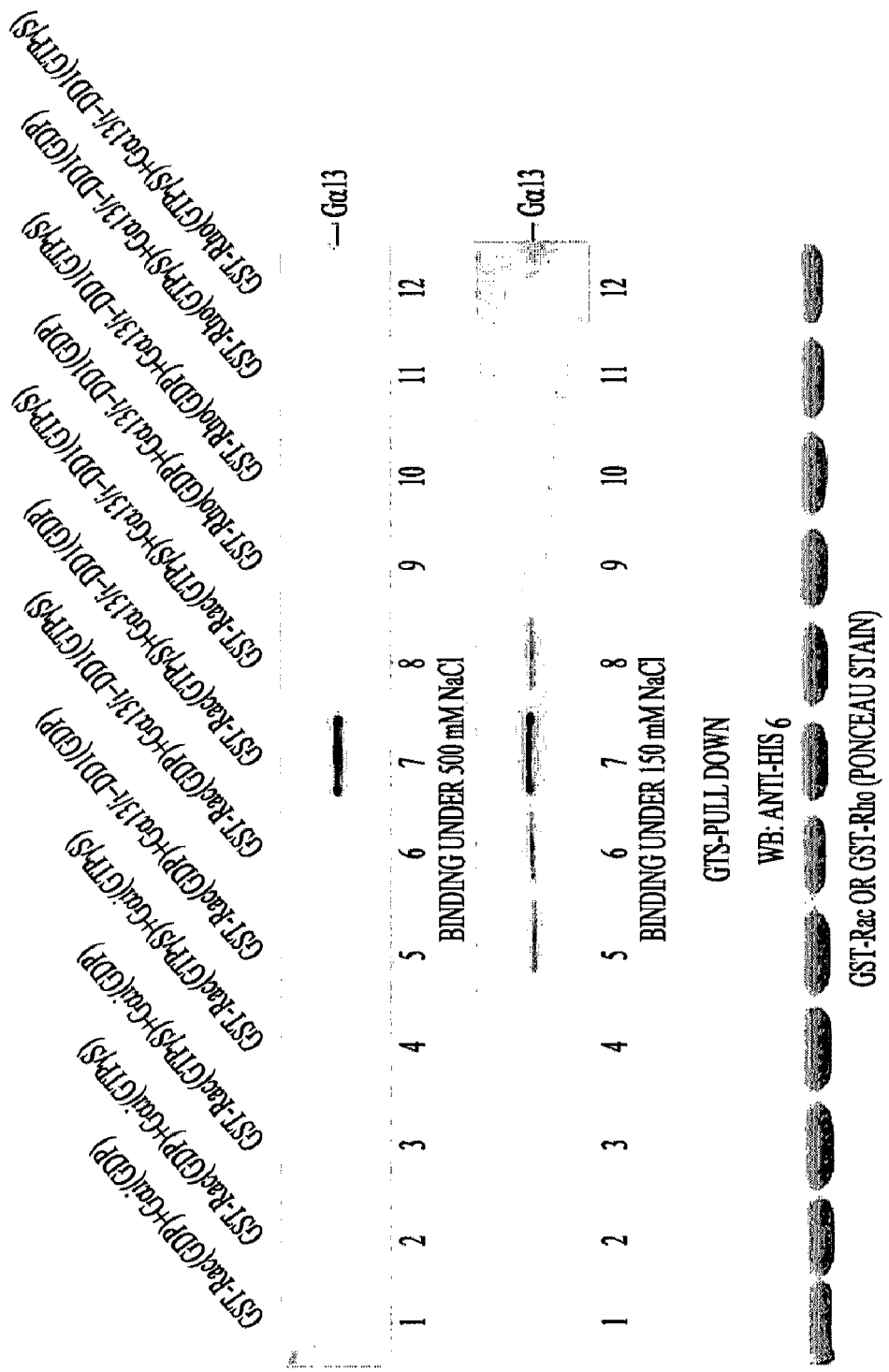
Figure 7C:
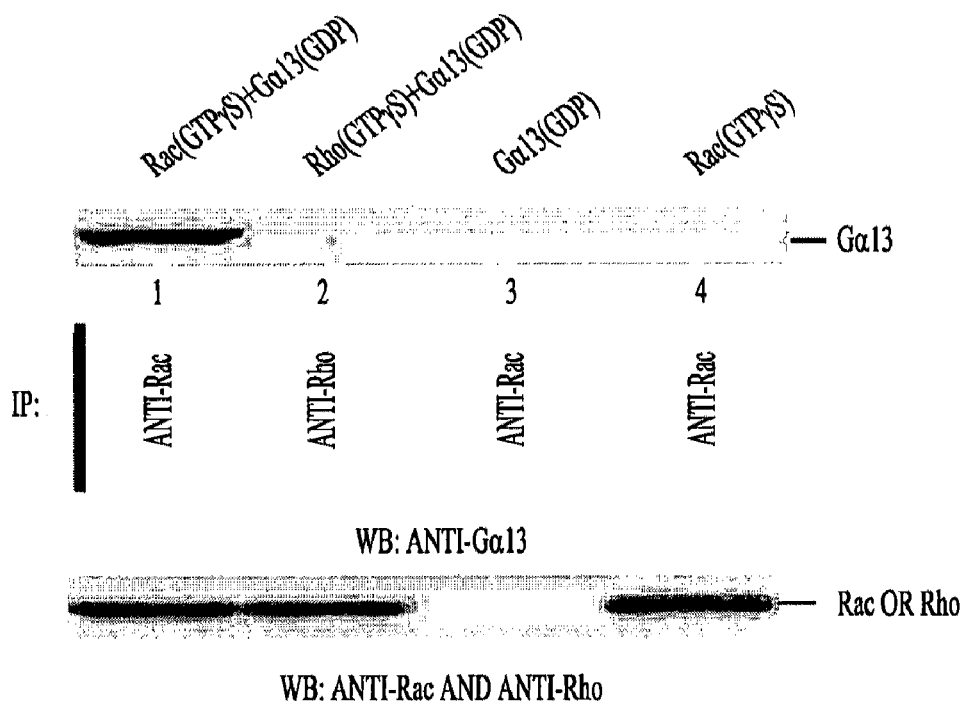
Figure 7D:
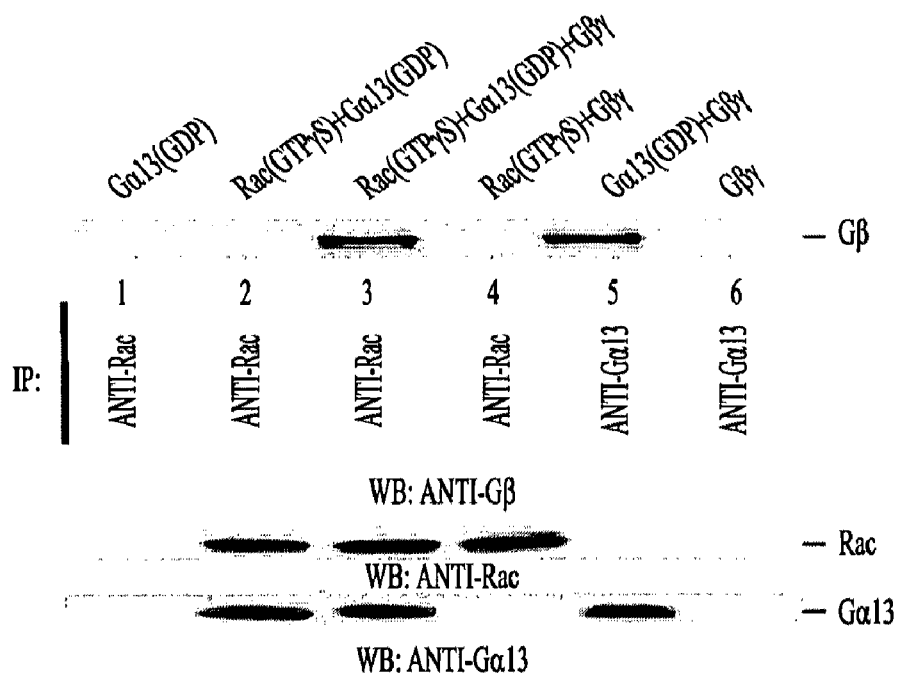

To further understand the mechanism by which Rac and $G\alpha_{13}$ work together in RTK-induced cell migration, the possibility of Rac and $G\alpha_{13}$ existing in a complex was examined. First, in vitro binding experiments were performed using purified Rac1 and purified $G\alpha_{13}$ (FIG. 7, A-D). Since purified wild-type $G\alpha_{13}$ proteins were difficult to load with GTPγS, a $G\alpha_{13}$ and $G\alpha_{i1}$ chimera ($G\alpha_{13}$/i-DD1) was generated based on the recently reported strategy (Chen et al., Nat Struct Mol Biol 12: 191-197 (2005)) (FIG. 7A). The $G\alpha_{13}$/i-DD1 protein could be purified from E. coli and the purified protein could be loaded with $^{35}$S-GTPγS (the final ratio of $^{35}$S-GTPγS loaded versus $G\alpha_{13}$/i-DD1 protein was ~0.35). $G\alpha_{13}$/i-DD1, but not Gail, could rescue PDGF-induced migration of $G\alpha_{13}^{-/-}$ cells (data not shown). Purified GST-Rac1 proteins pre-loaded with GDP or GTPγS were used for in vitro pull-down assays (FIG. 7B). When the binding reaction was carried out in the presence of 500 mM NaCl, only GST-Rac1 (GTPγS) pulled down $G\alpha_{13}$/i-DD1(GDP) (FIG. 7B). When the binding experiments were performed under less stringent conditions (in the presence of 150 mM NaCl), additional weak interactions were observed between Rac1(GDP) and $G\alpha_{13}$/i-DD1(GDP), Rac1(GDP) and $G\alpha_{13}$/i-DD1(GTPγS), as well as Rac1(GTPγS) and $G\alpha_{13}$/i-DD1(GTPγS) (FIG. 7B). Furthermore, neither Rac1(GDP) nor Rac1(GTPγS) interacted with $G\alpha_{i1}$(GDP) or $G\alpha_{i1}$(GTPγS) (FIG. 7B). Moreover, RhoA(GDP) and RhoA(GTPγS) did not bind $G\alpha_{13}$/i-DD1 pre-loaded with GDP or GTPγS (FIG. 7B). Therefore, the strongest interaction is between Rac(GTPγS) and $G\alpha_{13}$ (GDP). This result was confirmed with purified wild-type $G\alpha_{13}$ (FIG. 7C). When purified Rac1(GTPγS) and $G\alpha_{13}$ (GDP) were incubated together, an anti-Rac antibody pulled-down $G\alpha_{13}$, while RhoA(GTPγS) did not under the same conditions (FIG. 7C). Similarly, anti-$G\alpha_{13}$ antibodies pulled down Rac1 only in the presence of $G\alpha_{13}$, reaffirming their direct interaction (data not shown). Since $G\alpha_{13}$(GDP) can bind Gβγ subunits, whether Rac(GTPγS) and Gβγ compete for binding to $G\alpha_{13}$(GDP) was examined. As shown in FIG. 7D, anti-Rac antibodies co-immunoprecipitated Gβγ only in the presence of $G\alpha_{13}$(GDP). These data imply that, after activation, Rac could interact with $G\alpha_{13}$ subunits or with $G\alpha_{13}$-Gβγ trimer. Together, these results demonstrate that Rae and $G\alpha_{13}$ directly interact with each other. Moreover, this provides an example of direct interaction between a heterotrimeric G protein and a Rho-family small GTPase.

Figure 7E:
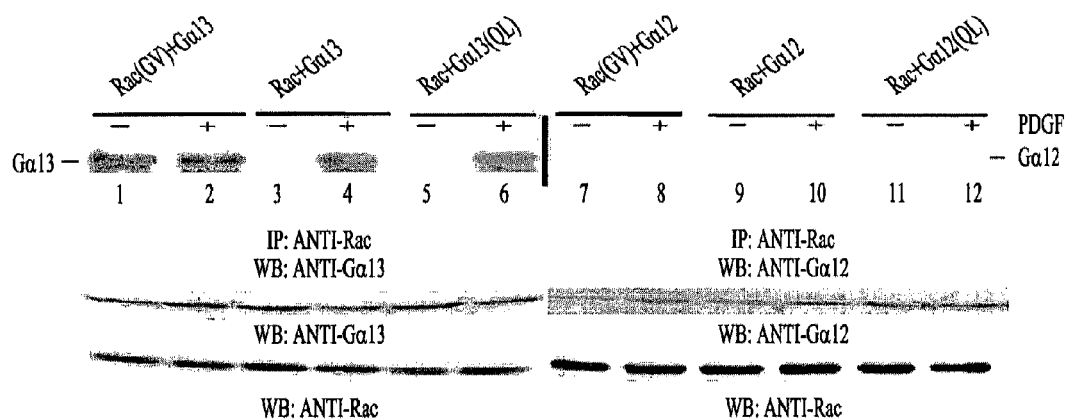
Figure 7F:
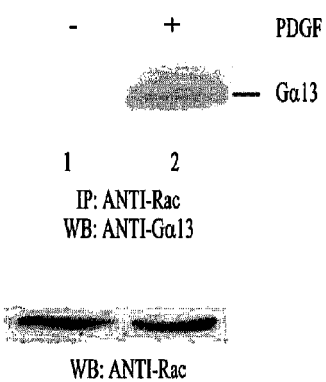

Next, the interaction of Rae and $G\alpha_{13}$ in cells was investigated. First, the GDP or GTP dependency of the interaction in cells was examined. Constitutively active Rac1(G12V), wild-type Rac, constitutively active $G\alpha_{13}$(Q226L), and wild-type $G\alpha_{13}$ plasmids were used to transfect HEK293T cells. Cells were treated with or without PDGF. After immunoprecipitation with anti-Rac antibodies, co-precipitation of $G\alpha_{13}$ was examined with anti-$G\alpha_{13}$ antibodies (FIG. 7E). When Rac is active [Rac1(G12V)], co-immunoprecipitation of $G\alpha_{13}$ was detected in the absence of PDGF treatment (FIG. 7E, lane 1). This confirmed the in vitro data showing the interaction of Rac(GTPγS) and $G\alpha_{13}$(GDP). On the other hand, when wild-type Rac and $G\alpha_{13}$ were used, PDGF stimulation was required to observe the interaction (FIG. 7E, lanes 3 and 4). This PDGF treatment was likely needed to activate Rac, not $G\alpha_{13}$ since expression of $G\alpha_{13}$(Q226L) and wild-type Rac did not lead to co-immunoprecipitation without PDGF stimulation (FIG. 7E, lane 5). The interaction seen after PDGF treatment (FIG. 7E, lane 6) in cells expressing Rae and $G\alpha_{13}$ (Q226L) might reflect the binding of activated Rac with endogenous $G\alpha_{13}$ or $G\alpha_{13}$(Q226L) after some of the $G\alpha_{13}$ (Q226L) protein slowly hydrolyzed bound GTP. Indeed, co-immunoprecipitation of endogenous Rac and $G\alpha_{13}$ could be observed after PDGF stimulation (FIG. 7F). Hence, these data demonstrate that Rac and $G\alpha_{13}$ form a complex in cells.

Example 6

Figure 8A:
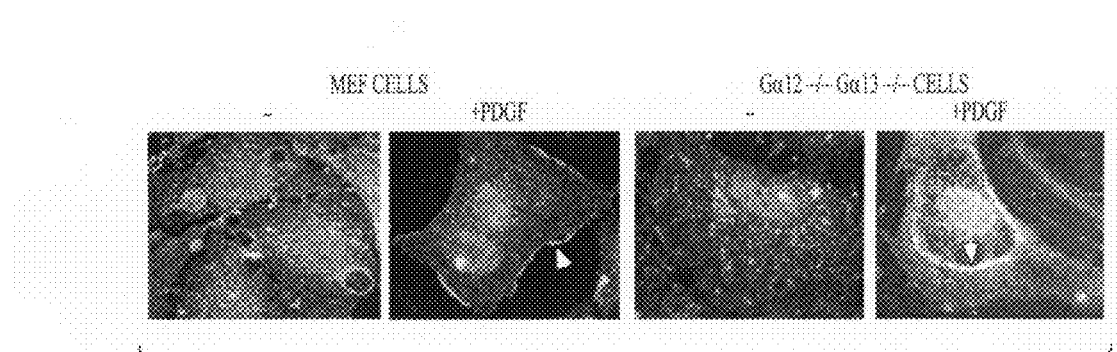
FIG. 8. Subcellular localization of Rac. A. Subcellular localization of Rac in MEF cells and in Gα$_{12}$$^{-/-}$Gα$_{13}$$^{-/-}$ cells, without or with PDGF treatment. B. Subcellular localization of cortactin in MEF cells and in Gα$_{12}$$^{-/-}$Gα$_{13}$$^{-/-}$ cells, without or with PDGF treatment. C. Subcellular localization of F-actin polymers in MEF cells and in Gα$_{12}$$^{-/-}$Gα$_{13}$$^{-/-}$ cells, without or with PDGF treatment. Data are representative of three to five experiments.
Figure 8B:
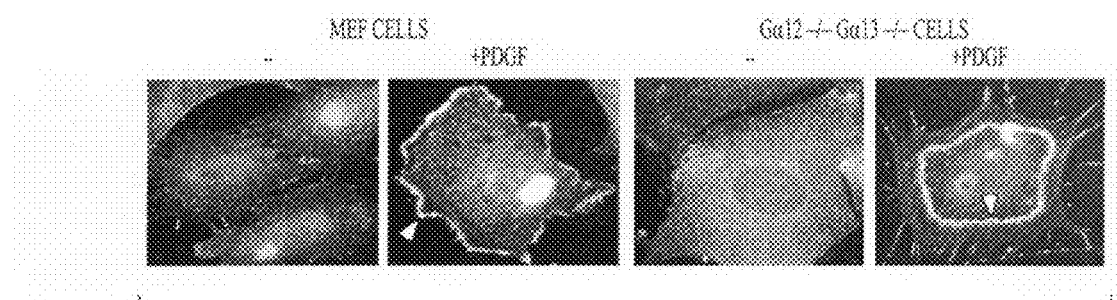
Figure 8C:
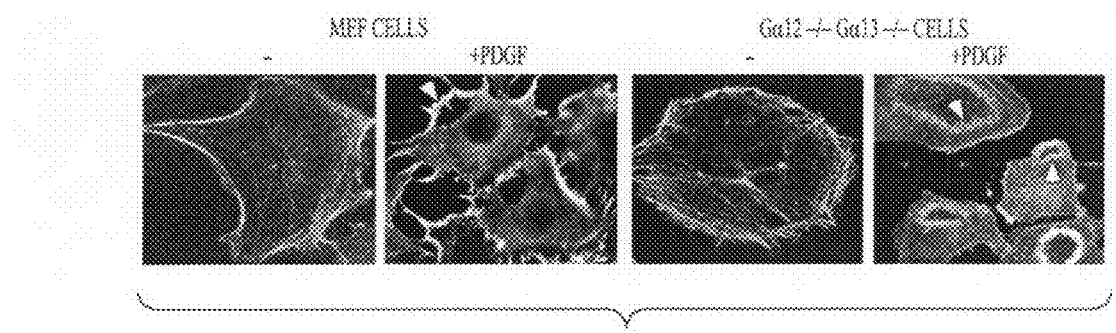

Deficiency of $G\alpha_{13}$ Blocks PDGF-Induced Membrane Ruffling and Lamellipodia Formation Next the physiological consequence of the Rac and $G\alpha_{13}$ interaction was examined. First, testes were performed to examine whether purified Rac1 or $G\alpha_{13}$ proteins could affect each other's guanine nucleotide exchange or GTPase activity. No significant changes in these activities were examined. Second, the subcellular localization of Rac in the presence or absence of $G\alpha_{13}$ was examined. In wild-type MEF cells, PDGF treatment induced Rac translocation to membrane ruffles and lamellipodia at the cell periphery (80-90% of the cells) (FIG. 8A). Membrane ruffles and lamellipodia are protruding membrane structures at the cell edge that are essential for cell migration (Hall, Science 279: 509-514 (1998)). Strikingly, Rac was localized away from the peripheral membrane edge in $G\alpha_{12}^{-/-}G\alpha_{13}^{-/-}$ cells after PDGF treatment (FIG. 8A). Instead, Rac was localized on the dorsal (top) surface of the cells forming a ring structure (called dorsal ruffles) (in ~90% of the cells) (FIG. 8A). To confirm this altered Rac localization in $G\alpha_{12}^{-/-}G\alpha_{13}^{-/-}$ cells, the subcellular localization of cortactin was determined. Cortactin is a cytoplasmic protein that is recruited by activated Rac to membrane ruffles and lamellipodia, where cortactin stimulates Arp2/3-mediated actin polymerization (Weed et al., J Cell Sci 111 (Pt 16): 2433-2443 (1998)). As shown in FIG. 8B, in MEF cells PDGF stimulation translocated cortactin from the cytosol to membrane ruffles and lamellipodia; whereas in $G\alpha_{12}^{-/-}G\alpha_{13}^{-/-}$ cells, cortactin was localized in the dorsal ruffles after PDGF addition. The cortactin staining patterns were similar to those of Rac, consistent with the altered subcellular localization of Rac in $G\alpha_{12}^{-/-}G\alpha_{13}^{-/-}$ cells. Furthermore, the localization of F-actin polymers was studied (FIG. 8C). Similar to the localization of Rac and cortactin, F-actin polymers were also found in membrane ruffles and lamellipodia in MEF cells and in dorsal ruffles in $G\alpha_{12}^{-/-}G\alpha_{13}^{-/-}$ cells (FIG. 8C). Since Rac mediates the PDGF-induced formation of both dorsal ruffles and lamellipodia (Buccione et al., Nat Rev Mol Cell Biol 5: 647-657 (2004)), the accumulation of dorsal ruffles in $G\alpha_{12}^{-/-}G\alpha_{13}^{-/-}$ cells could be explained if $G\alpha_{13}$ were required for breaking down dorsal ruffles so that actin and other components could be recycled to form lamellipodia. If that were the case, it would provide a mechanism by which $G\alpha_{13}$ regulates PDGF-induced cell migration.

Example 7

Role of $G\alpha_{13}$ in Tumor Angiogenesis

Figure 9A:
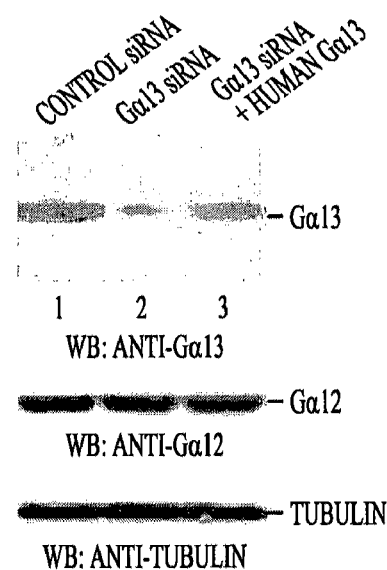
FIG. 9. Role of Gα$_{13}$ in tumor angiogenesis. A. Western blots were performed with whole cell extracts prepared from mouse endothelial SVEC4-10 cells treated with control siRNA, Gα$_{13}$ siRNA, or cells transfected with both Gα$_{13}$ siRNA and wild-type human Gα$_{13}$. B. Chamber assay of VEGF-induced migration of mouse endothelial SVEC4-10 cells treated with control siRNA, Gα$_{13}$ siRNA, or cells transfected with both Gα$_{13}$ siRNA and wild-type human Gα$_{13}$. Results are the mean±s.d. of three independent chambers. C. B-16 mouse melanoma tumor growth in Gα$_{13}$$^{+/-}$ mice and wild-type littermates. Each group consisted often mice. D. LLC tumor growth in Gα$_{13}$$^{+/-}$ mice and wild-type littermates. Each group consisted often mice. E. Hematoxylin and eosin staining of tumor xenografts (Left: wild-type littermate and Right: Gα$_{13}$$^{+/-}$). F. Representative pictures of anti-PECAM staining of sections of tumor xenografts from wild-type littermates (Left) or from Gα$_{13}$$^{+/-}$ mice (Right). G. Representative pictures of anti-VEGFR2 staining of sections of tumor xenografts from wild-type littermates (Left) or from Gα$_{13}$$^{+/-}$ mice (Right).
Figure 9B:
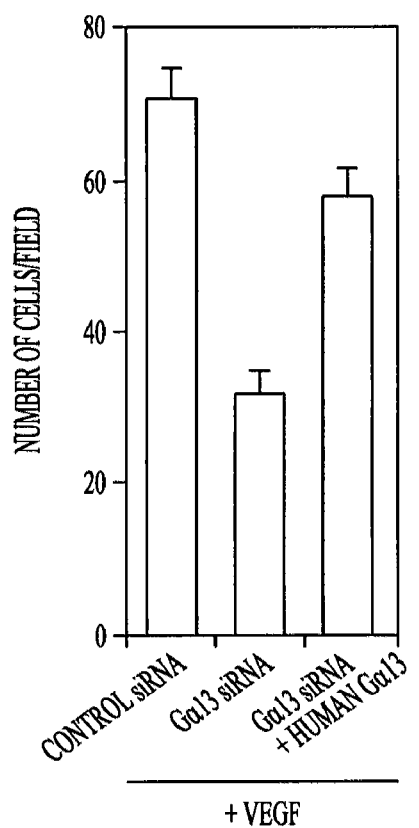
Figure 9C:
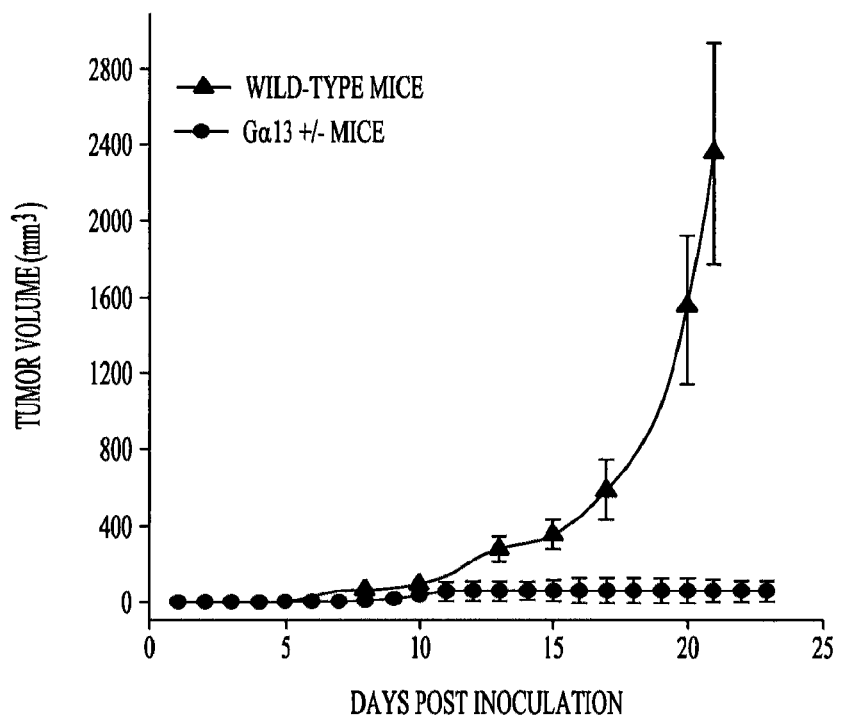

To investigate the role of $G\alpha_{13}$ in RTK-induced migration of other cell types, endothelial cell migration induced by VEGF was examined. As shown in FIG. 9A, treatment of mouse endothelial cells (SVEC4-10 cells) with $G\alpha_{13}$ siRNA reduced the endogenous mouse $G\alpha_{13}$ protein level, but had no effect on the protein levels of $G\alpha_{12}$ and tubulin. This treatment also reduced VEGF-induced endothelial cell migration (FIG. 9B). A control siRNA had no effect on the $G\alpha_{13}$ protein level or cell migration (FIGS. 9, A and B). Re-expression of the human $G\alpha_{13}$ gene in these $G\alpha_{13}$ siRNA transfected cells restored the migratory response to VEGF (FIGS. 9, A and B). These data show that $G\alpha_{13}$ is also involved in VEGF-induced endothelial cell migration.

Figure 9D:
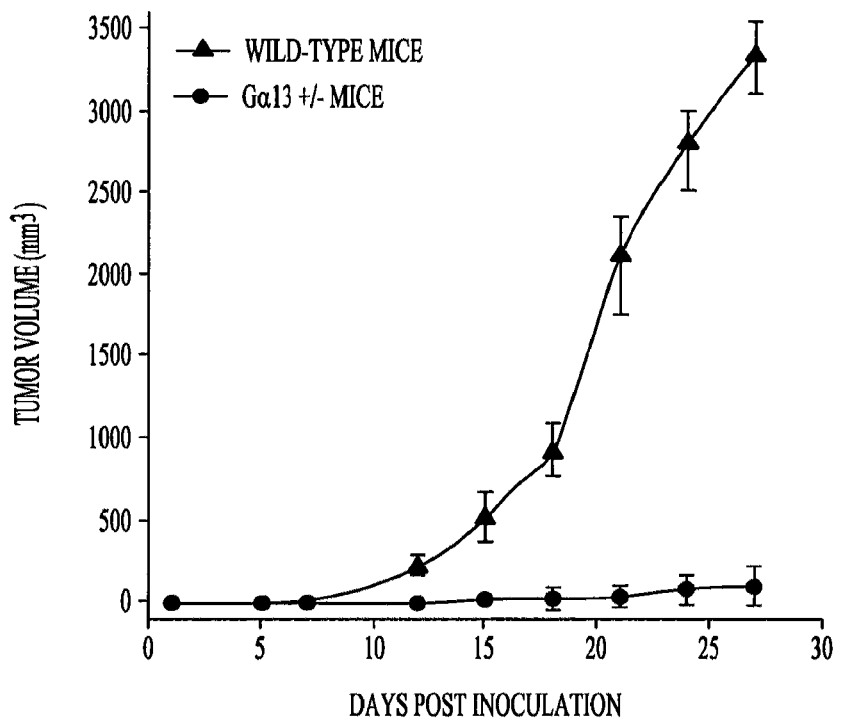

Next, to investigate the role of $G\alpha_{13}$ in RTK signaling in an animal model, tumor angiogenesis using a tumor xenograft mouse model was employed. Several RTKs including VEGF, PDGF, and angiopoietins play critical roles in developmental angiogenesis as well as in tumor angiogenesis (Risau, Nature 386: 671-674 (1997); Yancopoulos et al., Nature 407: 242-248 (2000)). Following a similar strategy used by Lyden et al., Nature 401: 670-677 (1999), the $G\alpha_{13}$ heterozygous knockout mouse was examined for their ability to support the growth of tumor xenografts. In these studies, mouse melanoma B16 tumor cells (FIG. 9C) or Lewis lung carcinoma (LLC) cells (FIG. 9D) were intradermally injected into host mice. Since $G\alpha_{13}^{-/-}$ mouse embryos died at ~E9.5, $G\alpha_{13}^{+/-}$ mice were used as host mice. The hypothesis was that mice with reduced $G\alpha_{13}$ gene dosages might not be able to support neo-angiogenesis of xenografted tumors as in the case of Id genes (Lyden et al., Nature 401: 670-677 (1999)). Although $Id1^{+/-}$ and $Id1^{+/-}Id3^{-/-}$ mice were indistinguishable from the wild-type mice, neither of these heterozygous mice could support the neo-vascularization of xenografted tumors (Lyden et al., Nature 401: 670-677 (1999)). Melanoma B16 tumor cells or LLC tumor cells were intradermally injected into $G\alpha_{13}^{+/-}$ mice and wild-type littermates. Wild-type mice had a rapid increase in tumor mass and died at 21±4 days (mean±s.d.) (FIG. 9C) or at 26±2 days (FIG. 9D). Significantly, the implanted tumors failed to grow on $G\alpha_{13}^{+/-}$ mice (FIGS. 9 C and D). Moreover, all $G\alpha_{13}^{+/-}$ mice remained healthy for more than 300 days until they were euthanized. These data demonstrate that reduced $G\alpha_{13}$ dosage inhibits tumor growth.

To obtain supportive evidence for the failed tumor angiogenesis in $G\alpha_{13}^{+/-}$ host mice, histological analysis and immunohistochemistry were performed. LLC tumor tissues were removed 8 days after inoculation from some wild-type and $G\alpha_{13}^{+/-}$ host mice, sectioned and stained with hematoxylin and eosin (FIG. 9E), with anti-PECAM/CD31 antibody (FIG. 9F), or with anti-VEGFR2 antibody (FIG. 9G). There were profound differences in the number of endothelial cells and of blood vessels in the tumor tissues from wild-type and $G\alpha_{13}^{+/-}$ host mice. In wild-type host mice, tumors showed plenty of well-defined large vessels (FIG. 9F, two left panels), whereas in $G\alpha_{13}^{+/-}$ mice, the tumors showed far less and stunted, occluded vessels (FIG. 9F, two right panels). Tumors from wild-type host mice showed intense staining with anti-VEGFR2 antibody, while tumors from $G\alpha_{13}^{+/-}$ host mice showed few cells stained with VEGFR2, indicating a possible defect in the recruitment of endothelial progenitor cells and/or endothelial cells into the tumors in $G\alpha_{13}^{+/-}$ host mice (FIG. 9G). This impaired recruitment could lead to few blood vessels in the tumors from $G\alpha_{13}^{+/-}$ host mice, which in turn could account for defective tumor angiogenesis and tumor growth in $G\alpha_{13}^{+/-}$ host mice. Hence, these data clearly showed a defect in tumor angiogenesis in $G\alpha_{13}^{+/-}$ host mice.

Example 8

Role of $G\alpha_{12}$ in Tumor Growth

Figure 10:
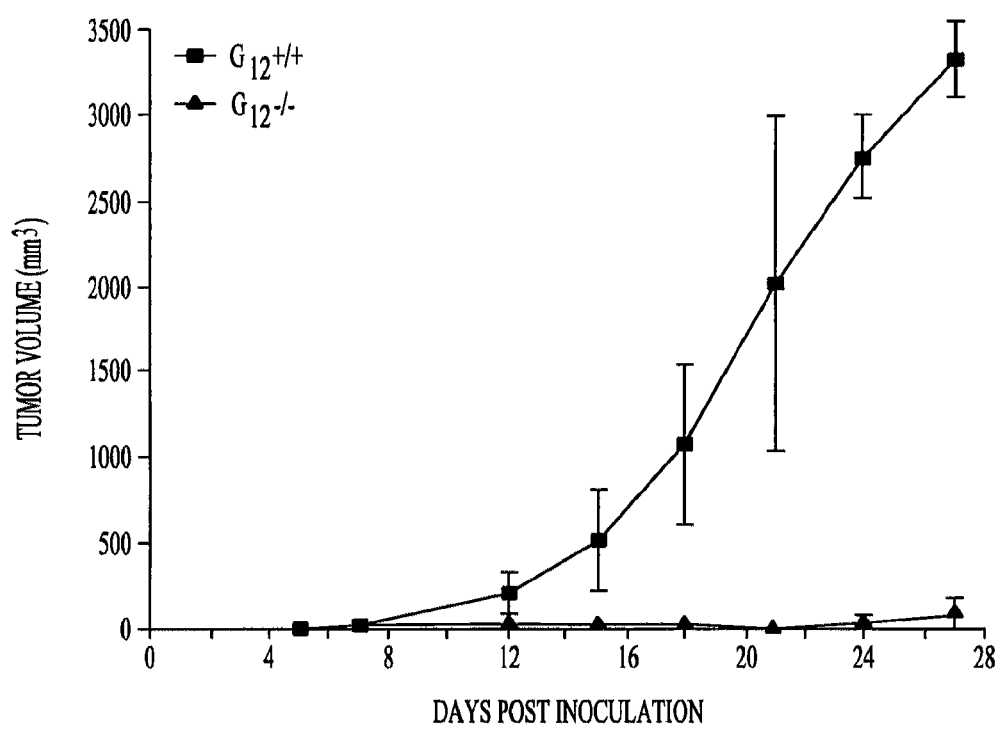
FIG. 10 is a graph illustrating the importance of Gα$_{12}$ in tumor growth.

Lewis lung carcinoma (LLC) cells ($2 \times 10^6$ cells/mouse) were intradermally injected into wild-type ($G\alpha_{12}^{+/+}$) or $G\alpha_{12}^{-/-}$ mice. While tumors grew rapidly in wild-type mice, they failed to grow significantly in $G\alpha_{12}^{-/-}$ mice (FIG. 10). All wild-type mice died before Day 27. All $G\alpha_{12}^{-/-}$ mice remained alive for more than 300 days until they were euthanized.

OTHER EMBODIMENTS

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for inhibiting angiogenesis in a mammal, the method comprising inhibiting the expression and/or activity of $G\alpha_{13}$ in the mammal by administering a guanine diphosphate or guanine triphosphate analogue selected from the group consisting of GDP beta S, GppNHp, and GppCH2p, with a small interfering RNA capable of hybridizing to a nucleic acid encoding a $G\alpha_{13}$ polypeptide under intracellular conditions and reducing expression of the $G\alpha_{13}$ protein in a cell, or any combination thereof in an amount effective to decrease expression and/or activity of the $G\alpha_{13}$ polypeptide.

2. The method of claim 1, wherein the small interfering RNA has a sequence selected from the group consisting of SEQ ID NO: 6-9 and 69-145.

3. The method of claim 1, wherein the mammal has cancer.

4. The method of claim 1, wherein the small interfering RNA, analogue or any combination thereof is administered by direct injection to a localized area.

5. The method of claim 1, wherein the expression and/or activity of $G\alpha_{12}$ or $G\alpha_{13}$ is decreased by about 20% to about 90%.

6. The method of claim 1 wherein the expression and/or activity of $G\alpha_{12}$ or $G\alpha_{13}$ is decreased by about 30% to about 70%.

7. The method of claim 1, wherein the method further comprises inhibiting endothelial cell migration.

8. A method for inhibiting angiogenesis in a mammal, the method comprising inhibiting the expression and/or activity of $G\alpha_{13}$ in the mammal by administering a small interfering RNA having a sequence selected from the group consisting of SEQ ID NO: 6-9 and 69-145, or a complement thereof.

9. The method of claim 8, further comprising administering a small interfering RNA having a sequence selected from the group consisting SEQ ID NO: 11-68.

10. A method for inhibiting angiogenesis in a mammal, the method comprising administering an antibody and a small interfering RNA having a sequence selected from the group consisting of SEQ ID NO: 6-9 and 69-145.

11. The method of claim 10, wherein the antibody reduces angiogenesis.

12. The method of claim 10, wherein the antibody binds to the $G\alpha_{13}$ polypeptide.

* * * * *

```
                         SEQUENCE LISTING

<160> NUMBER OF SEQ ID NOS: 163

<210> SEQ ID NO 1
<211> LENGTH: 4398
<212> TYPE: DNA
<213> ORGANISM: Homo sapiens

<400> SEQUENCE: 1
gggcgacgag tgcgggcctc ggagcgactg cagcggcggc ggcggacgcg gcctgaggcg      60
agcggcgggg cgtggggcgg tgcctcggcc cgggctcgcc ctcgccggcg ggagcgtcca     120
tggcccccgg gcgccggcgg ggcgcggccg cggcctgagg ggccatgtcc ggggtggtgc     180
ggaccctcag ccgctgcctg ctgccggccg aggccggcgg ggcccgcgag cgcagggcgg     240
gcagcggcgc gcgcgacgcg gagcgcgagg cccggaggcg tagccgcgac atcgacgcgc     300
tgctggcccg cgagcggcgc gcggtccggc gcctggtgaa gatcctgctg ctgggcgcgg     360
gcgagagcgg caagtccacg ttcctcaagc agatgcgcat catccacggc cgcgagttcg     420
accagaaggc gctgctggag ttccgcgaca ccatcttcga caacatcctc aagggctcaa     480
gggttcttgt tgatgcacga gataagcttg gcattccttg gcagtattct gaaaatgaga     540
agcatgggat gttcctgatg gccttcgaga caaggcggg gctgcctgtg gagccggcca     600
ccttccagct gtacgtcccg gccctgagcg cactctggag ggattctggc atcagggagg     660
ctttcagccg gagaagcgag tttcagctgg gggagtcggt gaagtacttc ctggacaact     720
tggaccggat cggccagctg aattactttc ctagtaagca agatatcctg ctggctagga     780
aagccaccaa gggaattgtg gagcatgact tcgttattaa gaagatcccc tttaagatgg     840
tggatgtggg cggccagcgg tcccagcgcc agaagtggtt ccagtgcttc gacgggatca     900
cgtccatcct gttcatggtc tcctccagcg agtacgacca ggtcctcatg gaggacaggc     960
gcaccaaccg gctggtggag tccatgaaca tcttcgagac catcgtcaac aacaagctct    1020
tcttcaacgt ctccatcatt ctcttcctca acaagatgga cctcctggtg gagaaggtga    1080
agaccgtgag catcaagaag cacttcccgg acttcagggg cgacccgcac aggctggagg    1140
acgtccagcg ctacctggtc cagtgcttcg acaggaagag acggaaccgc agcaagccac    1200
tcttccacca cttcaccacc gccatcgaca ccgagaacgt ccgcttcgtg ttccatgctg    1260
tgaaagacac catcctgcag gagaacctga aggacatcat gctgcagtga gcgaggaagc    1320
cccggggttt gtcgtcgttg agcagccccc acggctgtcg gtcagactct tgggtgtgtg    1380
ttgtctgtgt ggtccttgag tgggtttctc ggatccgtgc cctggaatac ctggctcagg    1440
aatgctgtca gaccagccag ccagcgagct ctaggcaaaa ggacatggaa actgtcacgt    1500
tagctactga atcctgggg cgagtgaaac tactgaaaat ccgagtgatg atgttgtgaa    1560
tacggaacac ctaatcacac agcttgcttt gcttttacag aaacgttcct cttttctga    1620 cgcagtttaa ttgaggaccg tgttgtgtgt gtatgtgtgt acacacgctc tgtctttaat    1680
gacagaaaca caaaaccag ctggccttgc agacggcttt tctaactcac aagtcttccc    1740
tgagacagac taacctgaaa gctttgccta acagtagctt gtagagatcc agtgcacgcc    1800
gatgctgcta aactcagtgc ctgagcccgg ccctgcagcc ccagccgcag tgtctgaagg    1860
```

-continued

```
ccacctccca aagggagcac gttgccttt caaactcccg tgccgatttc ctaagagccc    1920
ctagtccaag cctctcagat gaagctgagg agccgtgcct aggatccctt cccagctctg    1980
aggacgggct gcagagctct gcaggtgtgg attcaccta cgcccctaca gcaggctcag    2040
cccttcccac cctgccccat gcccagcagc acaaacggga gtgagacagg atgcccacgg    2100
tgactgccgc tccgtccgtg cacacacagc ggtgctcttc tcccttagc cacccactgc    2160 ccaacccaac ggcaaagaca cagaaaccag gtccccttgc agacggctct cccatcttcc    2220
tgcaagtcat ctgctcacac acagttggca gcacatagcg tttccttctt tcagaaacat    2280
tcctcttctg gggcttcaga aagctggcaa ggccactagc agagcttttg ttaatgcccc    2340
agctgcttgg cgagctaaca gctgacccttt cgggaagccc acagacgctg gaggaatctt    2400
gagtttctcc aaactgccgc tccaccagtg cctttggaca gccgtgcctg ttcgccgctc    2460
tccctaagtc tgattctcat cgaggcccct cgcttctatg actgtgcttg cagaagagta    2520
aacactctcg gatgccgctg tcctgggga gcccgcggga gcctgtgaat gttgatacga    2580
gctggccagt cctgggccca gctcacttgt ccagctacct gccaggtggc tttcactgtg    2640
tttaaaatac attgcattcc aagctggtcc cctctgtgta tcactctact gagaaatcct    2700
gcctagtgtg ttttgggatg tgtcctagca tttacaagaa aatgaaaagc gtcctcttaa    2760
ttggcacccg aatgttgctg tggctcagtc acatatccca gggccctcgt cccgaggccg    2820
tgctgccccg agcccgagc ccctctgcag ctcacccttg gcttgttttc cgcaaacccg    2880
gtaaacgcaa gcccttgggg cagatgcaga agcagaagag ggaggggaaa cctgcctctg    2940
ggtcaccctg ttagcacagc gttctcatcg ggagacagca tggaactctc tctcgcagtg    3000
ctcgaggctg tgtgtcagtg tttgctgggc ttgtggctcc tttttttggct ggataaagaa    3060 gtcgctgttt ttgtactgct tctgtggctc ttcacagacc tcacgatgt gaccggagat    3120 gagtgccgat gaccacgttt taaaggagaa agagagctcc tggtggggcc ctcggggtgg    3180
tctcaggtcc catttgcagt ctgcaacagt gacgcgcagc ccggtccgga gcgtggtgag    3240
ctttgtttgc cttctgggtc agcttcgct gtgtctcctg tgtgtgttag aatccagagc    3300
ccagaggaag tgcaagcggg tcctccgcca acggggagag cctcttcgcg cgctgttgg    3360 cgacagcagc gctgtgattc gcgtagcagg ggagttgttt gaaacacctt cctgagtagt    3420
ccggccttgt caatgagtgc ttgttttcct ttaaacagtc tgacatattt actcgtcact    3480
ttcaaaccag aagcatgaga ggaaggagat attgtggggt ccgtttaact cgatagaaag    3540
cgcaggggga tggcccccgg cgcgggctct tgacccgctc agcgctgacc ccaccgccct    3600
ggccgaggca cttggccttg ctgagctgga cttcctcctc ctcctcctca tgaccggggt    3660
gaattagaac gttttaaag acacccccctt ccaaattctg taacacattg taattgggaga    3720 agaaggaaac tctgcaaggc taaactgtca ttcacaactt ggctacacat agactctagt    3780 cagtttttgtc tccagaacct taggcttttg tattttttaa ttttaatttc actgttaatc    3840
cttattgtct tttttattaa gatgttggaa aagcaggagg tagttgtgcc tcaattattg    3900
caaaaatgta acaataaagt tcctcaaaat aagatctgtt cctcatagct atactgtgta    3960
cacataagac gcataaggg ttttactgaa atctattttt aactcttatg ttcgtagaga    4020
aattgtttca aggattttga gtcataggtc tgtaatttat agagatctct agaattctta    4080
ttgtaatttt cctacttctt tgataaaaga aaaataagtc agattgttaa ctccaagatt    4140
gaaaaaaaaa actcttgaaa gaagattatt agttgtaact aatttagggg ttctgggcac    4200
agacatctaa cctggtattg taaggcagag gctcccattg gaatggtagt ggtccgggtc    4260
```

```
agttgttcat ggtgtaagct ttgcacagtg tattaacatt gggagggtct ggcttgaaaa    4320
tttggccacc ctcagcctct gaatgtttat taaataaat  ttagtctttc tttgcttaat    4380 ataaaaaaa  aaaaaaaa                                                  4398
```

<210> SEQ ID NO 2
<211> LENGTH: 381
<212> TYPE: PRT
<213> ORGANISM: Homo sapiens

<400> SEQUENCE: 2

```
Met Ser Gly Val Val Arg Thr Leu Ser Arg Cys Leu Leu Pro Ala Glu
 1               5                  10                  15

Ala Gly Gly Ala Arg Glu Arg Arg Ala Gly Ser Gly Ala Arg Asp Ala
             20                  25                  30

Glu Arg Glu Ala Arg Arg Ser Arg Asp Ile Asp Ala Leu Leu Ala
         35                  40                  45

Arg Glu Arg Arg Ala Val Arg Leu Val Lys Ile Leu Leu Leu Gly
 50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                 85                  90                  95

Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
    130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Arg Ser Glu Phe Gln Leu Gly
                165                 170                 175

Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
        195                 200                 205

Lys Gly Ile Val Glu His Asp Phe Val Ile Lys Lys Ile Pro Phe Lys
    210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350
```

```
Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
        370                 375                 380

<210> SEQ ID NO 3
<211> LENGTH: 4744
<212> TYPE: DNA
<213> ORGANISM: Homo sapiens

<400> SEQUENCE: 3
ccacgcgtcc gggagccgg agggccccgc cgaggcggcg gcggcggcgg caagatggcg      60
gacttcctgc cgtcgcggtc cgtgctgtcc gtgtgcttcc ccggctgcct gctgacgagt     120
ggcgaggccg agcagcaacg caagtccaag gagatcgaca atgcctgtc tcgggaaaag     180 acctatgtga agcggctggt gaagatcctg ctgctgggcg cgggcgagag cggcaagtcc     240
accttcctga agcagatgcg gatcatccac gggcaggact cgaccagcg cgcgcgcgag     300 gagttccgcc ccaccatcta cagcaacgtg atcaaggta tgagggtgct ggttgatgct     360
cgagagaagc ttcatattcc ctggggagac aactcaaacc aacaacatgg agataagatg     420
atgtcgtttg ataccccggc ccccatggca gcccaaggaa tggtggaaac aagggttttc     480
ttacaatatc ttcctgctat aagagcatta tgggcagaca gcggcataca gaatgcctat     540
gaccggcgtc gagaatttca actgggtgaa tctgtaaaat atttcctgga taacttggat     600
aaacttggag aaccagatta tattccatca caacaagata ttctgcttgc cagaagaccc     660
accaaaggca tccatgaata cgactttgaa ataaaaaatg ttcctttcaa aatggttgat     720
gtaggtggtc agagatcaga aaggaaacgt tggtttgaat gtttcgacag tgtgacatca     780
atacttttcc ttgtttcctc aagtgaattt gaccaggtgc ttatgaaga tcgactgacc     840 aatcgcctta cagagtctct gaacattttt gaaacaatcg tcaataaccg ggttttcagc     900
aatgtctcca taattctgtt cttaaacaag acagacttgc ttgaggagaa ggtgcaaatt     960
gtgagcatca aagactattt cctagaattt gaagggatc cccactgctt aagagacgtc    1020
caaaaattcc tggtggaatg tttccggaac aaacgccggg accagcaaca gaagccctta    1080
taccaccact tcaccactgc tatcaacacg gagaacatcc gccttgtttt ccgtgacgtg    1140
aaggatacta ttctgcatga caacctcaag cagcttatgc tacagtgatg tacaaaagac    1200
ttgctgtttt aatatctttt tgtgtttttg atgttttctg tttgttttgt tttttaaaat    1260
agcagtttac aaccagaatt agaacaatct taattctacg tttaacttct tgaaaatctt    1320 agtactttt ctgcggcctt tggtttgtgg ctgaaagctg ttgagtgact catcgccaag    1380
atttgctgta atgcaggctt tgatctgttt caccatggct tctattcaag tccagttaaa    1440
acctcccagc tgacctcaga ctaggcatat ttcaggcttt aaattattct actttccaaa    1500
ctgaattctc ctgcagtgcc aagtatcaaa ggtgtcctta atacttgta gggatgaggt     1560 taggaatatt cagttccaaa acaagatatc ttctgtccgc cttacatata gcagtgacac    1620
ttgttgccta actttatggt gacctcctat tttgtaaggg ctgttagaag ttctatctaa    1680
gaaatggcat tctgtaggtt tatagaaggt ttagccttca tattttaatt gcttgtatac    1740
acaacagctg ttttgctttt agatttctgt gtttctgaag gtaatgttct tcctgttttc    1800
aagtttacat aaggatcttt ggtctgatgc tgatgaagag ttcacaggtg gtatgggaga    1860
gcaaaaggca agctaatgct gtttaccgtg ttttggtcaa acgtaacgag tgaaatagaa    1920
tttgcctttc tcatatttaa ttatcatgta gtttaatgta ccatatgtga aacattctgg    1980
```

```
ccatagcagc aactaaaaac tgcaagcaac ttggtaacag aactttctaa ataaacttaa    2040
cctgttccag aatgtcatgt atttgacttt taagccctat ctcagttggt cagtaaagac    2100
caatccttac tgtaggaaat cattgttgta tcatcacaaa catctatctt ttgctgtcct    2160
gtccagtccc atcaactcca cactgtgcca tttgtggcat cgttttgttt atttggagtt    2220
tgctaagggc agtattttc tgtcaagact attcaagaag gcattatttg agattcctgt     2280
tcattcttgg tgtgtctcta acagatacag tatgtataca tttgtataat tgttgttgtt    2340
gaaagtccag ctttttgag gtatattta aatgtttaa ggatgcttct aaggatcagt       2400
agtaattttt ttagttcgca cctaaagatg attacattga cctcccccga ctgcttacca    2460
aattaaaatg tgtccacgaa gtagctttgt gatcgcagat acattcatag tgaactcatc    2520
agaatggctg gtttgcagta ctgaaatact atcttctagg ctgtatgtag tgctacaatt    2580
agagaaacag aagtccaagg ctggcgacag cttgaaaagt ctgacagctt ttctactttt    2640
cctgaaaatt ttaagactgt gatatctgtc attttactgt atagctgact gtgtactcag    2700
gtattttatt ggtccttgaa agattggtcg ttatggatca cccagccttt ccaagtcagt    2760
ggctgttgtt ctgtcttgct gtctgatacg agagtggggc ttttcagtga actaaccagg    2820
gattgttctt gacatacctg acttttctca catttgaact tccactatca ttgtatccat    2880
ataacttcta gcattttcat gccatggtaa tccatgagct acacatacgt agcccggcac    2940
cgtgatgcaa gttcatggta tcgtgcatgt tcgtggtatc atggtatcat tcatgcgtgt    3000
ttgaatagtt ctacatctag tgcttcttgc caaaaagaat acattgttta aattcacaaa    3060
attagcataa ttgcagtgct aatgaatatc ggaatatgtg cacagtaaca tttggactat    3120
tcattggaga gtttacccat acatttagca aattgaatgg ccaaaacatt tgactccagt    3180
gagggctcaa gttagatccc tatagaaaga ggacacttca tcttacttaa gtcatagtta    3240
agatctgtga tacgaaccat agatattgcc tgacaaagca gaaatcacca agtttccccc    3300
ttttgaatta ccaccaagaa gtgttgaaac accaaataga tatcatgtta ttttgggcat    3360
ttgcagtttt cttccctgct gcatgtaatg tctcagaatc aacattcttt taaaatctag    3420
actatatttt gaggcaatga attacttata ttcaacttag gcttgttttg acattcagta    3480
gaactttaag ttcaatctaa aggcttcagt ccacatttt ttatacgttg tattttaaaa     3540
acgtttgaaa ggagtcttac acctgtatca tgaaaactga atccttttga aataccacta    3600
tatgaagaga gagatgaaat ttagtgaaca gaattgaaaa ggtgctcata atttcactat    3660
gcaaacttac cccagtctct aaaaaagtaa tttagattta aagttctttg atgtatttga    3720
ttttctaaat ctttatggtt atgatttgga ataaaatgtg cctaatcctg tgttacattc    3780
tgttcttaaa tctgaatgcc ttctcattta attctgagga aatatcacac aagtgtcttc    3840
attgaccttg aagaaatgta tatacagttg ccttataaaa caacataaat ttagaccata    3900
acttttatag agaaagggtt ttgtcaaatg ttttctgaaa atctgagtaa ttcaaagcat    3960
gcctctgccc ctttaatatt tttaataacc tgcattgttg ctgtctgcca aatattaaat    4020
tgaaatcttc atttcaattt tattatctgg aaagggcact ggattgctct gcaaccaaag    4080
aaagcaatat ggaatgaaaa aactcattca cttttgtctt attttctttt aaggtgtatt    4140
ggcatgtaat ttgcatagag aaggtcctct ggttagtctc tcaaattgag gctgtttagg    4200
gaaatcctta ttcagttggt ggcagtggtt ggtttaaagt agaaggaaat aagatcgcct    4260
taataccaga aatgattaga agtgctgatt tagattcaac aaataccata tgtccttatc    4320
attttttgta agaagaaatt ggttaagtcc taactttcaa tgtgtaccca aatacttgta    4380
```

-continued

```
tttatgcttt tgataaaatg tattttcagc attaatacac atccgattat gccttattta   4440
tatatgaaga ataagttac catgttatac tgttatgtcc taaaattcaa atcactattt    4500
gagaaaccct caaattggtg ctttcattat ataatgatac atttagacaa accccaaac    4560 taagccattt gaaacaagat tctctccatt gcagtttgta gcaatgttat ttctgtgtat   4620
gtcatgagaa ggctaaatat cagtgttaat ttcttgtttg aatccgtgaa atcatgcctg   4680
taaagcccaa acatttgtaa caaactccct aataaattta gagaaagtca aaaaaaaaa    4740 aaaa                                                                4744
```

<210> SEQ ID NO 4
<211> LENGTH: 377
<212> TYPE: PRT
<213> ORGANISM: Homo sapiens

<400> SEQUENCE: 4

```
Met Ala Asp Phe Leu Pro Ser Arg Ser Val Leu Ser Val Cys Phe Pro
 1               5                  10                  15

Gly Cys Leu Leu Thr Ser Gly Glu Ala Glu Gln Gln Arg Lys Ser Lys
            20                  25                  30

Glu Ile Asp Lys Cys Leu Ser Arg Glu Lys Thr Tyr Val Lys Arg Leu
        35                  40                  45

Val Lys Ile Leu Leu Leu Gly Ala Gly Glu Ser Gly Lys Ser Thr Phe
    50                  55                  60

Leu Lys Gln Met Arg Ile Ile His Gly Gln Asp Phe Asp Gln Arg Ala
65                  70                  75                  80

Arg Glu Glu Phe Arg Pro Thr Ile Tyr Ser Asn Val Ile Lys Gly Met
                85                  90                  95

Arg Val Leu Val Asp Ala Arg Glu Lys Leu His Ile Pro Trp Gly Asp
            100                 105                 110

Asn Ser Asn Gln Gln His Gly Asp Lys Met Met Ser Phe Asp Thr Arg
        115                 120                 125

Ala Pro Met Ala Ala Gln Gly Met Val Glu Thr Arg Val Phe Leu Gln
    130                 135                 140

Tyr Leu Pro Ala Ile Arg Ala Leu Trp Ala Asp Ser Gly Ile Gln Asn
145                 150                 155                 160

Ala Tyr Asp Arg Arg Arg Glu Phe Gln Leu Gly Glu Ser Val Lys Tyr
                165                 170                 175

Phe Leu Asp Asn Leu Asp Lys Leu Gly Glu Pro Asp Tyr Ile Pro Ser
            180                 185                 190

Gln Gln Asp Ile Leu Leu Ala Arg Arg Pro Thr Lys Gly Ile His Glu
        195                 200                 205

Tyr Asp Phe Glu Ile Lys Asn Val Pro Phe Lys Met Val Asp Val Gly
    210                 215                 220

Gly Gln Arg Ser Glu Arg Lys Arg Trp Phe Glu Cys Phe Asp Ser Val
225                 230                 235                 240

Thr Ser Ile Leu Phe Leu Val Ser Ser Ser Glu Phe Asp Gln Val Leu
                245                 250                 255

Met Glu Asp Arg Leu Thr Asn Arg Leu Thr Glu Ser Leu Asn Ile Phe
            260                 265                 270

Glu Thr Ile Val Asn Asn Arg Val Phe Ser Asn Val Ser Ile Ile Leu
        275                 280                 285

Phe Leu Asn Lys Thr Asp Leu Leu Glu Glu Lys Val Gln Ile Val Ser
    290                 295                 300

Ile Lys Asp Tyr Phe Leu Glu Phe Glu Gly Asp Pro His Cys Leu Arg
```

```
                305                 310                 315                 320
Asp Val Gln Lys Phe Leu Val Glu Cys Phe Arg Asn Lys Arg Arg Asp
                    325                 330                 335

Gln Gln Gln Lys Pro Leu Tyr His His Phe Thr Thr Ala Ile Asn Thr
                340                 345                 350

Glu Asn Ile Arg Leu Val Phe Arg Asp Val Lys Asp Thr Ile Leu His
            355                 360                 365

Asp Asn Leu Lys Gln Leu Met Leu Gln
        370                 375

<210> SEQ ID NO 5
<211> LENGTH: 21
<212> TYPE: PRT
<213> ORGANISM: Artificial Sequence
<220> FEATURE:
<223> OTHER INFORMATION: A synthetic peptide

<400> SEQUENCE: 5

Glu Gln Lys Leu Ile Ser Gly Gly Asp Leu Asn Met His Thr Glu His
 1               5                  10                  15

His His His His His
         20

<210> SEQ ID NO 6
<211> LENGTH: 21
<212> TYPE: DNA
<213> ORGANISM: Artificial Sequence
<220> FEATURE:
<223> OTHER INFORMATION: A synthetic oligonucleotide
<220> FEATURE:
<223> OTHER INFORMATION: A combined DNA/RNA

<400> SEQUENCE: 6
guacgacuuu gaaauuaaat t                                           21

<210> SEQ ID NO 7
<211> LENGTH: 21
<212> TYPE: DNA
<213> ORGANISM: Artificial Sequence
<220> FEATURE:
<223> OTHER INFORMATION: A synthetic oligonucleotide
<220> FEATURE:
<223> OTHER INFORMATION: A combined DNA/RNA

<400> SEQUENCE: 7
uuuaauuuca aagucguact c                                           21

<210> SEQ ID NO 8
<211> LENGTH: 21
<212> TYPE: DNA
<213> ORGANISM: Artificial Sequence
<220> FEATURE:
<223> OTHER INFORMATION: A synthetic oligonucleotide
<220> FEATURE:
<223> OTHER INFORMATION: A combined DNA/RNA

<400> SEQUENCE: 8
gggugagucu guaaaguaut t                                           21

<210> SEQ ID NO 9
<211> LENGTH: 21
<212> TYPE: DNA
<213> ORGANISM: Artificial Sequence
<220> FEATURE:
<223> OTHER INFORMATION: A synthetic oligonucleotide
<220> FEATURE:
```

```
<223> OTHER INFORMATION: A combined DNA/RNA

<400> SEQUENCE: 9
auacuuuaca gacucaccca g                                            21

<210> SEQ ID NO 10
<211> LENGTH: 9
<212> TYPE: RNA
<213> ORGANISM: Artificial Sequence
<220> FEATURE:
<223> OTHER INFORMATION: A synthetic oligonucleotide

<400> SEQUENCE: 10 uucaagaga                                                           9

<210> SEQ ID NO 11
<211> LENGTH: 23
<212> TYPE: RNA
<213> ORGANISM: Homo sapiens

<400> SEQUENCE: 11
aagcaugaga ggaaggagau auu                                          23

<210> SEQ ID NO 12
<211> LENGTH: 23
<212> TYPE: RNA
<213> ORGANISM: Homo sapiens

<400> SEQUENCE: 12
aagggaauug uggagcauga cuu                                          23

<210> SEQ ID NO 13
<211> LENGTH: 23
<212> TYPE: RNA
<213> ORGANISM: Homo sapiens

<400> SEQUENCE: 13
aaggacaugg aaacugucac guu                                          23

<210> SEQ ID NO 14
<211> LENGTH: 23
<212> TYPE: RNA
<213> ORGANISM: Homo sapiens

<400> SEQUENCE: 14
aaucacacag cuugcuuugc uuu                                          23

<210> SEQ ID NO 15
<211> LENGTH: 23
<212> TYPE: RNA
<213> ORGANISM: Homo sapiens

<400> SEQUENCE: 15
aaugguagug guccggguca guu                                          23

<210> SEQ ID NO 16
<211> LENGTH: 23
<212> TYPE: RNA
<213> ORGANISM: Homo sapiens

<400> SEQUENCE: 16
aagucaucug cucacacaca guu                                          23

<210> SEQ ID NO 17
```

```
<211> LENGTH: 23
<212> TYPE: RNA
<213> ORGANISM: Homo sapiens

<400> SEQUENCE: 17 aaagcuugc cuaacaguag cuu                                          23

<210> SEQ ID NO 18
<211> LENGTH: 23
<212> TYPE: RNA
<213> ORGANISM: Homo sapiens

<400> SEQUENCE: 18
aaacccggua aacgcaagcc cuu                                         23

<210> SEQ ID NO 19
<211> LENGTH: 23
<212> TYPE: RNA
<213> ORGANISM: Homo sapiens

<400> SEQUENCE: 19
cagccucuga auguuauua aaa                                          23

<210> SEQ ID NO 20
<211> LENGTH: 23
<212> TYPE: RNA
<213> ORGANISM: Homo sapiens

<400> SEQUENCE: 20
cagccggaga agcgaguuuc agc                                         23

<210> SEQ ID NO 21
<211> LENGTH: 23
<212> TYPE: RNA
<213> ORGANISM: Homo sapiens

<400> SEQUENCE: 21
gaggcugugu gucaguguuu gcu                                         23

<210> SEQ ID NO 22
<211> LENGTH: 23
<212> TYPE: RNA
<213> ORGANISM: Homo sapiens

<400> SEQUENCE: 22
gaccggaucg gccagcugaa uua                                         23

<210> SEQ ID NO 23
<211> LENGTH: 23
<212> TYPE: RNA
<213> ORGANISM: Homo sapiens

<400> SEQUENCE: 23
gagguaguug ugccucaauu auu                                         23

<210> SEQ ID NO 24
<211> LENGTH: 23
<212> TYPE: RNA
<213> ORGANISM: Homo sapiens

<400> SEQUENCE: 24
cagcugcuug gcgagcuaac agc                                         23

<210> SEQ ID NO 25
```

```
<211> LENGTH: 23
<212> TYPE: RNA
<213> ORGANISM: Homo sapiens

<400> SEQUENCE: 25
gagcggcaag uccacguucc uca                                              23

<210> SEQ ID NO 26
<211> LENGTH: 23
<212> TYPE: RNA
<213> ORGANISM: Homo sapiens

<400> SEQUENCE: 26
uacacacgcu cugucuuuaa uga                                              23

<210> SEQ ID NO 27
<211> LENGTH: 23
<212> TYPE: RNA
<213> ORGANISM: Homo sapiens

<400> SEQUENCE: 27
caagggcuca aggguucuug uug                                              23

<210> SEQ ID NO 28
<211> LENGTH: 23
<212> TYPE: RNA
<213> ORGANISM: Homo sapiens

<400> SEQUENCE: 28
gagcgcacuc uggagggauu cug                                              23

<210> SEQ ID NO 29
<211> LENGTH: 23
<212> TYPE: RNA
<213> ORGANISM: Homo sapiens

<400> SEQUENCE: 29
caccgccauc gacaccgaga acg                                              23

<210> SEQ ID NO 30
<211> LENGTH: 23
<212> TYPE: RNA
<213> ORGANISM: Homo sapiens

<400> SEQUENCE: 30
gagcguggug agcuuuguuu gcc                                              23

<210> SEQ ID NO 31
<211> LENGTH: 23
<212> TYPE: RNA
<213> ORGANISM: Homo sapiens

<400> SEQUENCE: 31
gagccuguga auguugauac gag                                              23

<210> SEQ ID NO 32
<211> LENGTH: 23
<212> TYPE: RNA
<213> ORGANISM: Homo sapiens

<400> SEQUENCE: 32
cagaggcucc cauuggaaug gua                                              23

<210> SEQ ID NO 33
```

```
<211> LENGTH: 23
<212> TYPE: RNA
<213> ORGANISM: Homo sapiens

<400> SEQUENCE: 33
gagucauagg ucuguaauuu aua                                               23

<210> SEQ ID NO 34
<211> LENGTH: 23
<212> TYPE: RNA
<213> ORGANISM: Homo sapiens

<400> SEQUENCE: 34
gagcaugacu ucguuauuaa gaa                                               23

<210> SEQ ID NO 35
<211> LENGTH: 23
<212> TYPE: RNA
<213> ORGANISM: Homo sapiens

<400> SEQUENCE: 35
caggagguag uugugccuca auu                                               23

<210> SEQ ID NO 36
<211> LENGTH: 23
<212> TYPE: RNA
<213> ORGANISM: Homo sapiens

<400> SEQUENCE: 36
gaggaccgug uugugugugu aug                                               23

<210> SEQ ID NO 37
<211> LENGTH: 23
<212> TYPE: RNA
<213> ORGANISM: Homo sapiens

<400> SEQUENCE: 37
caacggcaaa gacacagaaa cca                                               23

<210> SEQ ID NO 38
<211> LENGTH: 23
<212> TYPE: RNA
<213> ORGANISM: Homo sapiens

<400> SEQUENCE: 38
cagccagcca gcgagcucua ggc                                               23

<210> SEQ ID NO 39
<211> LENGTH: 23
<212> TYPE: RNA
<213> ORGANISM: Homo sapiens

<400> SEQUENCE: 39
aaccggcugg uggaguccau gaa                                               23

<210> SEQ ID NO 40
<211> LENGTH: 23
<212> TYPE: RNA
<213> ORGANISM: Homo sapiens

<400> SEQUENCE: 40
gaccguguug ugugugauaug ugu                                              23

<210> SEQ ID NO 41
```

```
<211> LENGTH: 23
<212> TYPE: RNA
<213> ORGANISM: Homo sapiens

<400> SEQUENCE: 41
aagcuuugca caguguauua aca                                              23

<210> SEQ ID NO 42
<211> LENGTH: 23
<212> TYPE: RNA
<213> ORGANISM: Homo sapiens

<400> SEQUENCE: 42
gaggcguagc cgcgacaucg acg                                              23

<210> SEQ ID NO 43
<211> LENGTH: 23
<212> TYPE: RNA
<213> ORGANISM: Homo sapiens

<400> SEQUENCE: 43
caggugugga uucaccuuac gcc                                              23

<210> SEQ ID NO 44
<211> LENGTH: 23
<212> TYPE: RNA
<213> ORGANISM: Homo sapiens

<400> SEQUENCE: 44
cacacgcucu gucuuuaaug aca                                              23

<210> SEQ ID NO 45
<211> LENGTH: 23
<212> TYPE: RNA
<213> ORGANISM: Homo sapiens

<400> SEQUENCE: 45
cagcacauag cguuccuuc uuu                                               23

<210> SEQ ID NO 46
<211> LENGTH: 23
<212> TYPE: RNA
<213> ORGANISM: Homo sapiens

<400> SEQUENCE: 46
cagacgcugg aggaaucuug agu                                              23

<210> SEQ ID NO 47
<211> LENGTH: 23
<212> TYPE: RNA
<213> ORGANISM: Homo sapiens

<400> SEQUENCE: 47
gagcccagag gaagugcaag cgg                                              23

<210> SEQ ID NO 48
<211> LENGTH: 23
<212> TYPE: RNA
<213> ORGANISM: Homo sapiens

<400> SEQUENCE: 48
caugagagga aggagauauu gug                                              23

<210> SEQ ID NO 49
```

```
<211> LENGTH: 23
<212> TYPE: RNA
<213> ORGANISM: Homo sapiens

<400> SEQUENCE: 49
aagaccguga gcaucaagaa gca                                             23

<210> SEQ ID NO 50
<211> LENGTH: 23
<212> TYPE: RNA
<213> ORGANISM: Homo sapiens

<400> SEQUENCE: 50
aagccacucu uccaccacuu cac                                             23

<210> SEQ ID NO 51
<211> LENGTH: 23
<212> TYPE: RNA
<213> ORGANISM: Homo sapiens

<400> SEQUENCE: 51
cagcugaauu acuuccuag uaa                                              23

<210> SEQ ID NO 52
<211> LENGTH: 23
<212> TYPE: RNA
<213> ORGANISM: Homo sapiens

<400> SEQUENCE: 52
gaccggagau gagugccgau gac                                             23

<210> SEQ ID NO 53
<211> LENGTH: 23
<212> TYPE: RNA
<213> ORGANISM: Homo sapiens

<400> SEQUENCE: 53
uaagcuuugc acaguguauu aac                                             23

<210> SEQ ID NO 54
<211> LENGTH: 23
<212> TYPE: RNA
<213> ORGANISM: Homo sapiens

<400> SEQUENCE: 54
cacccacugc ccaacccaac ggc                                             23

<210> SEQ ID NO 55
<211> LENGTH: 23
<212> TYPE: RNA
<213> ORGANISM: Homo sapiens

<400> SEQUENCE: 55
cagcgccaga agugguucca gug                                             23

<210> SEQ ID NO 56
<211> LENGTH: 23
<212> TYPE: RNA
<213> ORGANISM: Homo sapiens

<400> SEQUENCE: 56
cacgccgaug cugcuaaacu cag                                             23

<210> SEQ ID NO 57
```

```
<211> LENGTH: 23
<212> TYPE: RNA
<213> ORGANISM: Homo sapiens

<400> SEQUENCE: 57
aacggcaaag acacagaaac cag                                             23

<210> SEQ ID NO 58
<211> LENGTH: 23
<212> TYPE: RNA
<213> ORGANISM: Homo sapiens

<400> SEQUENCE: 58
uaguccggcc uugucaauga gug                                             23

<210> SEQ ID NO 59
<211> LENGTH: 23
<212> TYPE: RNA
<213> ORGANISM: Homo sapiens

<400> SEQUENCE: 59
gagaccaucg ucaacaacaa gcu                                             23

<210> SEQ ID NO 60
<211> LENGTH: 23
<212> TYPE: RNA
<213> ORGANISM: Homo sapiens

<400> SEQUENCE: 60
gagcucugca gguguggauu cac                                             23

<210> SEQ ID NO 61
<211> LENGTH: 23
<212> TYPE: RNA
<213> ORGANISM: Homo sapiens

<400> SEQUENCE: 61
caugcccagc agcacaacac gga                                             23

<210> SEQ ID NO 62
<211> LENGTH: 23
<212> TYPE: RNA
<213> ORGANISM: Homo sapiens

<400> SEQUENCE: 62
gaucacgucc auccuguuca ugg                                             23

<210> SEQ ID NO 63
<211> LENGTH: 23
<212> TYPE: RNA
<213> ORGANISM: Homo sapiens

<400> SEQUENCE: 63
gaagaccgug agcaucaaga agc                                             23

<210> SEQ ID NO 64
<211> LENGTH: 23
<212> TYPE: RNA
<213> ORGANISM: Homo sapiens

<400> SEQUENCE: 64
cagagcccag aggaagugca agc                                             23

<210> SEQ ID NO 65
```

```
<211> LENGTH: 23
<212> TYPE: RNA
<213> ORGANISM: Homo sapiens

<400> SEQUENCE: 65
aaagccacca agggaauugu gga                                              23

<210> SEQ ID NO 66
<211> LENGTH: 23
<212> TYPE: RNA
<213> ORGANISM: Homo sapiens

<400> SEQUENCE: 66
gaggcacuug gccuugcuga gcu                                              23

<210> SEQ ID NO 67
<211> LENGTH: 23
<212> TYPE: RNA
<213> ORGANISM: Homo sapiens

<400> SEQUENCE: 67
gaucuguucc ucauagcuau acu                                              23

<210> SEQ ID NO 68
<211> LENGTH: 23
<212> TYPE: RNA
<213> ORGANISM: Homo sapiens

<400> SEQUENCE: 68
uaaggcagag gcucccauug gaa                                              23

<210> SEQ ID NO 69
<211> LENGTH: 23
<212> TYPE: RNA
<213> ORGANISM: Homo sapiens

<400> SEQUENCE: 69
aaggcuaaau aucaguguua auu                                              23

<210> SEQ ID NO 70
<211> LENGTH: 23
<212> TYPE: RNA
<213> ORGANISM: Homo sapiens

<400> SEQUENCE: 70
aacuuggaga accagauuau auu                                              23

<210> SEQ ID NO 71
<211> LENGTH: 23
<212> TYPE: RNA
<213> ORGANISM: Homo sapiens

<400> SEQUENCE: 71
aauaccauau guccuuauca uuu                                              23

<210> SEQ ID NO 72
<211> LENGTH: 23
<212> TYPE: RNA
<213> ORGANISM: Homo sapiens

<400> SEQUENCE: 72
aagcaacuug guaacagaac uuu                                              23

<210> SEQ ID NO 73
```

```
<211> LENGTH: 23
<212> TYPE: RNA
<213> ORGANISM: Homo sapiens

<400> SEQUENCE: 73
aaagaggaca cuucaucuua cuu                                              23

<210> SEQ ID NO 74
<211> LENGTH: 23
<212> TYPE: RNA
<213> ORGANISM: Homo sapiens

<400> SEQUENCE: 74
aauccuuacu guaggaaauc auu                                              23

<210> SEQ ID NO 75
<211> LENGTH: 23
<212> TYPE: RNA
<213> ORGANISM: Homo sapiens

<400> SEQUENCE: 75
aaggcaucca ugaauacgac uuu                                              23

<210> SEQ ID NO 76
<211> LENGTH: 23
<212> TYPE: RNA
<213> ORGANISM: Homo sapiens

<400> SEQUENCE: 76
aaugucucag aaucaacauu cuu                                              23

<210> SEQ ID NO 77
<211> LENGTH: 23
<212> TYPE: RNA
<213> ORGANISM: Homo sapiens

<400> SEQUENCE: 77
aaacaccaaa uagauaucau guu                                              23

<210> SEQ ID NO 78
<211> LENGTH: 23
<212> TYPE: RNA
<213> ORGANISM: Homo sapiens

<400> SEQUENCE: 78
aaggaaacgu ugguuugaau guu                                              23

<210> SEQ ID NO 79
<211> LENGTH: 23
<212> TYPE: RNA
<213> ORGANISM: Homo sapiens

<400> SEQUENCE: 79
aauagcaguu uacaaccaga auu                                              23

<210> SEQ ID NO 80
<211> LENGTH: 23
<212> TYPE: RNA
<213> ORGANISM: Homo sapiens

<400> SEQUENCE: 80
aacagauaca guauguauac auu                                              23

<210> SEQ ID NO 81
```

```
<211> LENGTH: 23
<212> TYPE: RNA
<213> ORGANISM: Homo sapiens

<400> SEQUENCE: 81
aaaggcaucc augaauacga cuu                                              23

<210> SEQ ID NO 82
<211> LENGTH: 23
<212> TYPE: RNA
<213> ORGANISM: Homo sapiens

<400> SEQUENCE: 82
aaugucucca uaauucuguu cuu                                              23

<210> SEQ ID NO 83
<211> LENGTH: 23
<212> TYPE: RNA
<213> ORGANISM: Homo sapiens

<400> SEQUENCE: 83
aaauaccaua uguccuuauc auu                                              23

<210> SEQ ID NO 84
<211> LENGTH: 23
<212> TYPE: RNA
<213> ORGANISM: Homo sapiens

<400> SEQUENCE: 84
aacguaacga gugaaauaga auu                                              23

<210> SEQ ID NO 85
<211> LENGTH: 23
<212> TYPE: RNA
<213> ORGANISM: Homo sapiens

<400> SEQUENCE: 85
aaguccaagg cuggcgacag cuu                                              23

<210> SEQ ID NO 86
<211> LENGTH: 23
<212> TYPE: RNA
<213> ORGANISM: Homo sapiens

<400> SEQUENCE: 86
aaguucaugg uaucgugcau guu                                              23

<210> SEQ ID NO 87
<211> LENGTH: 23
<212> TYPE: RNA
<213> ORGANISM: Homo sapiens

<400> SEQUENCE: 87
aauaucacac aagugucuuc auu                                              23

<210> SEQ ID NO 88
<211> LENGTH: 23
<212> TYPE: RNA
<213> ORGANISM: Homo sapiens

<400> SEQUENCE: 88
aauugugagc aucaaagacu auu                                              23

<210> SEQ ID NO 89
```

```
<211> LENGTH: 23
<212> TYPE: RNA
<213> ORGANISM: Homo sapiens

<400> SEQUENCE: 89
aaggaauggu ggaaacaagg guu                                              23

<210> SEQ ID NO 90
<211> LENGTH: 23
<212> TYPE: RNA
<213> ORGANISM: Homo sapiens

<400> SEQUENCE: 90
aaaugugucc acgaaguagc uuu                                              23

<210> SEQ ID NO 91
<211> LENGTH: 23
<212> TYPE: RNA
<213> ORGANISM: Homo sapiens

<400> SEQUENCE: 91
aagcuaaugc uguuuaccgu guu                                              23

<210> SEQ ID NO 92
<211> LENGTH: 23
<212> TYPE: RNA
<213> ORGANISM: Homo sapiens

<400> SEQUENCE: 92
aacuuuaugg ugaccuccua uuu                                              23

<210> SEQ ID NO 93
<211> LENGTH: 23
<212> TYPE: RNA
<213> ORGANISM: Homo sapiens

<400> SEQUENCE: 93
aagaaauggc auucguagg uuu                                               23

<210> SEQ ID NO 94
<211> LENGTH: 23
<212> TYPE: RNA
<213> ORGANISM: Homo sapiens

<400> SEQUENCE: 94
aagaucgacu gaccaaucgc cuu                                              23

<210> SEQ ID NO 95
<211> LENGTH: 23
<212> TYPE: RNA
<213> ORGANISM: Homo sapiens

<400> SEQUENCE: 95
aacaaucguc aauaaccggg uuu                                              23

<210> SEQ ID NO 96
<211> LENGTH: 23
<212> TYPE: RNA
<213> ORGANISM: Homo sapiens

<400> SEQUENCE: 96
aagauuugcu guaaugcagg cuu                                              23

<210> SEQ ID NO 97
```

```
<211> LENGTH: 23
<212> TYPE: RNA
<213> ORGANISM: Homo sapiens

<400> SEQUENCE: 97
aaacaaucgu caauaaccgg guu                                              23

<210> SEQ ID NO 98
<211> LENGTH: 23
<212> TYPE: RNA
<213> ORGANISM: Homo sapiens

<400> SEQUENCE: 98
aauggcauuc uguagguuua uag                                              23

<210> SEQ ID NO 99
<211> LENGTH: 23
<212> TYPE: RNA
<213> ORGANISM: Homo sapiens

<400> SEQUENCE: 99
uagggaugag guuaggaaua uuc                                              23

<210> SEQ ID NO 100
<211> LENGTH: 23
<212> TYPE: RNA
<213> ORGANISM: Homo sapiens

<400> SEQUENCE: 100
gaucgccuua auaccagaaa uga                                              23

<210> SEQ ID NO 101
<211> LENGTH: 23
<212> TYPE: RNA
<213> ORGANISM: Homo sapiens

<400> SEQUENCE: 101
aagcccaaac auuuguaaca aac                                              23

<210> SEQ ID NO 102
<211> LENGTH: 23
<212> TYPE: RNA
<213> ORGANISM: Homo sapiens

<400> SEQUENCE: 102
uaggcauauu ucaggcuuua aau                                              23

<210> SEQ ID NO 103
<211> LENGTH: 23
<212> TYPE: RNA
<213> ORGANISM: Homo sapiens

<400> SEQUENCE: 103
aagggcuguu agaaguucua ucu                                              23

<210> SEQ ID NO 104
<211> LENGTH: 23
<212> TYPE: RNA
<213> ORGANISM: Homo sapiens

<400> SEQUENCE: 104
gaccggcguc gagaauuuca acu                                              23

<210> SEQ ID NO 105
```

```
<211> LENGTH: 23
<212> TYPE: RNA
<213> ORGANISM: Homo sapiens

<400> SEQUENCE: 105
cauccgauua ugccuuauuu aua                                              23

<210> SEQ ID NO 106
<211> LENGTH: 23
<212> TYPE: RNA
<213> ORGANISM: Homo sapiens

<400> SEQUENCE: 106
uaggugguca gagaucagaa agg                                              23

<210> SEQ ID NO 107
<211> LENGTH: 23
<212> TYPE: RNA
<213> ORGANISM: Homo sapiens

<400> SEQUENCE: 107
aaggcuggcg acagcuugaa aag                                              23

<210> SEQ ID NO 108
<211> LENGTH: 23
<212> TYPE: RNA
<213> ORGANISM: Homo sapiens

<400> SEQUENCE: 108
cagcccaagg aaugguggaa aca                                              23

<210> SEQ ID NO 109
<211> LENGTH: 23
<212> TYPE: RNA
<213> ORGANISM: Homo sapiens

<400> SEQUENCE: 109
uaugucauga gaaggcuaaa uau                                              23

<210> SEQ ID NO 110
<211> LENGTH: 23
<212> TYPE: RNA
<213> ORGANISM: Homo sapiens

<400> SEQUENCE: 110
gagcggcaag uccaccuucc uga                                              23

<210> SEQ ID NO 111
<211> LENGTH: 23
<212> TYPE: RNA
<213> ORGANISM: Homo sapiens

<400> SEQUENCE: 111
aaugccuucu cauuuaauuc uga                                              23

<210> SEQ ID NO 112
<211> LENGTH: 23
<212> TYPE: RNA
<213> ORGANISM: Homo sapiens

<400> SEQUENCE: 112
aaggcaagcu aaugcuguuu acc                                              23

<210> SEQ ID NO 113
```

```
<211> LENGTH: 23
<212> TYPE: RNA
<213> ORGANISM: Homo sapiens

<400> SEQUENCE: 113
aaagcccaaa cauuuguaac aaa                                              23

<210> SEQ ID NO 114
<211> LENGTH: 23
<212> TYPE: RNA
<213> ORGANISM: Homo sapiens

<400> SEQUENCE: 114
caucgccaag auuugcugua aug                                              23

<210> SEQ ID NO 115
<211> LENGTH: 23
<212> TYPE: RNA
<213> ORGANISM: Homo sapiens

<400> SEQUENCE: 115
uaagggcugu uagaaguucu auc                                              23

<210> SEQ ID NO 116
<211> LENGTH: 23
<212> TYPE: RNA
<213> ORGANISM: Homo sapiens

<400> SEQUENCE: 116
uaugggcaga cagcggcaua cag                                              23

<210> SEQ ID NO 117
<211> LENGTH: 23
<212> TYPE: RNA
<213> ORGANISM: Homo sapiens

<400> SEQUENCE: 117
aacuccacac ugugccauuu gug                                              23

<210> SEQ ID NO 118
<211> LENGTH: 23
<212> TYPE: RNA
<213> ORGANISM: Homo sapiens

<400> SEQUENCE: 118
gaccaggugc uuauggaaga ucg                                              23

<210> SEQ ID NO 119
<211> LENGTH: 23
<212> TYPE: RNA
<213> ORGANISM: Homo sapiens

<400> SEQUENCE: 119
caugccugua aagcccaaac auu                                              23

<210> SEQ ID NO 120
<211> LENGTH: 23
<212> TYPE: RNA
<213> ORGANISM: Homo sapiens

<400> SEQUENCE: 120
aauugcagug cuaaugaaua ucg                                              23

<210> SEQ ID NO 121
```

```
<211> LENGTH: 23
<212> TYPE: RNA
<213> ORGANISM: Homo sapiens

<400> SEQUENCE: 121
uaccaccaag aaguguugaa aca                                           23

<210> SEQ ID NO 122
<211> LENGTH: 23
<212> TYPE: RNA
<213> ORGANISM: Homo sapiens

<400> SEQUENCE: 122
aagaggacac uucaucuuac uua                                           23

<210> SEQ ID NO 123
<211> LENGTH: 23
<212> TYPE: RNA
<213> ORGANISM: Homo sapiens

<400> SEQUENCE: 123
gaggccgagc agcaacgcaa guc                                           23

<210> SEQ ID NO 124
<211> LENGTH: 23
<212> TYPE: RNA
<213> ORGANISM: Homo sapiens

<400> SEQUENCE: 124
aaguccaagg agaucgacaa aug                                           23

<210> SEQ ID NO 125
<211> LENGTH: 23
<212> TYPE: RNA
<213> ORGANISM: Homo sapiens

<400> SEQUENCE: 125
aagcccuuau accaccacuu cac                                           23

<210> SEQ ID NO 126
<211> LENGTH: 23
<212> TYPE: RNA
<213> ORGANISM: Homo sapiens

<400> SEQUENCE: 126
uagaagguuu agccuucaua uuu                                           23

<210> SEQ ID NO 127
<211> LENGTH: 23
<212> TYPE: RNA
<213> ORGANISM: Homo sapiens

<400> SEQUENCE: 127
aacccucaaa uuggugcuuu cau                                           23

<210> SEQ ID NO 128
<211> LENGTH: 23
<212> TYPE: RNA
<213> ORGANISM: Homo sapiens

<400> SEQUENCE: 128
aacccucaaa uuggugcuuu cau                                           23

<210> SEQ ID NO 129
```

```
<211> LENGTH: 23
<212> TYPE: RNA
<213> ORGANISM: Homo sapiens

<400> SEQUENCE: 129
uaagguguau uggcauguaa uuu                                            23

<210> SEQ ID NO 130
<211> LENGTH: 23
<212> TYPE: RNA
<213> ORGANISM: Homo sapiens

<400> SEQUENCE: 130
aaauggcauu cuguagguuu aua                                            23

<210> SEQ ID NO 131
<211> LENGTH: 23
<212> TYPE: RNA
<213> ORGANISM: Homo sapiens

<400> SEQUENCE: 131
caaggcuggc gacagcuuga aaa                                            23

<210> SEQ ID NO 132
<211> LENGTH: 23
<212> TYPE: RNA
<213> ORGANISM: Homo sapiens

<400> SEQUENCE: 132
gaugcucgag agaagcuuca uau                                            23

<210> SEQ ID NO 133
<211> LENGTH: 23
<212> TYPE: RNA
<213> ORGANISM: Homo sapiens

<400> SEQUENCE: 133
gaucgcagau acauucauag uga                                            23

<210> SEQ ID NO 134
<211> LENGTH: 23
<212> TYPE: RNA
<213> ORGANISM: Homo sapiens

<400> SEQUENCE: 134
gaggacacuu caucuuacuu aag                                            23

<210> SEQ ID NO 135
<211> LENGTH: 23
<212> TYPE: RNA
<213> ORGANISM: Homo sapiens

<400> SEQUENCE: 135
gagaguuuac ccauacauuu agc                                            23

<210> SEQ ID NO 136
<211> LENGTH: 23
<212> TYPE: RNA
<213> ORGANISM: Homo sapiens

<400> SEQUENCE: 136
gaaguguuga aacaccaaau aga                                            23

<210> SEQ ID NO 137
```

```
<211> LENGTH: 23
<212> TYPE: RNA
<213> ORGANISM: Homo sapiens

<400> SEQUENCE: 137
aaggugcuca uaauuucacu aug                                              23

<210> SEQ ID NO 138
<211> LENGTH: 23
<212> TYPE: RNA
<213> ORGANISM: Homo sapiens

<400> SEQUENCE: 138
gaaggcuaaa uaucaguguu aau                                              23

<210> SEQ ID NO 139
<211> LENGTH: 23
<212> TYPE: RNA
<213> ORGANISM: Homo sapiens

<400> SEQUENCE: 139
uagcauaauu gcagugcuaa uga                                              23

<210> SEQ ID NO 140
<211> LENGTH: 23
<212> TYPE: RNA
<213> ORGANISM: Homo sapiens

<400> SEQUENCE: 140
uaggcuguau guagugcuac aau                                              23

<210> SEQ ID NO 141
<211> LENGTH: 23
<212> TYPE: RNA
<213> ORGANISM: Homo sapiens

<400> SEQUENCE: 141
aagcagaaau caccaaguuu ccc                                              23

<210> SEQ ID NO 142
<211> LENGTH: 23
<212> TYPE: RNA
<213> ORGANISM: Homo sapiens

<400> SEQUENCE: 142
uaucucaguu ggucaguaaa gac                                              23

<210> SEQ ID NO 143
<211> LENGTH: 23
<212> TYPE: RNA
<213> ORGANISM: Homo sapiens

<400> SEQUENCE: 143
aagguguccu uaaauacuug uag                                              23

<210> SEQ ID NO 144
<211> LENGTH: 23
<212> TYPE: RNA
<213> ORGANISM: Homo sapiens

<400> SEQUENCE: 144
gaaugccuuc ucauuuaauu cug                                              23

<210> SEQ ID NO 145
```

```
<211> LENGTH: 23
<212> TYPE: RNA
<213> ORGANISM: Homo sapiens

<400> SEQUENCE: 145
aagacuauuu ccuagaauuu gaa                                             23

<210> SEQ ID NO 146
<211> LENGTH: 17
<212> TYPE: PRT
<213> ORGANISM: Mus musculus

<400> SEQUENCE: 146

Leu Leu Leu Leu Gly Thr Gly Glu Ser Gly Lys Ser Thr Phe Ile Lys
1               5                   10                  15

Gln

<210> SEQ ID NO 147
<211> LENGTH: 17
<212> TYPE: PRT
<213> ORGANISM: Homo sapiens

<400> SEQUENCE: 147

Ile Leu Leu Leu Gly Ala Gly Glu Ser Gly Lys Ser Thr Phe Leu Lys
1               5                   10                  15

Gln

<210> SEQ ID NO 148
<211> LENGTH: 17
<212> TYPE: PRT
<213> ORGANISM: Homo sapiens

<400> SEQUENCE: 148

Leu Leu Leu Leu Gly Pro Gly Glu Ser Gly Lys Ser Thr Phe Ile Lys
1               5                   10                  15

Gln

<210> SEQ ID NO 149
<211> LENGTH: 17
<212> TYPE: PRT
<213> ORGANISM: Bovine

<400> SEQUENCE: 149

Leu Leu Leu Leu Gly Thr Ser Asn Ser Gly Lys Ser Thr Ile Val Lys
1               5                   10                  15

Gln

<210> SEQ ID NO 150
<211> LENGTH: 17
<212> TYPE: PRT
<213> ORGANISM: Homo sapiens

<400> SEQUENCE: 150

Leu Leu Leu Leu Gly Ala Gly Glu Ser Gly Lys Ser Thr Ile Val Lys
1               5                   10                  15

Gln

<210> SEQ ID NO 151
<211> LENGTH: 6
<212> TYPE: PRT
<213> ORGANISM: Homo sapiens

<400> SEQUENCE: 151
```

Thr Thr Ala Ile Asp Thr
1               5

<210> SEQ ID NO 152
<211> LENGTH: 6
<212> TYPE: PRT
<213> ORGANISM: Homo sapiens

<400> SEQUENCE: 152

Thr Thr Ala Ile Asn Thr
1               5

<210> SEQ ID NO 153
<211> LENGTH: 6
<212> TYPE: PRT
<213> ORGANISM: Bovine

<400> SEQUENCE: 153

Thr Cys Ala Val Asp Thr
1               5

<210> SEQ ID NO 154
<211> LENGTH: 6
<212> TYPE: PRT
<213> ORGANISM: Homo sapiens

<400> SEQUENCE: 154

Thr Cys Ala Thr Asp Thr
1               5

<210> SEQ ID NO 155
<211> LENGTH: 7
<212> TYPE: PRT
<213> ORGANISM: Mus musculus

<400> SEQUENCE: 155

Leu Lys Asp Cys Gly Leu Phe
1               5

<210> SEQ ID NO 156
<211> LENGTH: 7
<212> TYPE: PRT
<213> ORGANISM: Bovine

<400> SEQUENCE: 156

Leu Arg Gln Tyr Glu Leu Leu
1               5

<210> SEQ ID NO 157
<211> LENGTH: 7
<212> TYPE: PRT
<213> ORGANISM: Bovine

<400> SEQUENCE: 157

Leu Lys Tyr Ile Gly Leu Cys
1               5

<210> SEQ ID NO 158
<211> LENGTH: 7
<212> TYPE: PRT
<213> ORGANISM: Mus musculus

<400> SEQUENCE: 158

Leu Lys Glu Tyr Asn Leu Val
1               5

```
<210> SEQ ID NO 159
<211> LENGTH: 7
<212> TYPE: PRT
<213> ORGANISM: Homo sapiens

<400> SEQUENCE: 159

Leu Lys Asp Ile Met Leu Gln
1               5

<210> SEQ ID NO 160
<211> LENGTH: 7
<212> TYPE: PRT
<213> ORGANISM: Homo sapiens

<400> SEQUENCE: 160

Leu Lys Gln Leu Met Leu Glu
1               5

<210> SEQ ID NO 161
<211> LENGTH: 7
<212> TYPE: PRT
<213> ORGANISM: Homo sapiens

<400> SEQUENCE: 161

Leu Asp Glu Ile Asn Leu Leu
1               5

<210> SEQ ID NO 162
<211> LENGTH: 6
<212> TYPE: PRT
<213> ORGANISM: Homo sapiens

<400> SEQUENCE: 162

Asp Val Gly Gly Gln Arg
1               5

<210> SEQ ID NO 163
<211> LENGTH: 7
<212> TYPE: PRT
<213> ORGANISM: Homo sapiens
<220> FEATURE:
<221> NAME/KEY: VARIANT
<222> LOCATION: 6
<223> OTHER INFORMATION: Xaa = any amino acid

<400> SEQUENCE: 163

Leu Phe Leu Asn Lys Xaa Asp
1               5
```